US006764851B2

(12) United States Patent
Nikolau et al.

(10) Patent No.: US 6,764,851 B2
(45) Date of Patent: *Jul. 20, 2004

(54) MATERIALS AND METHODS FOR THE ALTERATION OF ENZYME AND ACETYL COA LEVELS IN PLANTS

(75) Inventors: Basil J. Nikolau, Ames, IA (US); Eve S. Wurtele, Ames, IA (US); David J. Oliver, Ames, IA (US); Robert Behal, Ames, IA (US); Patrick S. Schnable, Ames, IA (US); Jinshan Ke, Foster City, CA (US); Jerry L. Johnson, St. Paul, MN (US); Carolyn C. Allred, Ames, IA (US); Beth Fatland, Ames, IA (US); Isabelle Lutziger, Ames, IA (US); Tsui-Jung Wen, Ames, IA (US)

(73) Assignee: Iowa State University Research Foundation, Inc., Ames, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 353 days.

(21) Appl. No.: 09/344,882

(22) Filed: Jun. 25, 1999

(65) Prior Publication Data

US 2002/0162137 A1 Oct. 31, 2002

Related U.S. Application Data

(60) Provisional application No. 60/090,717, filed on Jun. 26, 1998.

(51) Int. Cl.$^7$ ............................ C12N 15/74; C12N 5/04; C12N 5/10; C12N 15/82; C12N 15/87

(52) U.S. Cl. ..................... 435/320.1; 435/419; 435/468; 536/23.6; 536/34.5; 800/281

(58) Field of Search .............................. 435/320.1, 419, 435/468; 536/23.6, 24.5; 800/278, 281, 286

(56) References Cited

U.S. PATENT DOCUMENTS 5,684,242 A  11/1997  Schnable et al. ........... 800/205

FOREIGN PATENT DOCUMENTS

| WO | WO 97/27295 | 7/1997 |
|---|---|---|
| WO | WO 97/32986 | 9/1997 |
| WO | WO 98/00557 | 1/1998 |
| WO | WO 98/06831 | 2/1998 |
| WO | WO 98/53085 | 11/1998 |
| WO | WO 99/00505 | 1/1999 |
| WO | WO 99/13067 | 3/1999 |
| WO | WO 00/11199 | 3/2000 |

OTHER PUBLICATIONS

Smyth Cosuppression at a distance Current Biology 1997 7:R793–R795.*
Bourguignon et al. Isolation characterization, and sequence analysis of a cDNA clone encoding L–protein, the dihydrolipoamide dehydrogenase component of the glycine cleavage system from pea–leaf mitochondria Eur. J Biochem,. 204.865–873 1992.*
Newman, et al. Genes Galore: A Summary of Methods for Accessing Results from Large–Scale Partial Sequencing of Anonymous Arabidopsis cDNA Clones Plant Physiol, 1994 106:1241–1255.*
Camp et al., *Plant Physiol.*, 77, 571–577 (1985).
Cui et al., *Science*, 272, 1334–1336 (1996).
Elshourbagy et al., *J. Biol. Chem.*, 265 (3), 1430–1435 (1990).
Elshourbagy et al., *Eur. J. Biochem.*, 204, 491–499 (1992).
Engels et al., *Microbiology*, 143, 3543–3553 (1997).
Fritsch et al., *Plant Physiol.*, 63, 687–691 (1979).
Guan et al., *J. Biol. Chem.*, 270(10), 5412–5417 (1995).
Huang et al., *Arch. Biochem. Biophys.*, 140, 158–173 (1970).
Johnston et al., *Biochimica et Biophysica Acta, 1321*, 200–206 (1997).
Kaethner et al., *Planta, 163*, 290–294 (1985).
Lee et al., *J. Biol. Chem.*, 265, 7413–7418 (1990).
Luethy et al., *Biochim. Biophys. Acta, 1187 (1)*, 95–98 (1994).
Luethy et al., *Gene, 164*(2), 251–254 (1995).
Moon et al., *Biochimica et Biophysica Acta, 1307*, 280–284 (1996).

(List continued on next page.)

*Primary Examiner*—Remy Yucel
*Assistant Examiner*—Konstantina Katcheves
(74) *Attorney, Agent, or Firm*—Leydig, Voit & Mayer, Ltd.

(57) ABSTRACT

The present invention provides nucleic acid and amino acid sequences of acetyl CoA synthetase (ACS), plastidic pyruvate dehydrogenase (pPDH), ATP citrate lyase (ACL), Arabidopsis pyruvate decarboxylase (PDC), and Arabidopsis aldehyde dehydrogenase (ALDH), specifically ALDH-2 and ALDH-4. The present invention also provides a recombinant vector comprising a nucleic acid sequence encoding one of the aforementioned enzymes, an antisense sequence thereto or a ribozyme therefor, a cell transformed with such a vector, antibodies to the enzymes, a plant cell, a plant tissue, a plant organ or a plant in which the level of an enzyme has been altered, and a method of producing such a plant cell, plant tissue, plant organ or plant. Desirably, alteration of the level of enzyme results in an alteration of the level of acetyl CoA in the plant cell, plant tissue, plant organ or plant. In addition, the present invention provides a recombinant vector comprising an antisense sequence of a nucleic acid sequence encoding pyruvate decarboxylase (PDC), the E1$_\alpha$subunit of pPDH, the E1$_\beta$subunit of pPDH, the E2 subunit of pPDH, mitochondrial pyurvate dehydrogenase (mtPDH) or aldehyde dehydrogenase (ALDH) or a ribozyme that can cleave an RNA molecule encoding PDC, E1$_\alpha$pPDH, E1$_\beta$pPDH, E2 pPDH, mtPDH or ALDH.

16 Claims, 15 Drawing Sheets

OTHER PUBLICATIONS

Mooney et al., *Plant Physiol.*, *120*, 443–451 (1999).
Nelson et al., *Plant Physiol.*, *55*, 69–72 (1975).
Ratledge et al., *Lipids*, *32(1)*, 7–12 (1997).
Reid et al., *Plant Physiol.*, *59*, 842–848 (1977).
Roughan et al., *Analyt. Biochem.*, *216*, 77–82 (1994).
Sauer et al., *Z. Naturforsch.*, *39c*, 268–275 (1984).
Taylor et al., *Planta*, *188*, 225–231 (1992).
Thompson et al., *Plant Physiol.*, *59*, 854–858 (1977).
Treede et al., *Z. Naturforsch*, *41c*, 1011–1017 (1986).
Williams et al., *Plant Physiol.*, *64*, 1099–1103 (1979).
Zeiher et al., *Plant Physiol.*, *96*, 382–389 (1991).
Behal et al., EMBL Accession No. AF036618, XP002126950 (Jan. 5, 1998).
Bevan et al., EMBL Accession No. Z97340, XP002134339 (Jul. 4, 1997).
Bevan et al., EMBL Accession No. AL031804, XP002134360 (Oct. 1, 1998) & TREMBL Accession No. 082647 (Nov. 1, 1998).
Bucher et al., *EMBO Journal*, *13* (12), 2755–2763 (1994).
Conner et al., *Database BIOSIS* (*Online*), Data Accession No. PREV199799296162, XP002134361, Abstract (1996) & *Planta*, *200* (2), 195–202 (1996).
DBEST ID: 14439, XP002134341 (Nov. 10, 1992) & EMBL Accession No. Z18045 (Nov. 6, 1992).
DBEST ID: 31724, XP002134350 (Sep. 9, 1993) & EMBL Accession No. Z26027 (Sep. 8, 1993).
DBEST ID: 316729, XP002134342 (Apr. 14, 1993) & EMBL Accession No. R30081 (Aug. 11, 1995).
DBEST ID: 328510, XP002134352 (Jul. 25, 1995) & EMBL Accession No. R90074 (Aug. 28, 1995).
DBEST ID: 378529, XP002134343 (Nov. 6, 1995) & EMBL Accession No. H76244 (Nov. 10, 1995).
DBEST ID: 1436389, XP002134345 (Jan. 5, 1998) & EMBL Accession No. N96514 (Apr. 19, 1996).
DBEST ID: 1436723, XP002134344 (Jan. 5, 1998) & EMBL Accession No. N97183 (Apr. 19, 1996).
DBEST ID:504075, XP002134353 (Aug. 16, 1995) & EMBL Accession No. N97215 (Apr. 19, 1996).
DBEST ID: 551062, XP002134357 (Aug. 16, 1995) & EMBL Accession No. W43179 (May 27, 1996).
DBEST ID: 1437099, XP002134349 (Jan. 5, 1998) & EMBL Accession No. W43461 (May 27, 1996).
DBEST ID: 1276510, XP002134354 (Sep. 19, 1997) & EMBL Accession No. AA597828 (Sep. 24, 1997).
Desprez et al., EMBL Accession No. Z25661, XP002134347 (Aug. 24, 1993) & TREMBL Accession No. Q42036 (Nov. 1, 1996).
Desprez et al., EMBL Accession No. Z33810, XP002134348 (May 23, 1994).
Dolferus et al., EMBL Accession No. U71121, XP002134351 (Oct. 11, 1996) & TREMBL Accession No. Q96535 (Feb. 1, 1997).
Dolferus et al., EMBL Accession No. U71122, XP002134356 (Oct. 11, 1996) & TRENBL Accession No. Q96536 (Feb. 1, 1997).
Etchegaray et al., *Database BIOSIS* (*Online*), Database Accession No. 179045, XP002127203, Abstract (1998) & *Biochemistry and Molecular Biology International*, *44* (2), 235–243 (1998).
Federspiel et al., EMBL Accession No. AC002292, XP002134340 (Jun. 20, 1997) & TREMBL Accession No. 022718 (Jan. 1, 1998).
Hofte et al., EMBL Accession No. Z26232, XP002134346 (Sep. 10, 1993) & TREMBL Accession No. Q42079 (Nov. 1, 1996).
Nakamura, EMBL Accession No. AB005232, XP002134355 (Jul. 18, 1997).
Nakamura, EMBL Accession No. AB023034, XP002134359 (Feb. 5, 1999).
Nakamura, EMBL Accession No. AB026636, XP002134358 (May 7, 1999).
Newman et al., EMBL Accession No. T13703, XP002134337 (Mar. 6, 1994).
Newman et al., EMBL Accession No. T44006, XP002134338 (Feb. 4, 1995).
Newman et al., EMBL Accession No. AA585946, XP002134335 (Sep. 13, 1997).
Newman, DBEST ID: 1427622, XP002134337 (Dec. 30, 1997) & EMBL Accession No. AA720359 (Jan. 7, 1998).
Rangasamy et al., *Database BIOSIS* (*Online*), Database Accession No. PREV199799687761, XP002134366, Abstract (1997) & *Plant Cell Reports*, *16* (10), 700–704 (1997).

* cited by examiner

```
   1  tcaaagatca tccccatcgg agaatcttct cctccatagg aaaatgtcgt ctaattccct
  61  gaggcatgtc gagtccatgt cccagctacc ctcaggtgcc ggaaagatct ctcaattaaa
 121  cgccgtcgtg ttaggagaat cccttgcatc ggaggagaat gatctcgtct ttcccagcaa
 181  ggaattctcc ggccaggctc ttgtttcctc cctcaacag tacatggaaa tgcataagag
 241  gtcgatggat gaccctgctg cttttggtc tgatattgcg tctgagtttt actggaagca
 301  gaaatggggt gaccaagtgt tttccgagaa tctcgatgtc aggaagggtc ctattagcat
 361  cgagtggttt aaaggcggaa tcaccaatat ttgctacaac tgtttggaca aaaacgttga
 421  agctggtttg ggcgataaga cagccataca ctgggaagga aatgaacttg gggtagatgc
 481  ttccttaact tattctgagt tgctccaacg agtttgccag cttgctaatt acttgaaaga
 541  taatggagtg aagaagggtg atgctgttgt aatttattta cctatgttga tggaacttcc
 601  catcgctatg cttgcatgtg caaggatcgg agctgttcat tcggtcgtat ttgctggatt
 661  ttctgcggac tctcttgccc aaagaatcgt tgattgcaag ccaaatgtaa tactgacttg
 721  caatgctgtt aaaagaggcc ctaagaccat aaaccttaaa gctattgttg atgctgcact
 781  tgaccaatct tctaaagatg gagtctctgt aggcatatgc ttgacctatg acaactcatt
 841  agcgacaaca agggaaaaca ctaaatggca gaatggaaga gatgtgtggt ggcaggatgt
 901  tatttctcaa tatccaacat cgtgtgaggt ggaatgggtt gatgcagaag atcccctgtt
 961  tttgctctac accagtggaa gtactgggaa gccaaagggt gtcctacaca aactggagg
1021  gtatatgatc tacactgcta caacgttcaa atatgcattt gactacaaat caacagatgt
1081  atactggtgt acagcagatt gtggttggat aactggccat agctatgtta cttatggacc
1141  aatgcttaat ggagccactg ttgttgtcct tgagggggct ccaaactacc ctgaccctgg
1201  acgctgtcgg gatattgttg acaaatacaa ggtttcaata ttttatactg ccccaacatt
1261  ggtgaggtct ctcatgcgcg atgacgataa gtttgtaaca cgtcactcgc gcaaatcgct
1321  gcgggtcctt ggaagtgttg gtgagcccat caatccagt gcctggagat ggttcttcaa
1381  tgtagtcggt gattcaaggt gtcccatttc agatacgtgg tggcaaactg aaactggtgg
1441  cttcatgata accccattgc caggtgcttg ccccagaaa cctggttcag ccactttccc
1501  tttctttggt gttcagcctg tcatagttga tgaaaagggc aatgaaatcg aaggcgagtg
1561  tagtggttat ctttgtgtca aaggttcatg gcccggggcg tttcgaactc tgtttgggga
1621  tcatgaaaga tacgaaacca catactttaa accttttgcc ggatatatt tcagtggtga
1681  tggttgcagc agagacaagg atggttacta ctggcttaca gggaggttg atgatgttat
1741  caacgtcagt ggccatcgaa tcggaactgc tgaagtagaa tctgctctgg ttttacaccc
1801  tcaatgtgca gaagcagctg ttgtaggcat agaacatgag gtaaaaggtc agggaattta
1861  tgcgtttgtc actcttctgg aaggtgttcc ttacagcgag gagcttcgta aaagcctagt
1921  actaatggtc cgaaatcaga ttggggcttt tgcagcaccg gacagaatac attgggcacc
1981  agggttgcca agacgagaa gcggaaagat aatgaggaga tcttgagaa agattgcttc
2041  gaggcaatta gaagaactcg gagatactag cacactcgcg gatcctagtg tagttgatca
2101  gcttattgca cttgccgatg tgtgatgact aaccatagca tatgagccaa tggagagtaa
2161  tggagttttg tgcatctata tatgtttca ggtgtcttat agagggaatg gtacaaaaat
2221  ctgaaacaag attcaggtgt tttggaggga ataaagtaag cagactatat tgttgtgttt
2281  ttgaataaag aaatttcagt ctcatgaatt tggttttgga taagatggtc ataggattat
2341  caaattaatt aaaagttaca aaaatataaa aaaaaaaaa aa     [SEQ ID NO: 1]
```

MSSNSLRHVESMSQLPSGAGKISQLNAVVLGESLASEENDLVFPSKEFSGQALVSSPQQYMEMHKRSMDDPAAF
WSDIASEFYWKQKWGDQVFSENLDVRKGPISIEWFKGGITNICYNCLDKNVEAGLGDKTAIHWEGNELGVDASL
TYSELLQRVCQLANYLKDNGVKKGDAVVIYLPMLMELPIAMLACARIGAVHSVVFAGFSADSLAQRIVDCKPNV
ILTCNAVKRGPKTINLKAIVDAALDQSSKDGVSVGICLTYDNSLATTRENTKWQNGRDVWWQDVISQYPTSCEV
EWVDAEDPLFLLYTSGSTGKPKGVLHTTGGYMIYTATTFKYAFDYKSTDVYWCTADCGWITGHSYVTYGPMLNG
ATVVVLEGAPNYPDPGRCRDIVDKYKVSIFYTAPTLVRSLMRDDDKFVTRHSRKSLRVLGSVGEPINPSAWRWF
FNVVGDSRCPISDTWWQTETGGFMITPLPGAWPQKPGSATFPFFGVQPVIVDEKGNEIEGECSGYLCVKGSWPG
AFRTLFGDHERYETTYFKPFAGYYFSGDGCSRDKDGYYWLTGRVDDVINVSGHRIGTAEVESALVLHPQCAEAA
VVGIEHEVKGQGIYAFVTLLEGVPYSEELRKSLVLMVRNQIGAFAAPDRIHWAPGLPKTRSGKIMRRILRKIAS
RQLEELGDTSTLADPSVVDQLIALADV                                [SEQ ID NO: 2]

FIG. 1

AATGGCCAAGAGGCTGTTTCTACTGGCTTTATCAAGCTCCTTACCAAGTCTGACTCTGTCGTTAGTACCTACCG
TGACCATGTCCATGCCCTCAGCAAAGGTGTCTCTGCTCGTGCTGTTATGAGCGAGCTCTTCGGCAAGGTTACTG
GATGCTGCAGAGGCCAAGGTGGATCCATGCACATGTTCTCCAAAGAACACAACATGCTTGGTGGCTTTGCTTTT
ATTGGTGAAGGCATTCCTGTCGCCACTGGTGCTGCCTTTAGCTCCAAGTACAGGAGGGAAGTCTTGAAACAGGA
TTGTGATGATGTCACTGTCGCCTTTTTCGGAGATGGAACTTGTAACAACGGACAGTTCTTCGAGTGTCTCAACA
TGGCTGCTCTCTATAAACTGCCTATTATCTTTGTTGTCGAGAATAACTTGTGGGCCATTGGGATGTCTCACTTG
AGAGCCACTTCTGACCCCGAGATTTGGAAGAAAGGTCCTGCATTTGGGATGCCTGGTGTTCATGTTGACGGTAT
GGATGTCTTGAAGGTCAGGGAAGTCGCTAAAGAGGCTGTCACTAGAGCTAGAAGAGGAGAAGGTCCAACCTTGG
TTGAATGTGAGACTTATAGATTTAGAGGACACTCCTTGGCTGATCCCGATGAGCTCCGTGATGCTGCTGAGAAA
GCCAAATACGCGGCTAGAGACCCAATCGCAGCATTGAAGAAGTATTTGATAGAGAACAAGCTTGCAAAGGAAGC
AGAGCTAAAGTCAATAGAGAAAAAGATAGACGAGTTGGTGGAGGAAGCGGTTGAGTTTGCAGACGCTAGTCCAC
AGCCCGGTCGCAGTCAGTTGCTAGAGAATGTGTTTGCTGATCCAAAAGGATTTGGAATTGGACCTGATGGACGG
TACAGATGTGAGGACCCCAAGTTTACCGAAGGCACAGCTCAAGTCTGAGAAGACAAGTTTAACCATAAGCTGTC
TACTGTTTCTTCGATGTTTCTATATATCTTATTAAGTTAAATGCTACAGAGAATCAGTTTGAATCATTTGCACT
TTTTGCTTTTTGTTTGGTGTTACTAAATTATCACAAGGTTCTTCTTGTAGTTCGTTGGGTTTTCATTGGTTACC
ACTTAAAAAAAAAAAAAAAAAA                                          [SEQ ID NO: 3]

NGQEAVSTGFIKLLTKSDSVVSTYRDHVHALSKGVSARAVMSELFGKVTGCCRGQGGSMHMFSKEHNMLGGFAF
IGEGIPVATGAAFSSKYRREVLKQDCDDVTVAFFGDGTCNNGQFFECLNMAALYKLPIIFVVENNLWAIGMSHL
RATSDPEIWKKGPAFGMPGVHVDGMDVLKVREVAKEAVTRARRGEGPTLVECETYRFRGHSLADPDELRDAAEK
AKYAARDPIAALKKYLIENKLAKEAELKSIEKKIDELVEEAVEFADASPQPGRSQLLENVFADPKGFGIGPDGR
YRCEDPKFTEGTAQV                                                 [SEQ ID NO: 4]

FIG. 2

```
GCGGATACGTCTGCGAGCACTGGACATGAACTATTGCTTTTCGAGGCTCTTCAGGAAGGTCTGGAAGAAGAGAT
GGACAGAGATCCACATGTATGTGTTATGGGTGAAGATGTTGGCCATTACGGAGGTTCCTACAAGGTAACCAAAG
GCCTTGCTGATAAATTTGGTGACCTCAGGGTTCTCGACACTCCTATTTGTGAAAATGCATTCACCGGTATGGGC
ATTGGAGCTGCCATGACTGGTCTAAGACCCGTTATTGAAGGTATGAACATGGGTTTCCTCCTCCTCGCCTTCAA
CCAAATCTCCAACAACTGTGGAATGCTTCACTACACATCCGGTGGTCAGTTTACGATCCCGGTTGTCATCCGTG
GACCTGGTGGAGTGGGACGCCAGCTTGGTGCTGAGCATTCACAGAGGTTAGAATCTTACTTTCAGTCCATCCCT
GGGATCCAGATGGTTGCTTGCTCAACTCCTTACAACGCCAAAGGGTTGATGAAAGCCGCAATAAGAAGCGAGAA
CCCTGTGATTCTGTTCGAACACGTGCTGCTTTACAATCTCAAGGAGAAAATCCCGGATGAAGATTACATCTGTA
ACCTTGAAGAAGCTGAGATGGTCAGACCTGGCGAGCACATTACCATCCTCACTTACTCGCGAATGAGGTACCAT
GTGATGCAGGCAGCAAAAACTCTGGTGAACAAAGGGTATGACCCCGAGGTTATCGACATCAGGTCACTGAAACC
GTTCGACCTTCACACAATTGGAAACTCGGTGAAGAAAACACATCGGGTTTTGATCGTGGAGGAGTGTATGAGAA
CCGGTGGGATTGGGGCAAGTCTTACAGCTGCCATCAACGAGAACTTTCATGACTACTTAGATGCTCCGGTGATG
TGTTTATCTTCTCAAGACGTTCCTACACCTTACGCTGGTACACTGGAGGAGTGGACCGTGGTTCAACCGGCTCA
GATCGTGACCGCTGTCGAGCAGCTTTGCCAGTAAATTCATATTTATCCGATGAACCATTATTTATCATTTACCT
CTCCATTTCCTTTCTCTGTAGCTTAGTTCTTAAAGAATTTGTCTAAGATGGTTTGTTTTTGTTAAAGTTTGTCT
CCTTTGTTGTGTCTTTTAATATGGTTTGTAACTCAGAATGTTTGTTTGTTAATTTTATCTCCCACTTTCTTTTA
AAAAAAAAAAAAAAAAAAAAAAAA                                        [SEQ ID NO: 5]

ADTSASTGHELLLFEALQEGLEEEMDRDPHVCVMGEDVGHYGGSYKVTKGLADKFGDLRVLDTPICENAFTGMG
IGAAMTGLRPVIEGMNMGFLLLAFNQISNNCGMLHYTSGGQFTIPVVIRGPGGVGRQLGAEHSQRLESYFQSIP
GIQMVACSTPYNAKGLMKAAIRSENPVILFEHVLLYNLKEKIPDEDYICNLEEAEMVRPGEHITILTYSRMRYH
VMQAAKTLVNKGYDPEVIDIRSLKPFDLHTIGNSVKKTHRVLIVEECMRTGGIGASLTAAINENFHDYLDAPVM
CLSSQDVPTPYAGTLEEWTVVQPAQIVTAVEQLCQ                             [SEQ ID NO: 6]
```

FIG. 3

```
   1  AATTCGGCAC GAGACCCAAC CTGTGAAGCT ACCCCCATTC TCTCTCAACG
  51  TTTTCGTTTT GAAATGGCGA GGAAGAAGAT CAGAGAGTAT GACTCAAAGA
 101  GGTTGGTGAA GGAACATTTC AAAAGGCTTT CTGGCAAAGA GCTTCCTATC
 151  AGATCCGTTC AGATTAATGA ACAACTGAT CTAAATGAGC TAGTTGAAAA
 201  GGAACCTTGG CTCTCGTCTG AGAAGCTGGT GGTGAAACCT GACATGTTGT
 251  TTGGAAAGCG TGGCAAGAGT GGTTTGGTTG CCTTGAAATT AGATTTTGCT
 301  GATGTTGCCA CTTTTGTTAA AGAACGTTTG GGAAAAGAGG TAGAGATGAG
 361  TGGATGCAAA GGACCCATAA CAACATTCAT AGTTGAACCA TTTGTTCCAC
 401  ACAATGAGGA GTATTATCTC AATGTTGTCT CGGATCGGCT TGGTTGCAGC
 451  ATAAGCTTTT CTGAGTGTGG AGGAATTGAG ATCGAGGAGA ACTGGGACAA
 501  GGTCAAGACA ATATTTTTAC CAACAGGTGC TTCCCTGACA CCTGAAATAT
 551  GTGCACCTCT TGTCGCAACT CTTCCCTTAG AGATCAAAGC TGAAATTGAA
 601  GAATTTATCA AGTCATTTT CACCCTATTC CAAGATCTTG ATTTCACTTT
 561  CTTGGAGATG AATCCTTTCA CTCTAGTTGA TGGAAGTCCT TATCCTCTGG
 701  ATATGAGGGG TGAGCTTGAT GATACTGCTG CCTTCAAAAA CTTTAAAAAA
 751  TGGGGCGACA TTGAATTTCC TCTGCCATTT GGAAGAGTAA TGAGTCCTAC
 801  AGAAAGCTTT ATCCACGGAC TGGATGAGAA GACAAGTGCG TCTTTGAAGT
 851  TTACCGTTCT GAACCCCAAG GGACGGATTT GGACAATGGT AGCTGGTGGA
 901  GGAGCAAGTG TCATCTATGC GGATACGGTT GGAGATCTCG GTATGCATC
 951  TGAACTTGGC AACTATGCTG AATACAGTGG AGCACCCAAA GAAGATGAAG
1001  TTTTGCAGTA CGCCAGAGTC GTTATTGATT GTGCTACAGC AAACCCGGAT
1051  GGAAAAAGCA GAGCCCTTGT CATCGGAGGC GGAATTGCCA ACTTCACTGA
1101  CGTTGCTGCT ACTTTCAATG GCATAATCCG CGCTCTTAAA GAAAAGGAAG
1151  CAAAGCTGAA AGCAGCAAGG ATGCATATAT TTGTGAGGAG AGGAGGACCA
1201  AACTACCAAA AGGGACTTGC TAAAATGCGA GCCCTTGGAG ATGATATCGG
1251  TGTCCCCATC GAGGTCTATG GCCCAGAAGC AACCATGACA GGTATCTGCA
1301  AGGAGGCAAT CCAGTACATC ACAGCAGCAG CATAAGCTTC TCTCAGTACC
1351  TTCTATGACC AAAACTTTGT CTGTGTTTTA GAGCCTTTAT TTACTGTGGT
1401  TAAGATTACT CAAGCTATAA GATACTTGCA ATTTCTTGAA AACTTCTGTT
1451  GTTCGATTCT CTTTCCCCTA ACGTTTTCTT CAGATTCAAT AAATAATCGT
1501  TACTTTTTAA AAAAAAAAA AAAAAAAAA            [SEQ ID NO: 7]

1  MARKKIREYDSKRLVKEHFKRLSGKELPIRSVQINETTDLNELVEKEPWL
  51  SSEKLVVKPDMLFGKRGKSGLVALKLDFADVATFVKERLGKEVEMSGCKG
 101  PITTFIVEPFVPHNEEYYLNVVSDRLGCSISFSECGGIEIEENWDKVKTI
 151  FLPTGASLTPEICAPLVATLPLEIKAEIEEFIKVIFTLFQDLDFTFLEMN
 201  PFTLVDGSPYPLDMRGELDDTAAFKNFKKWGDIEFPLPFGRVMSPTESFI
 251  HGLDEKTSASLKFTVLNPKGRIWTMVAGGGASVIYADTVGDLGYASELGN
 301  YAEYSGAPKEDEVLQYARVVIDCATANPDGKSRALVIGGGIANFTDVAAT
 361  FNGIIRALKEKEAKLKAARMHIFVRRGGPNYQKGLAKMRALGDDIGVPIE
 401  VYGPEATMTGICKEAIQYITAAA*                  [SEQ ID NO: 8]
```

FIG. 4

```
   1  GATCTCAGCT CTGCAATTAA GAGTGGGAAA GTCCGGGCTC CTACTCACAT
  51  CATCTCCACC ATTTCTGATG ACAGAGGGGA GGAACCATGC TATGCTGGTG
 101  TGCCAATGTC ATCCATCATT GAACAGGGTT ATGGCGTGGG AGATGTCATT
 151  TCCCTCCTAT GGTTCAAACG TAGTCTTCCT CGATATTGTA CCAAATTCAT
 201  CGAGATATGC ATAATGTTGT GCGCTGACCA CGGTCCATGC GTCTCTGGCG
 251  CTCACAACAC CATCGTAACA GCAAGAGCAG GAAAAGACCT TGTCTCAAGT
 301  CTTGTCTCAG GTCTATTAAC AATCGGTCCT AGATTTGGTG GTGCCATTGA
 361  TGATGCAGCA CGATACTTCA AGGACGCTTG TGACAGGAAT CTCACACCTT
 401  ATGAATTCGT GGAAGGCATG AAGAAGAAAG GAATCCGTGT CCCTGGCATT
 451  GGTCACAGGA TAAAGAGCAG AGACAACAGA GACAAAGAG  TGGAGCTGCT
 501  TCAGAAATT  TGCACGGTCTA ACTTCCCTGC AGTGAAGTAC ATGGAATACG
 551  CAGTCCAAGT AGAGACATAC ACACTGTCTA AGCCAACAA  CCTGGTACTC
 601  AACGTCGATG GAGCCATTGG ATCTCTCTTC TTAGACCTTC TCGCTGGAAG
 561  TGGGATGTTC ACAAAACAAG AGATAGACGA AATAGTTCAG ATCGGTTATC
 701  TCAACGGCCT CTTCGTCCTC GCTCGATCCA TCGGTTTAAT CGGGCACACA
 751  TTCGATCAGA AGAGACTGAA GCAGCCACTG TACCGACACC CGTGGGAAGA
 801  TGTCTTGTAC ACCAAGTAAT CATATCATTA TTCACTTCTT CTGGTCGTTC
 851  CTTATTCCTG TTATCATTCT CTCCCATTCA GTTAGGCTAT GTTTGATTAT
 901  ATATTTGTTC TGACACTCTA TCTGTTGTGA TCTCTTAATG CTTGAAAAAA
 951  TAAAAGAAAG TTCAATTTTA GAAGAATTAT AATGTTTTGA TTCTAAATTA
1001  CTCACACTGG CGGCCGCCAC GTGGAGCTCC      [SEQ ID NO: 9]
```

```
   1  DLSSAIKSGK VRAPTHIIST ISDDRGEEPC YAGVPMSSII EQGYGVGDVI
  51  SLLWFKRSLP RYCTKFIEIC IMLCADHGPC VSGAHNTIVT ARAGKDLVSS
 101  LVSGLLTIGP RFGGAIDDAA RYFKDACDRN LTPYEFVEGM KKKGIRVPGI
 151  GHRIKSRDNR DKRVELLQKF ARSNFPAVKY MEYAVQVETY TLSKANNLVL
 201  NVDGAIGSLF LDLLAGSGMF TKQEIDEIVQ IGYLNGLFVL ARSIGLIGHT
 251  FDQKRLKQPL YRHPWEDVLY TK*            [SEQ ID NO: 10]
```

FIG. 5

```
CGCGGCCGCGTCGACTTTCTCTCTACCACCATTTATTCTCTCCTTAATCACTGACTCGACTCGGGTCGTGACCA
GTTTTTTCTATCTGAGCTATGGCAACGGGACAGCTTTTTCTCGTACCACACAAGCTTTGTTCTACAACTATAA
GCAGCTTCCTGTTCAACGAATGCTCGATTTCGACTTTCTCTGTGGACGTGAAACGCCTTCTGTTGCTGGAATCA
TAAATCCTGGTTCTGAAGGTTTTCAAAAGCTCTTTTTCGGGCAGGAGGAAATCGCTATCCCTGTTCATGCCGCC
ATTGAGGCAGCTTGTGCTGCGCATCCAACAGCGGATGTATTCATCAACTTTGCATCTTTTAGGAGTGCTGCTGC
TTCATCCATGGCTGCTTTGAAGCAGCCGACTATTAAAGTTGTGGCAATTATAGCTGAAGGTGTTCCAGAATCAG
ACACTAAGCAGCTGATTGCGTATGCTCGTGCAAACAATAAGGTTGTTATTGGACCGGCTACTGTTGGAGGTATT
CAAGCTGGAGCCTTTAAGATTGGTGATACTGCAGGAACAATTGATAACATTATCCAGTGCAAGCTATACAGACC
TGGATCTGTTGGTTTTGTCTCCAAATCTGGTGGAATGTCTAATGAAATGTACAATACTGTTGCCCGTGTGACTG
ATGGGATCTACGAAGGCATTGCTATTGGTGGAGACGTGTTCCCAGGATCGACTTTATCTGACCACATCCTTCGG
TTTAACAACATCCCACAGATAAAAATGATGGTTGTACTTGGAGAGCTTGGAGGAAGAGATGAATACTCTCTTGT
TGAAGCTTTGAAAGAGGGAAAAGTCAATAAACCTGTGGTTGCTTGGGTCAGTGGAACTTGTGCACGACTCTTCA
AGTCTGAAGTACAGTTTGGTCATGCAGGTGCCAAAAGTGGCGGCGAGATGGAGTCTGCACAAGCCAAGAATCAA
GCTCTCATAGATGCTGGAGCTATTGTTCCCACTTCATTTGAAGCTCTAGAATCTGCAATCAAAGAGACTTTTGA
GAAACTGGTTGAAGAAGGAAAGGTCTCTCCTATCAAGGAAGTCATTCCTCCACAAATCCCTGAGGATCTCAATT
CTGCAATTAAGAGTGGGAAAGTCCGGGCTCCTACTCACATCATCTCCACCATATCTGATGACAGAGGGGAGGAA
CCATGCTATGCTGGTGTTCCAATGTCTTCCATCATCGAACAAGGCTATGGAGTGGGTGATGTCATTTCCCTTCT
ATGGTTCAAACGTAGTCTACCTCGTTACTGTACAAAATTCATTGAGATATGCATAATGCTGTGTGCTGATCACG
GTCCATGCGTCTCCGGCGCTCACAACACCATTGTAACAGCAAGAGCAGGCAAAGACCTCGTCTCAAGTCTTGTC
TCAGGTTTATTGACCATTGGTCCCCGATTTGGTGGTGCCATTGATGACGCTGCTCGATACTTCAAAGACGCGTG
TGACAGGAATCTCACACCTTATGAATTTGTTGAGGGAATGAAGAAAAAGGGAATCCGAGTCCCCGGGATTGGAC
ACAGGATCAAGAGCAGAGACAACAGAGACAAAAGAGTGGAGCTTCTTCAGAAATTTGCTCGGTCCAACTTCCCA
TCAGTGAAGTACATGGAGTACGCAGTGACAGTGGAGACATACACGCTCTCAAAGGCAAACAACCTCGTACTCAA
CGTTGATGGAGCCATTGGATCTCTCTTCTTGGACCTTCTAGCTGGAAGTGGGATGTTCACTAAACAAGAGATTG
ACGAGATTGTTCAGATCGGTTATCTCAACGGTCTGTTTGTTCTTGCTCGCTCCATCGGTTTGATCGGGCACACG
TTTGATCAGAAGAGATTGAAGCAGCCACTGTATCGTCACCCATGGGAAGATGTGTTGTACACCAAGTAAAACTC
ATTTCAATCCTATTTTTGTTATTATTCCAATTAATTAGCCTTTTAAAATTCTTCTGAGAGATGTTTACTTAAAA
AATGCATATCTATATGCTCTTCTTCTGTCTCTTTTGTTGTCATGTATGTTTGTTCACTTCTTCTTCTTTTTCA
ATTATTTAAACTTTCTTTGTCTCTCTTTCTCTGTTACATCCAAATCACCATTTTTTGGGATTCTATGAGTCATG
CTCATGCATGTCTATATCTTAATCGTGATTTGTCCTTCGAAAGTCGACGCGGCCGCG    [SEQ ID NO: 11]
```

```
MATGQLFSRTTQALFYNYKQLPVQRMLDFDFLCGRETPSVAGIINPGSEGFQKLFFGQEEIAIPVHAAIEAACA
AHPTADVFINFASFRSAAASSMAALKQPTIKVVAIIAEGVPESDTKQLIAYARANNKVVIGPATVGGIQAGAFK
IGDTAGTIDNIIQCKLYRPGSVGFVSKSGGMSNEMYNTVARVTDGIYEGIAIGGDVFPGSTLSDHILRFNNIPQ
IKMMVVLGELGGRDEYSLVEALKEGKVNKPVVAWVSGTCARLFKSEVQFGHAGAKSGGEMESAQAKNQALIDAG
AIVPTSFEALESAIKETFEKLVEEGKVSPIKEVIPPQIPEDLNSAIKSGKVRAPTHIISTISDDRGEEPCYAGV
PMSSIIEQGYGVGDVISLLWFKRSLPRYCTKFIEICIMLCADHGPCVSGAHNTIVTARAGKDLVSSLVSGLLTI
GPRFGGAIDDAARYFKDACDRNLTPYEFVEGMKKKGIRVPGIGHRIKSRDNRDKRVELLQKFARSNFPSVKYME
YAVTVETYTLSKANNLVLNVDGAIGSLFLDLLAGSGMFTKQEIDEIVQIGYLNGLFVLARSIGLIGHTFDQKRL
KQPLYRHPWEDVLYTK                                                   [SEQ ID NO: 12]
```

FIG. 6

ATGTCTGCGATACTCCAAGGAGCTGGAGCTGCAACGGCTCTCTCGCCGTTTAATTCTATCGATTCCAACAAACT
CGTTGCTCCTTCTCGCTCTTCTCTTTCAGTGAGGAGCAAGAGATACATTGTTGCCGGATCTGATAGTAAAAGCT
TTGGTTCTAGCCTCGTAGCTCGTCGCTCTGAGCCGTTGATACCAAATGCTGTTACGACGAAGGCGGACACTGCT
GCGAGCTCTACTTCATCAAAGCCTGGGTATGAGCTATTACTTTTCGAGGCTCTTCAAGAAGGTCTAGAAGAAGA
GATGGACAGAGATCCACATGTATGTGTCATGGGTGAAGATGTAGGCCATTACGGAGGCTCATACAAAGTAACTA
AAGGCCTAGCTGATAAGTTTGGCGATCTCAGGGTTCTGGACACTCCAATCTGTGAAAACGCCTTCACCGGTATG
GGCATTGGAGCCGCCATGACAGGACTAAGACCCGTCATCGAAGGTATGAACATGGGGTTTCTACTCTTAGCCTT
CAACCAAATCTCCAACAACTGTGGTATGCTTCACTATACATCCGGTGGTCAATTCACTATCCCGGTTGTTATCC
GTGGGCCTGGAGGTGTGGGCCGGCAGCTCGGAGCCGAGCATTCCCAGCGTCTCGAGTCTTACTTCCAGTCAATC
CCTGGGATCCAGATGGTGGCTTGCTCAACACCTTACAACGCTAAAGGATTGATGAAAGCGGCGATAAGAAGTGA
GAATCCTGTGATTCTGTTTGAACACGTTCTGCTCTATAACCTCAAGGAGAGTATTCCGGATGAAGAATACATAT
GTAATCTGGAAGAAGCAGAAATGGTCAGACCCGGTGAACACATCACGATACTGACGTATTCAAGGATGAGGTAC
CATGTAATGCAGGCTGCAAAGACGCTGGTGAACAAAGGGTATGATCCAGAGGTTATCGACATAAGGTCGTTGAA
GCCGTTTGATCTCTACACAATTGGAAACTCGGTGAAGAAGACACACCGGGTTTTGATTGTGGAGGAATGTATGA
GAACGGGAGGAATCGGAGCCAGTTTGACGGCTGCAATAAACGAGAACTTTCATGATTACTTAGATGCTCCGGTG
ATGTGTTTGTCTTCTCAGGATGTCCCAACTCCTTACGCCGGTACATTGGAAGAATGGACGGTTGTTCAGCCAGC
TCAGATCGTCACTGCCGTCGAACAACTTTGCCAGTAA                          [SEQ ID NO: 13]

MSAILQGAGAATALSPFNSIDSNKLVAPSRSSLSVRSKRYIVAGSDSKSFGSSLVARRSEPLIPNAVTTKADTA
ASSTSSKPGHELLLFEALQEGLEEEMDRDPHVCVMGEDVGHYGGSYKVTKGLADKFGDLRVLDTPICENAFTGM
GIGAAMTGLRPVIEGMNMGFLLLAFNQISNNCGMLHYTSGGQFTIPVVIRGPGGVGRQLGAEHSQRLESYFQSI
PGIQMVACSTPYNAKGLMKAAIRSENPVILFEHVLLYNLKESIPDEEYICNLEEAEMVRPGEHITILTYSRMRY
HVMQAAKTLVNKGYDPEVIDIRSLKPFDLYTIGNSVKKTHRVLIVEECMRTGGIGASLTAAINENFHDYLDAPV
MCLSSQDVPTPYAGTLEEWTVVQPAQIVTAVEQLCQ                          [SEQ ID NO: 14]

FIG. 7

```
AAAATAAAAAGAGTATATCTCTCACACACATACACAAACTTGACAGTTTTTTAATTTCTCTGTTAGTGAACTCA
AACCTTCCCATTTCCATGGACACCAAAATCGGATCGATCGATGATTGCAAGCCGACGAACGGCGACGTCTGTAG
TCCAACAAACGGCACCGTCGCAACAATCCACAACTCTGTTCCTTCCTCCGCTATCACCATCAACTACTGCGACG
CGACTCTCGGCCGTCACTTAGCTCGTCGTCTCGTCCAAGCCGGCGTTACGGATGTTTTCTCTGTTCCCGGAGAT
TTCAACCTCACTTTGCTTGATCACCTCATGGCTGAGCCGGACCTCAACCTAATCGGATGTTGTAACGAGCTAAA
CGCCGGTTACGCTGCCGACGGTTACGCTAGATCTCGTGGAGTCGGCGCTTGCGTTGTTACCTTCACCGTTGGTG
GACTCAGCGTTTTAAACGCGATCGCTGGTGCTTACAGCGAGAATCTTCCTCTTATCTGTATCGTCGGAGGTCCT
AACTCTAACGATTATGGCACTAACCGGATTCTTCATCACACCATTGGATTACCTGATTTTAGCCAAGAGCTTAG
GTGCTTCCAAACGGTGACTTGTTATCAGGCGGTGGTGAACAATTTAGATGATGCTCATGAACAGATTGATAAAG
CAATATCAACAGCTTTGAAAGAGAGCAAGCCTGTGTATATAAGTGTAAGCTGTAACTTAGCAGCGATTCCTCAT
CATACATTTAGCCGTGATCCTGTCCCTTTTCTCTAGCTCCAAGATTGAGCAACAAGATGGGTTTAGAAGCTGC
GGTGGAAGCAACATTGGAGTTTCTGAATAAGGCTGTGAAGCCAGTTATGGTTGGTGGTCCTAAGTTGCGTGTGG
CTAAAGCTTGTGATGCCTTTGTTGAGCTAGCTGATGCTTCAGGCTATGCTTTGGCGATGATGCCTTCTGCGAAA
GGCTTTGTACCAGAGCACCATCCTCATTTCATTGGAACTTATTGGGGAGCAGTGAGCACTCCTTTTTGCTCTGA
GATTGTGGAATCTGCGGATGCTTACATTTTTGCAGGTCCAATCTTCAACGACTATAGCTCTGTTGGTTACTCGC
TTCTCCTCAAGAAAGAAAAAGCCATCGTTGTGCAACCTGATCGTATCACTGTGGCCAATGGTCCTACTTTTGGT
TGCATTTTGATGAGCGATTTCTTCAGGGAATTGTCTAAGAGGGTGAAGCGTAACGAGACTGCATATGAGAACTA
CCATAGGATCTTTGTCCCTGAAGGTAAGCCATTGAAGTGTGAATCAAGAGAGCCATTGAGAGTTAACACAATGT
TCCAGCACATTCAGAAGATGCTCTCTAGTGAAACCGCTGTGATTGCTGAAACCGGTGATTCTTGGTTCAATTGC
CAAAAACTAAAGCTGCCAAAAGGATGTGGGTACGAGTTTCAGATGCAGTATGGATCGATTGGGTGGTCTGTTGG
TGCAACTCTAGGATACGCACAGGCATCACCAGAGAAGCGAGTGTTGGCATTCATCGGTGATGGGAGTTTCCAAG
TCACGGTTCAGGACATATCAACAATGCTGCGTAATGGACAGAAGACGATCATCTTCTTGATTAACAATGGTGGC
TACACCATTGAAGTAGAGATTCATGACGGTCCTTATAACGTGATTAAGAACTGGAACTACACTGGTCTCGTTGA
CGCCATTCATAACGGTGAAGGCAATTGCTGGACTGCAAAGGTGAGATACGAAGAGGAGTTAGTGGAGGCGATTA
CGACAGCGACGACGGAGAAGAAAGATTGTCTATGTTTCATAGAAGTGATTCTTCACAAGGATGATACGAGCAAA
GAGTTGCTTGAGTGGGGCTCACGCGTCTCTGCTGCTAACAGCCGTCCTCCCAATCCTCAGTAGAAGAAGCAACA
CAGAATCTTCAATGCTTCTTACCAATTTAGTGACATTTTCTGATAAGTGTTGATTTTCGACCGTTGGGTTTAA
TCATGTTTCAAACTTATTAGTATCTCTTTCCATGTCGCTTTATCATGGAATAAAGTAAAGCTCCTTTTGCAAAA
AAAAAAAAAA                                                          [SEQ ID NO: 15]
```

FIG. 8A

```
  1  MDTKIGSIDD  CKPTNGDVCS  PTNGTVATIH  NSVPSSAITI  NYCDATLGRH
 51  LARRLVQAGV  TDVFSVPGDF  NLTLLDHLMA  EPDLNLIGCC  NELNAGYAAD
101  GYARSRGVGA  CVVTFTVGGL  SVLNAIAGAY  SENLPLICIV  GGPNSNDYGT
151  NRILHHTIGL  PDFSQELRCF  QTVTCYQAVV  NNLDDAHEQI  DKAISTALKE
201  SKPVYISVSC  NLAAIPHHTF  SRDPVPFSLA  PRLSNKMGLE  AAVEATLEFL
251  NKAVKPVMVG  GPKLRVAKAC  DAFVELADAS  GYALAMMPSA  KGFVPEHHPH
301  FIGTYWGAVS  TPFCSEIVES  ADAYIFAGPI  FNDYSSVGYS  LLLKKEKAIV
351  VQPDRITVAN  GPTFGCILMS  DFFRELSKRV  KRNETAYENY  HRIFVPEGKP
401  LKCESREPLR  VNTMFQHIQK  MLSSETAVIA  ETGDSWFNCQ  KLKLPKGCGY
451  EFQMQYGSIG  WSVGATLGYA  QASPEKRVLA  FIGDGSFQVT  VQDISTMLRN
501  GQKTIIFLIN  NGGYTIEVEI  HDGPYNVIKN  WNYTGLVDAI  HNGEGNCWTA
551  KVRYEEELVE  AITTATTEKK  DCLCFIEVIL  HKDDTSKELL  EWGSRVSAAN
601  SRPPNPQ                                        [SEQ ID NO: 16]
```

FIG. 8B

```
AAAAGTACAGTTTTCTCATAGCTCTATTGTTCGAAAATTCTGAAACGAACGTTACCACTATGGACACTAAGATC
GGATCTATCGACGCGTGTAACCCGACCAACCACGATATCGGCGGTCCTCCAAACGGCGGAGTCTCCACCGTTCA
AAACACAAGTCCACTTCACTCCACCACCGTCAGCCCTGCGACGCGACTCTTGGCCGTTACCTAGCAAGACGGT
TAGTCGAAATCGGCGTCACCGATGTCTTCTCCGTTCCTGGTGATTTCAACCTGACGCTTCTCGATCACCTAATC
GCCGAACCAAACCTCAAGCTGATCGGTTGCTGCAACGAGCTTAACGCCGGATACGCTGCTGACGGTTACGCTAG
ATCTCGCGGTGTTGGTGCGTGCGTCGTTACGTTCACCGTCGGTGGATTGAGTGTTCTGAATGCGATCGCCGGTG
CTTACAGTGAGAATCTGCCTCTGATTTGCATCGTCGGTGGTCCAAACTCCAACGATTACGGTACCAATAGGATT
CTTCATCATACAATTGGTTTACCTGATTTCACTCAAGAGCTTAGGTGTTTTCAAGCTGTTACTTGTTTTCAAGC
TGTGATTAATAACTTAGAAGAGGCTCATGAACTTATCGATACTGCGATTTCAACTGCTTTGAAAGAAAGCAAAC
CTGTTTATATCAGTATCAGCTGTAATTTACCGGCGATTCCTCTTCCGACGTTAGTCGTCATCCTGTTCCGTTC
ATGCTTCCGATGAAGGTTAGCAATCAGATTGGTTTAGATGCGGCGGTGGAGGCAGCTGCTGAGTTCTTGAACAA
AGCTGTGAAGCCAGTTCTTGTTGGTGGGCCGAAAATGCGGGTTGCGAAAGCCGCGGATGCTTTTGTTGAGCTTG
CTGATGCTTCTGGCTATGGTCTTGCTGTGATGCCTTCTGCTAAAGGACAAGTACCTGAGCATCACAAGCATTTT
ATAGGGACGTATTGGGGAGCTGTGAGTACAGCTTTTTGTGCTGAAATCGTTGAATCTGCGGATGCTTATCTGTT
TGCAGGTCCGATTTTCAACGATTACAGTTCTGGTGGGTATTCTCTGCTTCTCAAGAAGGAGAAGGCAATCATCG
TTCAGCCTGATCGGGTTACTATCGGTAACGGACCTGCGTTTGGATGTGTTCTTATGAAGGATTTTCTAAGCGAG
TTGGCTAAACGAATTAAGCACAACAACACTTCTTATGAGAATTATCACAGGATCTATGTCCCAGAAGGAAAGCC
TTTGAGAGATAACCCGAATGAGTCTTTGAGGGTTAATGTACTGTTCCAACACATTCAGAATATGCTCTCTTCTG
AGTCTGCTGTGCTTGCTGAGACAGGAGATTCCTGGTTCAACTGTCAGAAGCTGAAGCTCCCTGAAGGATGCGGT
TACGAATTCCAAATGCAGTACGGATCAATTGGCTGGTCAGTGGGTGCTACTCTAGGCTATGCTCAAGCCATGCC
AAACAGGCGTGTCATTGCTTGTATTGGAGATGGTAGTTTGCAGGTAACCGCGCAGGATGTATCTACGATGATAC
GGTGTGGGCAAAAGACCATAATCTTCCTCATCAACAACGGAGGCTACACCATTGAGGTGGAAATTCACGATGGT
CCTTACAATGTCATAAAGAACTGGAACTACACAGCTTTTGTTGAGGCCATACACAATGGAGAAGGAAAATGCTG
GACTGCCAAGGTGAGATGCGAGGAGGAGTTAGTGAAAGCAATCAACACGGCAACCAATGAGGAAAAAGAGAGCT
TTTGTTTCATTGAAGTGATAGTGCACAAAGACGATACAAGCAAGGAACTTTTGGAGTGGGGCTCTAGAGTCTCT
GCTGCTAATAGTCGTCCCCCAAATCCGCAGTAGAGTATATAAATGCACTCAACTTATATATATTTCAGATTTGG
TAGTGTCTTCACCGTTCTATGTAAAGTAGTGTGGATCCTTTTACACCCATCTGGATGGGAAAAAAATGTGTGTC
CCCTTGAGGATATAAACTG                                      [SEQ ID NO: 17]
```

FIG. 9A

```
  1 MDTKIGSIDA CNPTNHDIGG PPNGGVSTVQ NTSPLHSTTV SPCDATLGRY
 51 LARRLVEIGV TDVFSVPGDF NLTLLDHLIA EPNLKLIGCC NELNAGYAAD
101 GYARSRGVGA CVVTFTVGGL SVLNAIAGAY SENLPLICIV GGPNSNDYGT
151 NRILHHTIGL PDFTQELRCF QAVTCFQAVI NNLEEAHELI DTAISTALKE
201 SKPVYISISC NLPAIPLPTF SRHPVPFMLP MKVSNQIGLD AAVEAAAEFL
251 NKAVKPVLVG GPKMRVAKAA DAFVELADAS GYGLAVMPSA KGQVPEHHKH
301 FIGTYWGAVS TAFCAEIVES ADAYLFAGPI FNDYSSGGYS LLLKKEKAII
351 VQPDRVTIGN GPAFGCVLMK DFLSELAKRI KHNNTSYENY HRIYVPEGKP
401 LRDNPNESLR VNVLFQHIQN MLSSESAVLA ETGDSWFNCQ KLKLPEGCGY
451 EFQMQYGSIG WSVGATLGYA QAMPNRRVIA CIGDGSLQVT AQDVSTMIRC
501 GQKTIIFLIN NGGYTIEVEI HDGPYNVIKN WNYTAFVEAI HNGEGKCWTA
551 KVRCEEELVK AINTATNEEK ESFCFIEVIV HKDDTSKELL EWGSRVSAAN
601 SRPPNPQ                                      [SEQ ID NO: 18]
```

FIG. 9B

```
GAGAGAAGAGGAGGAGAATTCGAAGAATAAAAGATAAGAACTTTGACGTTTTGAAGCTTAAAGCTTGAAACTTG
TTTCATCCATGGCGGCTCGTAGAGTGTCTTCTCTTTTATCTCGATCTTTTTCAGCTTCCTCTCCCTTACTGTTT
CGTTCTCAAGGGAGAAATTGTTACAATGGAGGGATCTTAAGGAGATTTGGAACCTCTTCTGCTGCTGCTGAGGA
AATCATAAACCCATCTGTTCAAGTTTCTCACACACAGCTCCTCATCAATGGGAACTTTGTTGACTCTGCTTCTG
GTAAGACGTTTCCGACTCTTGATCCGAGGACAGGCGAAGTCATTGCTCATGTAGCTGAAGGCGATGCTGAAGAT
ATCAATCGAGCTGTGAAAGCTGCAAGGACGGCCTTTGATGAAGGACCTTGGCCTAAAATGAGTGCTTATGAAAG
GTCAAGAGTTTTGTTGAGGTTTGCAGATTTGGTTGAGAAACACAGCCAAGAGCTCGCGTCTCTAGAGACATGGG
ACAATGGCAAGCCTTACCAACAATCCTTGACCGCAGAGATTCCCATGTTTGCAAGATTGTTCCGTTACTATGCT
GGATGGGCGGATAAGATTCATGGACTAACAATTCCAGCTGATGGAAACTATCAAGTTCACACATTACATGAACC
GATAGGTGTAGCTGGACAGATCATACCGTGGAATTTTCCACTTTTGATGTTTGCTTGGAAAGTTGGTCCTGCTC
TTGCTTGTGGTAACACCATTGTCCTCAAAACCGCTGAGCAAACACCTCTCACGGCTTTCTATGCTGGAAAGCTT
TTCCTTGAAGCGGGTCTTCCTCCTGGTGTTCTGAATATTGTTTCGGGATTCGGTGCAACAGCAGGTGCTGCCCT
CGCGAGTCATATGGATGTAGACAAGCTTGCTTTTACAGGATCGACTGATACGGGGAAAGTTATACTTGGATTGG
CTGCTAACAGCAATCTTAAGCCCGTAACTCTGGAACTTGGAGGGAAATCACCGTTCATCGTATTCGAAGATGCT
GATATTGATAAAGCTGTAGAGCTTGCACACTTTGCCCTCTTCTTCAACCAGGGGCAATGTTGCTGCGCGGGGTC
TCGGACATTTGTTCATGAGAAAGTGTATGATGAGTTTGTTGAGAAATCAAAGGCACGCGCATTGAAACGTGTTG
TTGGTGATCCTTTCAGGAAAGGCATTGAACAGGGTCCTCAGATCGATTTGAAGCAATTTGAGAAAGTGATGAAG
TACATAAAGTCAGGTATCGAAAGCAATGCTACTCTTGAATGTGGTGGTGATCAGATTGGAGACAAAGGTTACTT
CATCCAACCTACTGTCTTCTCTAATGTTAAGGATGACATGCTTATCGCTCAAGACGAGATTTTCGGTCCAGTCC
AATCGATCTTGAAGTTCAGTGATGTGGATGAGGTGATAAAGAGGGCGAACGAGACGAAGTACGGGCTAGCGGCA
GGGGTTTTCACGAAGAATCTGGACACGGCAAACAGGGTTTCAAGGGCTTTGAAAGCTGGTACCGTATGGGTTAA
CTGCTTCGACGTATTTGATGCAGCCATACCATTTGGTGGTTACAAGATGAGTGGGAATGGGAGAGAGAAAGGCA
TATACAGTCTCAATAATTACTTGCAGATCAAGGCAGTCGTCACTGCTCTAAATAAGCCTGCCTGGATCTGATCT
CTGGAGTGTGGTTTCAGCATCATAAATGCTCAAACAAAAGAAATAGACTCTATAAAGTTACAATAGTAATAATT
AAGGTCATGGTTTGTAATTTGAGTAACGGATTGTGATACTTCTAATAAATTTTTCATTGTTGTTTATTCATCAA
AAAAAAAAAAAA                                                    [SEQ ID NO:19]
```

FIG. 10A

```
  1  MAARRVSSLL SRSFSASSPL LFRSQGRNCY NGGILRRFGT SSAAAEEIIN
 51  PSVQVSHTQL LINGNFVDSA SGKTFPTLDP RTGEVIAHVA EGDAEDINRA
101  VKAARTAFDE GPWPKMSAYE RSRVLLRFAD LVEKHSEELA SLETWDNGKP
151  YQQSLTAEIP MFARLFRYYA GWADKIHGLT IPADGNYQVH TLHEPIGVAG
201  QIIPWNFPLL MFAWKVGPAL ACGNTIVLKT AEQTPLTAFY AGKLFLEAGL
251  PPGVLNIVSG FGATAGAALA SHMDVDKLAF TGSTDTGKVI LGLAANSNLK
301  PVTLELGGKS PFIVFEDADI DKAVELAHFA LFFNQGQCCC AGSRTFVHEK
351  VYDEFVEKSK ARALKRVVGD PFRKGIEQGP QIDLKQFEKV MKYIKSGIES
401  NATLECGGDQ IGDKGYFIQP TVFSNVKDDM LIAQDEIFGP VQSILKFSDV
451  DEVIKRANET KYGLAAGVFT KNLDTANRVS RALKAGTVWV NCFDVFDAAI
501  PFGGYKMSGN GREKGIYSLN NYLQIKAVVT ALNKPAWI
                                                  [SEQ ID NO: 20]
```

FIG. 10B

```
AGAGAGAGAGAGAGAAATACAAAGAAAAATAAATGGAGAACGGCAAATGCAACGGAGCCACGACGGTGAAGTTA
CCGGAGATCAAATTCACCAAGCTTTTCATCAACGGCCAGTTCATTGATGCTGCTTCAGGGAAGACGTTTGAGAC
GATAGACCCTAGGAACGGTGAAGTGATCGCAACAATAGCCGAAGGAGACAAAGAAGACGTTGACTTGGCCGTTA
ACGCTGCACGTTACGCCTTCGACCATGGTCCTTGGCCTCGCATGACCGGCTTCGAGAGGGCAAAGCTTATAAAC
AAATTCGCAGACTTAATAGAGGAAAACATTGAAGAATTGGCTAAACTTGATGCGGTTGACGGTGGAAAATTGTT
CCAATTGGGGAAATATGCTGATATTCCGGCCACAGCCGGTCATTTTCGATACAATGCGGGTGCAGCGGATAAAA
TCCACGGCGAGACTCTTAAAATGACGCGTCAATCGTTGTTTGGATACACCCTCAAAGAACCAATTGGAGTGGTT
GGTAATATCATCCCTTGGAATTTCCCAAGCATTATGTTTGCCACAAAGGTAGCTCCGGCTATGGCTGCTGGTTG
CACCATGGTGGTCAAGCCAGCTGAACAGACTTCACTCTCTGCTTTGTTCTATGCCCATCTCTCAAAAGAAGCGG
GAATTCCTGATGGTGTGCTCAACATTGTAACTGGTTTTGGATCAACTGCTGGAGCTGCCATTGCCTCCCATATG
GACGTAGACAAAGTTAGTTTCACTGGGTCAACAGATGTTGGAAGGAAGATAATGCAAGCCGCAGCCGCAAGTAA
TCTCAAAAAAGTTTCCCTTGAATTAGGCGGGAAATCGCCACTTCTCATATTCAACGACGCTGATATTGACAAAG
CCGCCGATCTTGCGCTTCTCGGTTGCTTTTACAACAAGGGTGAAATTTGCGTGGCGAGCTCTCGTGTGTTTGTT
CAAGAAGGTATATACGATAAGGTTGTGGAGAAGTTAGTAGAGAAGGCTAAAGATTGGACCGTTGGTGATCCTTT
TGATTCCACTGCTCGACAAGGACCTCAAGTGGATAAAAGACAGTTTGAGAAGATTCTATCTTACATTGAGCACG
GTAAAAACGAAGGAGCGACCTTATTAACTGGAGGAAAAGCCATTGGAGACAAAGGATATTTCATCCAACCAACT
ATATTCGCAGATGTCACTGAGGATATGAAGATATACCAAGATGAAATCTTTGGACCAGTCATGTCACTGATGAA
ATTCAAGACGGTAGAGGAAGGGATCAAATGCGCAAACAACACGAAATACGGTCTTGCAGCAGGAATACTAAGCC
AAGACATAGACTTGATCAACACGGTTTCGAGGTCAATCAAAGCTGGAATCATTTGGGTTAATTGCTACTTCGGG
TTTGATCTTGACTGTCCTTATGGTGGCTACAAGATGAGTGGTAATTGTCGTGAAAGTGGCATGGACGCTCTCGA
CAACTATCTACAAACCAAATCCGTCGTTATGCCTCTTCACAATTCCCCTTGGATGTAATAAAATTGTCCATAAC
ACATAGAAAAAAACTTAATCCAATGATAATAAGGCGGCTTGAATTAAAAAAAAAAAAAAA
```
[SEQ ID NO: 21]

FIG. 11A

```
  1  MENGKCNGAT  TVKLPEIKFT  KLFINGQFID  AASGKTFETI  DPRNGEVIAT
 51  IAEGDKEDVD  LAVNAARYAF  DHGPWPRMTG  FERAKLINKF  ADLIEENIEE
101  LAKLDAVDGG  KLFQLGKYAD  IPATAGHFRY  NAGAADKIHG  ETLKMTRQSL
151  FGYTLKEPIG  VVGNIIPWNF  PSIMFATKVA  PAMAAGCTMV  VKPAEQTSLS
201  ALFYAHLSKE  AGIPDGVLNI  VTGFGSTAGA  AIASHMDVDK  VSFTGSTDVG
251  RKIMQAAAAS  NLKKVSLELG  GKSPLLIFND  ADIDKAADLA  LLGCFYNKGE
301  ICVASSRVFV  QEGIYDKVVE  KLVEKAKDWT  VGDPFDSTAR  QGPQVDKRQF
351  EKILSYIEHG  KNEGATLLTG  GKAIGDKGYF  IQPTIFADVT  EDMKIYQDEI
401  FGPVMSLMKF  KTVEEGIKCA  NNTKYGLAAG  ILSQDIDLIN  TVSRSIKAGI
451  IWVNCYFGFD  LDCPYGGYKM  SGNCRESGMD  ALDNYLQTKS  VVMPLHNSPW
501  M
```
[SEQ ID NO: 22]

FIG. 11B

```
CAAAAAAGTTAGCCATGGCATCAAGAAGAGTTTCTTCGCTGCTCTCTCGCTCTTTCATGTCCTCCTCACGTTCT
ATCTTCTCTCTTAGAGGCATGAACAGAGGAGCTCAAAGATACAGTAACCTCGCTGCTGCTGTCGAAAACACTAT
TACTCCACCAGTGAAAGTTGAACACACACAGCTTCTAATCGGTGGAAGATTCGTTGATGCAGTGTCAGGAAAAA
CTTTCCCTACTTTGGATCCAAGAAATGGAGAAGTGATTGCTCAAGTGTCTGAAGGTGATGCAGAAGACGTGAAC
CGCGCGGTTGCAGCTGCACGAAAGGCTTTTGATGAAGGACCATGGCCTAAAATGACAGCTTATGAGAGATCAAA
GATACTGTTTCGTTTCGCTGATTTAATCGAGAAACATAATGATGAGATTGCTGCTCTTGAGACTTGGGATAATG
GGAAACCTTATGAACAATCTGCTCAAATTGAAGTACCAATGCTTGCTAGGGTGTTCCGGTACTATGCTGGTTGG
GCAGACAAGATACATGGAATGACAATGCCAGGAGATGGTCCACACCATGTGCAGACCTTACATGAGCCTATAGG
AGTCGCTGGACAAATCATCCCATGGAACTTCCCTCTTCTCATGCTTTCTTGGAAACTTGGACCAGCTTTAGCTT
GCGGTAACACCGTTGTTCTCAAAACTGCTGAGCAAACTCCTCTATCTGCTCTTCTTGTTGGGAAACTACTTCAT
GAGGCTGGACTTCCTGATGGAGTTGTGAATATAGTTTCTGGATTTGGGGCTACTGCTGGTGCAGCTATAGCTAG
TCACATGGACGTTGATAAGGTTGCTTTCACCGGGTCTACTGATGTTGGGAAGATTATTCTTGAGTTAGCTTCAA
AAAGCAACCTTAAGGCAGTGACTCTTGAGCTGGAGGAAAGTCACCATTCATTTGTATGTGAAGATGCTGATGTG
GATCAGGCCGTTGAGCTTGCACATTTCGCTTTGTTCTTTAACCAGGGACAATGTTGTTGTGCTGGTTCGCGTAC
ATTTGTACATGAACGTGTGTATGATGAGTTTGTAGAGAAAGCTAAAGCTCGTGCACTCAAGCGAAATGTTGGAG
ATCCCTTCAAGTCAGGCATTGAGCAAGGTCCCCAGGTAGACTCAGAGCAATTCAACAAAATCCTGAAGTACATC
AAACATGGAGTTGAGGCTGGAGCCACATTACAAGCTGGAGGTGACAGGCTTGGTTCCAAGGGTTACTACATTCA
ACCTACTGTCTTCTCAGATGTGAAAGATGACATGCTCATAGCAACAGACGAGATTTTCGGGCCGGTTCAAACCA
TACTGAAATTCAAGGATCTTGATGAGGTGATTGCAAGGGCCAACAACTCAAGGTACGGTTTAGCTGCTGGAGTG
TTCACACAGAATCTTGACACAGCACACCGGCTGATGCGAGCACTCAGAGTTGGGACTGTTTGGATCAACTGTTT
TGATGTACTTGATGCATCAATTCCATTTGGAGGGTATAAGATGAGTGGCATTGGTAGAGAGAAAGGTATCTACA
GTCTCAACAATTACTTGCAAGTCAAGGCTGTTGTTACTTCCTCAAGAACCCTGCCTGGCTCTAAACCATACCA
GGTGGTTACACTTATTTCTCGAGTTTGGTTTATGATTTGCACTTTTGCTTTGAAAACCTGGAGTTGTACTGTGT
CTCTAGGATTTCTAGATTTTGAGAGTAATTTATCTTCAATACATTTGCAATAAAGCTACATGACAATGG
                                                                [SEQ ID NO: 23]
```

FIG. 12A

```
  1  MASRRVSSLL SRSFMSSSRS IFSLRGMNRG AQRYSNLAAA VENTITPPVK
 51  VEHTQLLIGG RFVDAVSGKT FPTLDPRNGE VIAQVSEGDA EDVNRAVAAA
101  RKAFDEGPWP KMTAYERSKI LFRFADLIEK HNDEIAALET WDNGKPYEQS
151  AQIEVPMLAR VFRYYAGWAD KIHGMTMPGD GPHHVQTLHE PIGVAGQIIP
201  WNFPLLMLSW KLGPALACGN TVVLKTAEQT PLSALLVGKL LHEAGLPDGV
251  VNIVSGFGAT AGAAIASHMD VDKVAFTGST DVGKIILELA SKSNLKAVTL
301  ELEESHHSFV CEDADVDQAV ELAHFALFFN QGQCCAGSR  TFVHERVYDE
351  FVEKAKARAL KRNVGDPFKS GIEQGPQVDS EQFNKILKYI KHGVEAGATL
401  QAGGDRLGSK GYYIQPTVFS DVKDDMLIAT DEIFGPVQTI LKFKDLDEVI
451  ARANNSRYGL AAGVFTQNLD TAHRLMRALR VGTVWINCFD VLDASIPFGG
501  YKMSGIGREK GIYSLNNYLQ VKAVVTSLKN PAWL  [SEQ ID NO: 24]
```

FIG. 12B

```
AACAAACAAGGTCTAGCTTTTTATAACCAAACTCTGCTTCTGAACAGAGTTAGTCAAAGAGAGAGAAGCCATGG
AAGCTATGAAGGAGACTGTGGAGGAGAGCTTGAGAGAGATGAGAGAGACGTTTGCGAGTGGGAGGACGAGGAGT
CTGAAGTGGAGGAAGGCACAGATCGGAGCTATATACGAGATGGTTAAAGACAACGAAGACAAGATCTGCAATGC
TCTGTTTCAAGATTTGGGCAAACACAGTACTGAAGCTTTTAGAGATGAGCTTGGTGTTGTCTTGCGAACAGCTA
CTGTTGCAATCAACTGTCTTGATAAATGGGCCGTCCCCAAACATAGCAAACTTCCTCTGTTGTTCTACCCAGCA
AAAGGGAAAGTCATATCGGAACCCTATGGACGGTTCTTGTTCTGTCTAGCTGGAATTTTCCTATATCTTTGTC
TCTGGATCCATTGATTGGGGCAATAGCAGCAGGAAATACCGTGCTTCTCAAGTCATCTGAACTAAGCCCTAACG
CATCTGCCTTCCTGCCAAGACAATTCCAGCTTATCTCGATACTAAAGCCATCAAAGTTATCGAAGGAGGACCT
GATGTCGCTACTATCCTCTTGCAGCATCAATGGGACAAGATCTTCTTCACCGGGAGTCCCAAGATTGGAAGGAT
CATAATGGCTGCAGCAGCACAGCATCTGACTCCTGTGACATTGGAGCTTGGTGGAAAATGTCCCACCATTGTTG
ATCATCACACCATTTCAAAGAACATCAAGTCGGTTGTCAAGAGGATTGCTGGAGGAAAATGGGGATCTTGCAAT
GGACAAGCTTGTATCTCTGTAGATTACGTTCTTATCGAAAAGAGTTTCGCGCCTACTCTGATTGATATGTTGAA
GCCTACGATAAAGTCTTTCTTTGGCGAAAATCCTAAAGAATCTGGATGTCTCTCAAGGATTGCAAACAAGCACC
ACGTTCAGAGACTGTCTCGTCTTCTTAGCGATCCTCGTGTCCAAGCTTCCATCGTCTATGGTGGTTCTATAGAC
GAAGATAAGCTGTATGTTGAGCCAACGATCTTGTTGGACCCTCCTCTTGATTCTGAGATCATGAATGAAGAGAT
CTTTGGTCCAATTCTCCCGATTATCACGGTACGTGACATCCAAGAAAGCATAGGGATCATTAATACAAAACCGA
AGCCACTTGCCATTTATGCATTCACAAATGACGAGAACCTTAAAACTAGAATTTTGTCAGAAACATCCTCAGGA
AGTGTTACCTTCAATGACGTCATGATCCAGTATATGTGTGATGCGTTACCTTTTGGAGGAGTGGGAGAAAGTGG
AATAGGGAGGTATCACGGGAAATACTCATTTGATTGTTTCAGTCACGAGAAAGCAATAATGGAAGGAAGCTTAG
GTATGGATCTTGAAGCTCGATACCCTCCATGGAACAACTTCAAGCTCACCTTCATCAGACTCGCATTTCGTGAA
GCTTACTTCAAGCTTATCCTCCTTATGCTTGGTCTTAAAAGATAAAAGGGGGAAAGTGAGAGACAGAGACACAT
ACACACAAACAGAGACAATATAAGTGATTGAATTACATCACACTTATGTTTGCTTATCATATCTTCACCTAATA
AGTCTCATTCCGAATGTTTTACATTTCTTTCAAGCTTGAGAGATTCTATATAAAGTGATTTGATATCTAAAAAA
AAAAAAAAAAAAAAA                                                        [SEQ ID NO: 25]
```

```
  1 MEAMKETVEE SLREMRETFA SGRTRSLKWR KAQIGAIYEM VKDNEDKICN
 51 ALFQDLGKHS TEAFRDELGV VLRTATVAIN CLDKWAVPKH SKLPLLFYPA
101 KGKVISEPYG TVLVLSSWNF PISLSLDPLI GAIAAGNTVL LKSSELSPNA
151 SAFLAKTIPA YLDTKAIKVI EGGPDVATIL LQHQWDKIFF TGSPKIGRII
201 MAAAAQHLTP VTLELGGKSC ISVDYVLIEK SFAPTLIDML KPTIKSFFGE
251 NPKESGCLSR IANKHHVQRL SRLLSDPRPT ILLDPPLDSE IMNEEIFGPI
301 LPIITVRDIQ ESIGIINTKP KPLAIYAFTN DENLKTRILS ETSSGSVTFN
351 DVMIQYMCDA LPFGGVGESG IGRYHGKYSF DCFSHEKAIM EGSLGMDLEA
401 RYPPWNNFKL TFIRLAFREA YFKLILLMLG LKR       [SEQ ID NO: 26]
```

FIG. 13

```
   1 aaactccgcc tccgtttgtt ggctatttac actcactctg tctccgccgg tagatttgtc
  61 agctgcgtct tcctcgtttt ctctctctct gtctgtgtct cttagaatgc aatcagctat
 121 ggcgctttcg ttctcccaga cgtcgtttac aagaccaaac cacgtgctcg gatcatctgg
 181 ttctgttttc tctacgccca gaagtctccg gttctgcgga ctccggcggg aagcgtttgg
 241 tttctcaacg tcgaatcagt tggctattcg cagtaaccga atccaatttc taagtaggaa
 301 gtcattccaa gtctccgctt ctgcttcaag taatggtaat ggcgctccac cgaaatcttt
 361 cgattacgat ttgatcatca tcggagctgg agttggtggc cacggagctg ctttgcacgc
 421 cgttgaaaag ggacttaaaa cagccattat tgaaggagat gttgttggag ggacttgtgt
 481 taacagagga tgtgtgcctt ctaaagctct tcttgctgtt agtggtcgaa tgcgggaact
 541 tcagaacgaa catcacatga agtcctttgg tctccaggtt tcagctgctg gatatgatcg
 601 tcagggtgtg gcagatcatg ctaataatct ggctaccaaa atacgaaaca atctgaccaa
 661 ttcaatgaag gcaattggtg ttgacatatt gactggattt ggcagtgttc tgggtccaca
 721 aaaggttaaa tatgggaagg acaatattat tactgcaaaa gatataatca ttgccactgg
 781 atctgtgccg tttgtcccta aaggaattga agttgatgga agactgtga tcaccagtga
 841 ccatgctttg aaattagagt ctgtccctga gtggattgca attgtaggaa gtggttatat
 901 tggtcttgag ttcagtgatg tttacacagc tcttggaagt gaggtaactt ttatagaagc
 961 actggatcag ctaatgcctg gatttgatcc tgagatcagt aagctagctc agagggtttt
1021 gataaatcca agaaagattg actatcatac tggagtcttt gcaagcaaaa ttactccggc
1081 aagggatggg aaaccagttc tgattgagct tattgatgcc aaaaccaagg aacctaagga
1141 tactttggag gtagatgctg ctcttattgc tactgggaga gctccattca ccaatggact
1201 tggcttggaa aatgtcaatg ttgtgacgca gagaggttc ataccagttg atgagcgaat
1261 gcgtgtgatc gatggaaagg ggactctggt tccgaacttg tactgcattg gtgatgccaa
1321 tggtaaattg atgcttgcac atgcagccag tgcccaagga atttctgtgg tcgagcaagt
1381 cagcggcaga gatcatgtgc ttaatcatct tagcatccca gctgcttgct ttactcatcc
1441 tgaaatcagc atggtgggat taacagagcc tcaagcaaaa gaaaaaggcg agaaggaagg
1501 atttaaagtt agtgttgtca agacaagttt caaggctaac acaaaggccc tagctgaaaa
1561 tgaaggagaa ggaatagcta agatgatata ccgacctgac aatggtgaaa tcttaggagt
1621 tcatatattt ggactgcatg cagctgacct tatccatgaa gcttctaatg cgattgctct
1681 aggaacgcgt attcaggaca taaaattggc agttcatgca catccaacac tctctgaggt
1741 cctcgacgaa ctgttcaaag cagccaaggt tgaaagtcat gctacgacaa ggacagtaag
1801 tgaaaaagtg gttgtataat aagaaaccaa aaacttattg gggtggggag aaacatcttg
1861 aagaaagaaa atttgtgatt gtactttagg gagatgcaaa gataaagcta aacacgaacc
1921 aggaagatcg aaaaggaaga agaagaggag gagatgatga gaaacaacct tccgtaagta
1981 aagacttgaa agatatatct acaaggcctt cttctttctt tgagaatatt tctgttggag
2041 tcttgtctct gctttcactt atatttgttt aattgttcca tggtttcaat tagtggagat
2101 tgtggttttg gttattgtat gtttgtttga tgtgaacgat tttggatgat tcttctcttt
2161 ttactagtaa aatcacttgt ctgtcaaaaa aaaaaaaaaa aaaaa [SEQ ID NO: 27]
```

```
  1 M Q S A M A L S F S Q T S F T R P N H V L G S S G S V F S T
 31 P R S L R F C G L R R E A F G F S T S N Q L A I R S N R I Q
 61 F L S R K S F Q V S A S A S S N G N G A P P K S F D Y D L I
 91 I I G A G V G G H G A A L H A V E K G L K T A I I E G D V V
121 G G T C V N R G C V P S K A L L A V S G R M R E L Q N E H H
151 M K S F G L Q V S A A G Y D R Q G V A D H A N N L A T K I R
181 N N L T N S M K A I G V D I L T G F G S V L G P Q K V K Y G
211 K D N I I T A K D I I I A T G S V P F V P K G I E V D G K T
241 V I T S D H A L K L E S V P E W I A I V G S G Y I G L E F S
271 D V Y T A L G S E V T F I E A L D Q L M P G F D P E I S K L
301 A Q R V L I N P R K I D Y H T G V F A S K I T P A R D G K P
331 V L I E L I D A K T E P K D T L E V D A A L I A T G R A P
361 F T N G L G L E N V N V V T Q R G F I P V D E R M R V I D G
391 K G T L V P N L Y C I G D A N G K L M L A H A A S A Q G I S
421 V V E Q V S G R D H V L N H L S I P A A C F T H P E I S M V
451 G L T E P Q A K E K G E K E G F K V S V V K T S F K A N T K
481 A L A E N E G E G I A K M I Y R P D N G E I L G V H I F G L
511 H A A D L I H E A S N A I A L G T R I Q D I K L A V H A H P
541 T L S E V L D E L F K A A K V E S H A T T R T V S E K V V V
                                                    [SEQ ID NO: 28]
```

FIG. 14

```
   1 cacacgtgtc ggagtctgcc gttttgaactg ttcgccgttc tccttcccca cgtggctctc
  61 acaagataac gtcaggcaga ccgagaaata aaaggcccaa tgggctcaga gttggatatt
 121 atagccggga attttgaaat ctccggttta aagacgagaa acgtgacacg tgtcatctcc
 181 gctttgatat ctccgcctcc gctcgtcgag tgagactagt acagacttgt catctccgtc
 241 actccctttt tctctacaca gatctctcat tcactctctc gtacacaatg caatcggttc
 301 tttctctttc cttctcacaa gcatcgcttc ctttagcgaa tcgtacgctt tgttcatcca
 361 acgcagctcc ttctacgccg agaaatctcc ggttctgtgg actccggcga gaagcgtttt
 421 gcttctctcc gtcgaagcaa ttgacctcgt gccgtttcca tattcagagt aggagaatcg
 481 aagtctccgc cgctgcttct tcttccgctg gaaatggagc tccatcgaaa tcattcgatt
 541 atgatttgat cattatcgga gctggagttg gtggccatgg agctgcattg cacgccgtcg
 601 agaagggact caaagctggc atcattgaag gagatgttgt tggaggtact tgcgttaaca
 661 gaggctgtgt gccttccaaa gctctacttg ctgttagtgg taggatgagg aactccaga
 721 acgaacatca catgaaggct tttggtttgc aggtttcagc tgctggttat gaccgccaag
 781 gtgtggctga ccacgcaagt aacctggcta ccaaaattag gaataatctc accaattcta
 841 tgaaggcact tggtgttgac atattgacag ggtttggcgc tgttctgggc ccacaaaagg
 901 ttaaatatgg tgacaatatt atcaccggaa aagatataat catcgcaact ggatctgtac
 961 cgttcgtccc gaaggaatt gaagttgatg gaaagactgt tatcacaagt gatcatgcat
1021 tgaaattgga gtccgttcct gactggattg cgatagtagg aagtggttat atcggtcttg
1081 agttcagtga tgtttacacg gcccttggaa gtgaggcaac ttttattgag gcactggatc
1141 aactaatgcc tggatttgat cctgagatca gtaagctggc tcaaagggtt ctaataaata
1201 caagaaaaat tgactaccat actggagtat ttgcaagcaa aatcactcca gcaaaggatg
1261 ggaaaccagt gctgattgaa ctaattgatg ccaaaaccaa ggaacccaag gatactttgg
1321 aggttgacgc tgctctaatt gctactggaa gagctccatt caccaatggt cttggcctgg
1381 aaaatatcaa tgttaccaca caaagaggtt ttataccagt tgatgagcga atgcgtgtta
1441 ttgatggaaa tggaaagctg gttccccact tgtactgcat cggtgatgcc aatggtaaac
1501 tgatgcttgc tcatgcagct agtgctcaag gaatttctgt ggtggagcaa gtcacaggta
1561 gagatcatgt gcttaatcat cttagcatcc cagctgcttg ttttactcat cctgaaataa
1621 gtatggtggg attgacagag cctcaagcga gagagaaagc tgagaaagag ggattcaaag
1681 taagtatcgc caagacaagt ttcaaggcaa acacaaaggc cctagccgaa aatgaaggag
1741 aaggactcgc taagatgata tacagacctg acaatggtga atccttgga gttcatatat
1801 ttggattgca tgctgctgat cttatccatg aagcatcaaa cgcgattgct ttaggaacac
1861 gtattcagga cataaaactt gctgttcatg cacatccaac actgtctgaa gttgtagacg
1921 aactgtttaa agcagccaag gtcgatagtc cagcttcagt aacagcacaa agtgtgaaag
1981 ttactgtgta aacatgaaga atttaagagc agcctgtaac aaaagttttg tggaaaagac
2041 atttgtactt caccaatatt catcaaagga cgaagattgc gtctctaaaa aaaaaaaaaa
2101 aaaaaaaaaa aaaaaaaaaa                            [SEQ ID NO: 29]
```

```
   1 M Q S V L S L S F S Q A S L P L A N R T L C S S N A A P S T
  31 P R N L R F C G L R R E A F C F S P S K Q L T S C R F H I Q
  61 S R R I E V S A A A S S S A G N G A P S K S F D Y D L I I I
  91 G A G V G G H G A A L H A V E K G L K T A I I E G D V V G G
 121 T C V N R G C V P S K A L L A V S G R M R E L Q N E H H M K
 151 A F G L Q V S A A G Y D R Q G V A D H A S N L A T K I R N N
 181 L T N S M K A L G V D I L T G F G A V L G P Q K V K Y G D N
 211 I I T G K D I I I A T G S V P F V P K G I E V D G K T V I T
 241 S D H A L K L E S V P D W I A I V G S G Y I G L E F S D V Y
 271 T A L G S E V T F I E A L D Q L M P G F D P E I S K L A Q R
 301 V L I N T R K I D Y H T G V F A S K I T P A K D G K P V L I
 331 E L I D A K T K E P K D T L E V D A A L I A T G R A P F T N
 361 G L G L E N I N V T T Q R G F I P V D E R M R V I D G N G K
 391 L V P H L Y C I G D A N G K L M L A H A A S A Q G I S V V E
 421 Q V T G R D H V L N H L S I P A A C F T H P E I S M V G L T
 451 E P Q A R E K A E K E G F K V S I A K T S F K A N T K A L A
 481 E N E G E G L A K M I Y R P D N G E I L G V H I F G L H A A
 511 D L I H E A S N A I A L G T R I Q D I K L A V H A H P T L S
 541 E V V D E L F K A A K V D S P A S V T A Q S V K V T V
                                                   [SEQ ID NO: 30]
```

FIG. 15

SEQUENCE LISTING

```
<160> NUMBER OF SEQ ID NOS:  38

<210> SEQ ID NO 1
<211> LENGTH: 2382
<212> TYPE: DNA
<213> ORGANISM: Arabidopsis Thaliana
<220> FEATURE:
<221> NAME/KEY: old_sequence
<222> LOCATION: (422)
<223> OTHER INFORMATION: originally "n"

<400> SEQUENCE: 1
tcaaagatca tccccatcgg agaatcttct cctccatagg aaaatgtcgt ctaattccct      60
gaggcatgtc gagtccatgt cccagctacc ctcaggtgcc ggaaagatct ctcaattaaa     120
cgccgtcgtg ttaggagaat cccttgcatc ggaggagaat gatctcgtct ttcccagcaa     180
ggaattctcc ggccaggctc ttgtttcctc ccctcaacag tacatggaaa tgcataagag     240
gtcgatggat gaccctgctg cttttttggtc tgatattgcg tctgagtttt actggaagca     300
gaaatggggt gaccaagtgt tttccgagaa tctcgatgtc aggaagggtc ctattagcat     360
```

```
cgagtggttt aaaggggaa tcaccaatat ttgctacaac tgtttggaca aaaacgttga      420
agctggtttg ggcgataaga cagccataca ctgggaagga aatgaacttg ggtagatgc      480 ttccttaact tattctgagt tgctccaacg agtttgccag cttgctaatt acttgaaaga    540
taatggagtg aagaagggtg atgctgttgt aatttattta cctatgttga tggaacttcc    600
catcgctatg cttgcatgtg caaggatcgg agctgttcat tcggtcgtat ttgctggatt    660
ttctgcggac tctcttgccc aaagaatcgt tgattgcaag ccaaatgtaa tactgacttg    720
caatgctgtt aaaagaggcc ctaagaccat aaaccttaaa gctattgttg atgctgcact    780
tgaccaatct tctaaagatg gagtctctgt aggcatatgc ttgacctatg caactcatt    840 agcgacaaca agggaaaaca ctaaatggca gaatggaaga gatgtgtggt ggcaggatgt    900
tatttctcaa tatccaacat cgtgtgaggt ggaatgggtt gatgcagaag atccctgtt    960 tttgctctac accagtggaa gtactgggaa gccaaagggt gtcctacaca caactggagg   1020
gtatatgatc tacactgcta caacgttcaa atatgcattt gactacaaat caacagatgt   1080
atactggtgt acagcagatt gtggttggat aactggccat agctatgtta cttatggacc   1140
aatgcttaat ggagccactg ttgttgtcct tgagggggct ccaaactacc ctgaccctgg   1200
acgctgtcgg gatattgttg acaaatacaa ggtttcaata ttttatactg ccccaacatt   1260
ggtgaggtct ctcatgcgcg atgacgataa gtttgtaaca cgtcactcgc gcaaatcgct   1320
gcgggtcctt ggaagtgttg gtgagcccat caatcctagt gcctggagat ggttcttcaa   1380
tgtagtcggt gattcaaggt gtcccatttc agatacgtgg tggcaaactg aaactggtgg   1440
cttcatgata accccattgc caggtgcttg gccccagaaa cctggttcag ccactttccc   1500
tttctttggt gttcagcctg tcatagttga tgaaaaggggc aatgaaatcg aaggcgagtg   1560
tagtggttat cttgtgtca aggttcatg gcccggggcg tttcgaactc tgtttgggga    1620
tcatgaaaga tacgaaacca catactttaa accttttgcc ggatattatt tcagtggtga   1680
tggttgcagc agagacaagg atggttacta ctggcttaca gggaggggtg atgatgttat   1740
caacgtcagt ggccatcgaa tcggaactgc tgaagtagaa tctgctctgg ttttacaccc   1800
tcaatgtgca gaagcagctg ttgtaggcat agaacatgag gtaaaaggtc agggaatta    1860 tgcgtttgtc actcttctgg aaggtgttcc ttacagcgag gagcttcgta aaagcctagt   1920
actaatggtc cgaaatcaga ttggggcttt tgcagcaccg acagaatac attgggcacc    1980 agggttgcca agacgagaa gcggaaagat aatgaggaga atcttgagaa agattgcttc   2040
gaggcaatta gaagaactcg gagatactag cacactcgcg gatcctagtg tagttgatca   2100
gcttattgca cttgccgatg tgtgatgact aaccatagca tatgagccaa tggagagtaa   2160
tggagttttg tgcatctata tatgttttca ggtgtcttat agagggaatg gtacaaaaat   2220
ctgaaacaag attcaggtgt tttggaggga ataaagtaag cagactatat tgttgtgttt   2280
ttgaataaag aaatttcagt ctcatgaatt tggttttgga taagatggtc ataggattat   2340
caaattaatt aaaagttaca aaatataaa aaaaaaaaa aa                         2382
```

<210> SEQ ID NO 2
<211> LENGTH: 693
<212> TYPE: PRT
<213> ORGANISM: Arabidopsis Thaliana

<400> SEQUENCE: 2

```
Met Ser Ser Asn Ser Leu Arg His Val Glu Ser Met Ser Gln Leu Pro
 1               5                  10                  15
```

-continued

```
Ser Gly Ala Gly Lys Ile Ser Gln Leu Asn Ala Val Val Leu Gly Glu
         20                  25                  30

Ser Leu Ala Ser Glu Glu Asn Asp Leu Val Phe Pro Ser Lys Glu Phe
         35                  40                  45

Ser Gly Gln Ala Leu Val Ser Ser Pro Gln Gln Tyr Met Glu Met His
         50                  55                  60

Lys Arg Ser Met Asp Asp Pro Ala Ala Phe Trp Ser Asp Ile Ala Ser
 65                  70                  75                  80

Glu Phe Tyr Trp Lys Gln Lys Trp Gly Asp Gln Val Phe Ser Glu Asn
                 85                  90                  95

Leu Asp Val Arg Lys Gly Pro Ile Ser Ile Glu Trp Phe Lys Gly Gly
                100                 105                 110

Ile Thr Asn Ile Cys Tyr Asn Cys Leu Asp Lys Asn Val Glu Ala Gly
            115                 120                 125

Leu Gly Asp Lys Thr Ala Ile His Trp Glu Gly Asn Glu Leu Gly Val
        130                 135                 140

Asp Ala Ser Leu Thr Tyr Ser Glu Leu Leu Gln Arg Val Cys Gln Leu
145                 150                 155                 160

Ala Asn Tyr Leu Lys Asp Asn Gly Val Lys Lys Gly Asp Ala Val Val
                165                 170                 175

Ile Tyr Leu Pro Met Leu Met Glu Leu Pro Ile Ala Met Leu Ala Cys
            180                 185                 190

Ala Arg Ile Gly Ala Val His Ser Val Phe Ala Gly Phe Ser Ala
        195                 200                 205

Asp Ser Leu Ala Gln Arg Ile Val Asp Cys Lys Pro Asn Val Ile Leu
    210                 215                 220

Thr Cys Asn Ala Val Lys Arg Gly Pro Lys Thr Ile Asn Leu Lys Ala
225                 230                 235                 240

Ile Val Asp Ala Ala Leu Asp Gln Ser Ser Lys Asp Gly Val Ser Val
                245                 250                 255

Gly Ile Cys Leu Thr Tyr Asp Asn Ser Leu Ala Thr Thr Arg Glu Asn
            260                 265                 270

Thr Lys Trp Gln Asn Gly Arg Asp Val Trp Gln Asp Val Ile Ser
        275                 280                 285

Gln Tyr Pro Thr Ser Cys Glu Val Glu Trp Val Asp Ala Glu Asp Pro
    290                 295                 300

Leu Phe Leu Leu Tyr Thr Ser Gly Ser Thr Gly Lys Pro Lys Gly Val
305                 310                 315                 320

Leu His Thr Thr Gly Gly Tyr Met Ile Tyr Thr Ala Thr Phe Lys
                325                 330                 335

Tyr Ala Phe Asp Tyr Lys Ser Thr Asp Val Tyr Trp Cys Thr Ala Asp
            340                 345                 350

Cys Gly Trp Ile Thr Gly His Ser Tyr Val Thr Tyr Gly Pro Met Leu
        355                 360                 365

Asn Gly Ala Thr Val Val Val Leu Glu Gly Ala Pro Asn Tyr Pro Asp
    370                 375                 380

Pro Gly Arg Cys Arg Asp Ile Val Asp Lys Lys Val Ser Ile Phe
385                 390                 395                 400

Tyr Thr Ala Pro Thr Leu Val Arg Ser Leu Met Arg Asp Asp Lys
                405                 410                 415

Phe Val Thr Arg His Ser Arg Lys Ser Leu Arg Val Leu Gly Ser Val
            420                 425                 430

Gly Glu Pro Ile Asn Pro Ser Ala Trp Arg Trp Phe Phe Asn Val Val
```

-continued

```
                435                 440                 445
Gly Asp Ser Arg Cys Pro Ile Ser Asp Thr Trp Trp Gln Thr Glu Thr
    450                 455                 460
Gly Gly Phe Met Ile Thr Pro Leu Pro Gly Ala Trp Pro Gln Lys Pro
465                 470                 475                 480
Gly Ser Ala Thr Phe Pro Phe Gly Val Gln Pro Val Ile Val Asp
                485                 490                 495
Glu Lys Gly Asn Glu Ile Glu Gly Glu Cys Ser Gly Tyr Leu Cys Val
                500                 505                 510
Lys Gly Ser Trp Pro Gly Ala Phe Arg Thr Leu Phe Gly Asp His Glu
    515                 520                 525
Arg Tyr Glu Thr Thr Tyr Phe Lys Pro Phe Ala Gly Tyr Tyr Phe Ser
    530                 535                 540
Gly Asp Gly Cys Ser Arg Asp Lys Asp Gly Tyr Tyr Trp Leu Thr Gly
545                 550                 555                 560
Arg Val Asp Asp Val Ile Asn Val Ser Gly His Arg Ile Gly Thr Ala
                565                 570                 575
Glu Val Glu Ser Ala Leu Val Leu His Pro Gln Cys Ala Glu Ala Ala
                580                 585                 590
Val Val Gly Ile Glu His Glu Val Lys Gly Gln Gly Ile Tyr Ala Phe
                595                 600                 605
Val Thr Leu Leu Glu Gly Val Pro Tyr Ser Glu Glu Leu Arg Lys Ser
    610                 615                 620
Leu Val Leu Met Val Arg Asn Gln Ile Gly Ala Phe Ala Ala Pro Asp
625                 630                 635                 640
Arg Ile His Trp Ala Pro Gly Leu Pro Lys Thr Arg Ser Gly Lys Ile
                645                 650                 655
Met Arg Arg Ile Leu Arg Lys Ile Ala Ser Arg Gln Leu Glu Glu Leu
                660                 665                 670
Gly Asp Thr Ser Thr Leu Ala Asp Pro Ser Val Val Asp Gln Leu Ile
    675                 680                 685
Ala Leu Ala Asp Val
    690

<210> SEQ ID NO 3
<211> LENGTH: 1131
<212> TYPE: DNA
<213> ORGANISM: Arabidopsis Thaliana
<220> FEATURE:
<221> NAME/KEY: old_sequence
<222> LOCATION: (12)
<223> OTHER INFORMATION: originally "n"

<400> SEQUENCE: 3
aatggccaag aggctgtttc tactggcttt atcaagctcc ttaccaagtc tgactctgtc      60
gttagtacct accgtgacca tgtccatgcc ctcagcaaag gtgtctctgc tcgtgctgtt     120
atgagcgagc tcttcggcaa ggttactgga tgctgcagag gccaaggtgg atccatgcac     180
atgttctcca agaacacaa catgcttggt ggctttgctt ttattggtga aggcattcct     240
gtcgccactg gtgctgcctt agctccaag tacaggaggg aagtcttgaa acaggattgt     300
gatgatgtca ctgtcgcctt tttcggagat ggaacttgta caacggaca gttcttcgag     360
tgtctcaaca tggctgctct ctataaactg cctattatct tgttgtcga gaataacttg     420
tgggccattg gatgtctca cttgagagcc acttctgacc ccgagatttg aagaaaggt     480
cctgcatttg ggatgcctgg tgttcatgtt gacggtatgg atgtcttgaa ggtcagggaa     540
```

-continued

```
gtcgctaaag aggctgtcac tagagctaga agaggagaag gtccaacctt ggttgaatgt    600
gagacttata gatttagagg acactccttg gctgatcccg atgagctccg tgatgctgct    660
gagaaagcca aatacgcggc tagagaccca atcgcagcat tgaagaagta tttgatagag    720
aacaagcttg caaaggaagc agagctaaag tcaatagaga aaaagataga cgagttggtg    780
gaggaagcgg ttgagtttgc agacgctagt ccacagcccg tcgcagtca gttgctagag    840 aatgtgtttg ctgatccaaa aggatttgga attggacctg atggacggta cagatgtgag    900
gaccccaagt ttaccgaagg cacagctcaa gtctgagaag acaagtttaa ccataagctg    960
tctactgttt cttcgatgtt tctatatatc ttattaagtt aaatgctaca gagaatcagt   1020
ttgaatcatt tgcacttttt gcttttttgtt tggtgttact aaattatcac aaggttcttc   1080
ttgtagttcg ttgggttttc attggttacc acttaaaaaa aaaaaaaaaa a            1131
```

<210> SEQ ID NO 4
<211> LENGTH: 311
<212> TYPE: PRT
<213> ORGANISM: Arabidopsis Thaliana

<400> SEQUENCE: 4

```
Asn Gly Gln Glu Ala Val Ser Thr Gly Phe Ile Lys Leu Leu Thr Lys
  1               5                  10                  15

Ser Asp Ser Val Val Ser Thr Tyr Arg Asp His Val His Ala Leu Ser
             20                  25                  30

Lys Gly Val Ser Ala Arg Ala Val Met Ser Glu Leu Phe Gly Lys Val
         35                  40                  45

Thr Gly Cys Cys Arg Gly Gln Gly Gly Ser Met His Met Phe Ser Lys
     50                  55                  60

Glu His Asn Met Leu Gly Gly Phe Ala Phe Ile Gly Glu Gly Ile Pro
 65                  70                  75                  80

Val Ala Thr Gly Ala Ala Phe Ser Ser Lys Tyr Arg Arg Glu Val Leu
                 85                  90                  95

Lys Gln Asp Cys Asp Asp Val Thr Val Ala Phe Phe Gly Asp Gly Thr
            100                 105                 110

Cys Asn Asn Gly Gln Phe Phe Glu Cys Leu Asn Met Ala Ala Leu Tyr
        115                 120                 125

Lys Leu Pro Ile Ile Phe Val Val Glu Asn Asn Leu Trp Ala Ile Gly
    130                 135                 140

Met Ser His Leu Arg Ala Thr Ser Asp Pro Glu Ile Trp Lys Lys Gly
145                 150                 155                 160

Pro Ala Phe Gly Met Pro Gly Val His Val Asp Gly Met Asp Val Leu
                165                 170                 175

Lys Val Arg Glu Val Ala Lys Glu Ala Val Thr Arg Ala Arg Arg Gly
            180                 185                 190

Glu Gly Pro Thr Leu Val Glu Cys Glu Thr Tyr Arg Phe Arg Gly His
        195                 200                 205

Ser Leu Ala Asp Pro Asp Glu Leu Arg Asp Ala Ala Glu Lys Ala Lys
    210                 215                 220

Tyr Ala Ala Arg Asp Pro Ile Ala Ala Leu Lys Lys Tyr Leu Ile Glu
225                 230                 235                 240

Asn Lys Leu Ala Lys Glu Ala Glu Leu Lys Ser Ile Glu Lys Lys Ile
                245                 250                 255

Asp Glu Leu Val Glu Glu Ala Val Glu Phe Ala Asp Ala Ser Pro Gln
            260                 265                 270
```

```
Pro Gly Arg Ser Gln Leu Leu Glu Asn Val Phe Ala Asp Pro Lys Gly
        275                 280                 285

Phe Gly Ile Gly Pro Asp Gly Arg Tyr Arg Cys Glu Asp Pro Lys Phe
        290                 295                 300

Thr Glu Gly Thr Ala Gln Val
305                 310

<210> SEQ ID NO 5
<211> LENGTH: 1209
<212> TYPE: DNA
<213> ORGANISM: Arabidopsis Thaliana

<400> SEQUENCE: 5
gcggatacgt ctgcgagcac tggacatgaa ctattgcttt tcgaggctct tcaggaaggt      60
ctggaagaag agatggacag agatccacat gtatgtgtta tgggtgaaga tgttggccat     120
tacgagggtt cctacaaggt aaccaaaggc cttgctgata aatttggtga cctcagggtt     180
ctcgacactc ctatttgtga aaatgcattc accggtatgg gcattggagc tgccatgact     240
ggtctaagac ccgttattga aggtatgaac atgggtttcc tcctcctcgc cttcaaccaa     300
atctccaaca actgtggaat gcttcactac acatccggtg gtcagtttac gatcccggtt     360
gtcatccgtg gacctggtgg agtgggacgc cagcttggtg ctgagcattc acagaggtta     420
gaatcttact ttcagtccat ccctgggatc cagatggttg cttgctcaac tccttacaac     480
gccaaagggt tgatgaaagc cgcaataaga agcgagaacc ctgtgattct gttcgaacac     540
gtgctgcttt acaatctcaa ggagaaaatc ccggatgaag attacatctg taaccttgaa     600
gaagctgaga tggtcagacc tggcgagcac attaccatcc tcacttactc gcgaatgagg     660
taccatgtga tgcaggcagc aaaaactctg gtgaacaaag ggtatgaccc cgaggttatc     720
gacatcaggt cactgaaacc gttcgacctt cacacaattg gaaactcggt gaagaaaaca     780
catcgggttt tgatcgtgga ggagtgtatg agaaccggtg ggattggggc aagtcttaca     840
gctgccatca cgagaacttt catgactac ttagatgctc cggtgatgtg tttatcttct     900
caagacgttc ctacaccctta cgctggtaca ctggaggagt ggaccgtggt tcaaccggct     960
cagatcgtga ccgctgtcga gcagctttgc cagtaaattc atatttatcc gatgaaccat    1020
tatttatcat ttacctctcc atttcctttc tctgtagctt agttcttaaa gaatttgtct    1080
aagatggttt gttttgtta aagtttgtct cctttgttgt gtctttaat atggtttgta    1140
actcagaatg tttgtttgtt aattttatct cccacttctt ttaaaaaaa aaaaaaaaa    1200
aaaaaaaa                                                             1209

<210> SEQ ID NO 6
<211> LENGTH: 331
<212> TYPE: PRT
<213> ORGANISM: Arabidopsis Thaliana

<400> SEQUENCE: 6

Ala Asp Thr Ser Ala Ser Thr Gly His Glu Leu Leu Phe Glu Ala
 1               5                  10                  15

Leu Gln Glu Gly Leu Glu Glu Met Asp Arg Asp Pro His Val Cys
            20                  25                  30

Val Met Gly Glu Asp Val Gly His Tyr Gly Gly Ser Tyr Lys Val Thr
            35                  40                  45

Lys Gly Leu Ala Asp Lys Phe Gly Asp Leu Arg Val Leu Asp Thr Pro
 50                  55                  60
```

Ile Cys Glu Asn Ala Phe Thr Gly Met Gly Ile Gly Ala Ala Met Thr
65                  70                  75                  80

Gly Leu Arg Pro Val Ile Glu Gly Met Asn Met Gly Phe Leu Leu Leu
                85                  90                  95

Ala Phe Asn Gln Ile Ser Asn Asn Cys Gly Met Leu His Tyr Thr Ser
            100                 105                 110

Gly Gly Gln Phe Thr Ile Pro Val Val Ile Arg Gly Pro Gly Gly Val
        115                 120                 125

Gly Arg Gln Leu Gly Ala Glu His Ser Gln Arg Leu Glu Ser Tyr Phe
    130                 135                 140

Gln Ser Ile Pro Gly Ile Gln Met Val Ala Cys Ser Thr Pro Tyr Asn
145                 150                 155                 160

Ala Lys Gly Leu Met Lys Ala Ala Ile Arg Ser Glu Asn Pro Val Ile
                165                 170                 175

Leu Phe Glu His Val Leu Leu Tyr Asn Leu Lys Glu Lys Ile Pro Asp
            180                 185                 190

Glu Asp Tyr Ile Cys Asn Leu Glu Glu Ala Glu Met Val Arg Pro Gly
        195                 200                 205

Glu His Ile Thr Ile Leu Thr Tyr Ser Arg Met Arg Tyr His Val Met
    210                 215                 220

Gln Ala Ala Lys Thr Leu Val Asn Lys Gly Tyr Asp Pro Glu Val Ile
225                 230                 235                 240

Asp Ile Arg Ser Leu Lys Pro Phe Asp Leu His Thr Ile Gly Asn Ser
                245                 250                 255

Val Lys Lys Thr His Arg Val Leu Ile Val Glu Glu Cys Met Arg Thr
            260                 265                 270

Gly Gly Ile Gly Ala Ser Leu Thr Ala Ala Ile Asn Glu Asn Phe His
        275                 280                 285

Asp Tyr Leu Asp Ala Pro Val Met Cys Leu Ser Ser Gln Asp Val Pro
    290                 295                 300

Thr Pro Tyr Ala Gly Thr Leu Glu Glu Trp Thr Val Val Gln Pro Ala
305                 310                 315                 320

Gln Ile Val Thr Ala Val Glu Gln Leu Cys Gln
                325                 330

<210> SEQ ID NO 7
<211> LENGTH: 1530
<212> TYPE: DNA
<213> ORGANISM: Arabidopsis Thaliana

<400> SEQUENCE: 7
aattcggcac gagacccaac ctgtgaagct accccattc tctctcaacg ttttcgtttt      60
gaaatggcga ggaagaagat cagagagtat gactcaaaga ggttggtgaa ggaacatttc    120
aaaaggcttt ctggcaaaga gcttcctatc agatccgttc agattaatga acaactgat    180 ctaaatgagc tagttgaaaa ggaaccttgg ctctcgtctg agaagctggt ggtgaaacct    240
gacatgttgt ttggaaagcg tggcaagagt ggtttggttg ccttgaaatt agattttgct    300
gatgttgcca cttttgttaa agaacgtttg ggaaagagg tagagatgag tggatgcaaa    360
ggacccataa caacattcat agttgaacca tttgttccac acaatgagga gtattatctc    420
aatgttgtct cggatcggct tggttgcagc ataagctttt ctgagtgtgg aggaattgag    480
atcgaggaga actgggacaa ggtcaagaca atatttttac caacaggtgc ttccctgaca    540
cctgaaatat gtgcacctct tgtcgcaact cttcccttag agatcaaagc tgaaattgaa    600

```
gaatttatca aagtcatttt caccctattc caagatcttg atttcacttt cttggagatg      660
aatcctttca ctctagttga tggaagtcct tatcctctgg atatgagggg tgagcttgat      720
gatactgctg ccttcaaaaa ctttaaaaaa tggggcgaca ttgaatttcc tctgccattt      780
ggaagagtaa tgagtcctac agaaagcttt atccacggac tggatgagaa acaagtgcg      840 tctttgaagt ttaccgttct gaaccccaag ggacggattt ggacaatggt agctggtgga      900
ggagcaagtg tcatctatgc ggatacggtt ggagatctcg gtatgcatc tgaacttggc       960 aactatgctg aatacagtgg agcacccaaa gaagatgaag ttttgcagta cgccagagtc     1020
gttattgatt gtgctacagc aaacccggat ggaaaaagca gagcccttgt catcggaggc     1080
ggaattgcca acttcactga cgttgctgct actttcaatg gcataatccg cgctcttaaa     1140
gaaaaggaag caaagctgaa agcagcaagg atgcatatat ttgtgaggag aggaggacca    1200
aactaccaaa agggacttgc taaaatgcga gcccttggag atgatatcgg tgtccccatc    1260
gaggtctatg gcccagaagc aaccatgaca ggtatctgca aggaggcaat ccagtacatc    1320
acagcagcag cataagcttc tctcagtacc ttctatgacc aaaactttgt ctgtgtttta    1380
gagcctttat ttactgtggt taagattact caagctataa gatacttgca atttcttgaa    1440
aacttctgtt gttcgattct ctttccccta acgttttctt cagattcaat aaataatcgt    1500 tacttttaa aaaaaaaaaa aaaaaaaaa                                        1530
```

<210> SEQ ID NO 8
<211> LENGTH: 423
<212> TYPE: PRT
<213> ORGANISM: Arabidopsis Thaliana

<400> SEQUENCE: 8

```
Met Ala Arg Lys Lys Ile Arg Glu Tyr Asp Ser Lys Arg Leu Val Lys
  1               5                  10                  15

Glu His Phe Lys Arg Leu Ser Gly Lys Glu Leu Pro Ile Arg Ser Val
                 20                  25                  30

Gln Ile Asn Glu Thr Thr Asp Leu Asn Glu Leu Val Glu Lys Glu Pro
             35                  40                  45

Trp Leu Ser Ser Glu Lys Leu Val Lys Pro Asp Met Leu Phe Gly
         50                  55                  60

Lys Arg Gly Lys Ser Gly Leu Val Ala Leu Lys Leu Asp Phe Ala Asp
 65                  70                  75                  80

Val Ala Thr Phe Val Lys Glu Arg Leu Gly Lys Glu Val Glu Met Ser
                 85                  90                  95

Gly Cys Lys Gly Pro Ile Thr Thr Phe Ile Val Glu Pro Phe Val Pro
            100                 105                 110

His Asn Glu Glu Tyr Tyr Leu Asn Val Val Ser Asp Arg Leu Gly Cys
        115                 120                 125

Ser Ile Ser Phe Ser Glu Cys Gly Gly Ile Glu Ile Glu Glu Asn Trp
    130                 135                 140

Asp Lys Val Lys Thr Ile Phe Leu Pro Thr Gly Ala Ser Leu Thr Pro
145                 150                 155                 160

Glu Ile Cys Ala Pro Leu Val Ala Thr Leu Pro Leu Glu Ile Lys Ala
                165                 170                 175

Glu Ile Glu Glu Phe Ile Lys Val Ile Phe Thr Leu Phe Gln Asp Leu
            180                 185                 190

Asp Phe Thr Phe Leu Glu Met Asn Pro Phe Thr Leu Val Asp Gly Ser
        195                 200                 205
```

```
Pro Tyr Pro Leu Asp Met Arg Gly Glu Leu Asp Asp Thr Ala Ala Phe
    210                 215                 220
Lys Asn Phe Lys Lys Trp Gly Asp Ile Glu Phe Pro Leu Pro Phe Gly
225                 230                 235                 240
Arg Val Met Ser Pro Thr Glu Ser Phe Ile His Gly Leu Asp Glu Lys
                245                 250                 255
Thr Ser Ala Ser Leu Lys Phe Thr Val Leu Asn Pro Lys Gly Arg Ile
            260                 265                 270
Trp Thr Met Val Ala Gly Gly Ala Ser Val Ile Tyr Ala Asp Thr
        275                 280                 285
Val Gly Asp Leu Gly Tyr Ala Ser Glu Leu Gly Asn Tyr Ala Glu Tyr
    290                 295                 300
Ser Gly Ala Pro Lys Glu Asp Glu Val Leu Gln Tyr Ala Arg Val Val
305                 310                 315                 320
Ile Asp Cys Ala Thr Ala Asn Pro Asp Gly Lys Ser Arg Ala Leu Val
                325                 330                 335
Ile Gly Gly Gly Ile Ala Asn Phe Thr Asp Val Ala Ala Thr Phe Asn
            340                 345                 350
Gly Ile Ile Arg Ala Leu Lys Glu Lys Glu Ala Lys Leu Lys Ala Ala
        355                 360                 365
Arg Met His Ile Phe Val Arg Arg Gly Pro Asn Tyr Gln Lys Gly
    370                 375                 380
Leu Ala Lys Met Arg Ala Leu Gly Asp Asp Ile Gly Val Pro Ile Glu
385                 390                 395                 400
Val Tyr Gly Pro Glu Ala Thr Met Thr Gly Ile Cys Lys Glu Ala Ile
                405                 410                 415
Gln Tyr Ile Thr Ala Ala Ala
            420

<210> SEQ ID NO 9
<211> LENGTH: 1030
<212> TYPE: DNA
<213> ORGANISM: Arabidopsis Thaliana

<400> SEQUENCE: 9
gatctcagct ctgcaattaa gagtgggaaa gtccgggctc ctactcacat catctccacc    60
atttctgatg acagagggga ggaaccatgc tatgctggtg tgccaatgtc atccatcatt   120
gaacagggtt atggcgtggg agatgtcatt tccctcctat ggttcaaacg tagtcttcct   180
cgatattgta ccaaattcat cgagatatgc ataatgttgt gcgctgacca cggtccatgc   240
gtctctggcg ctcacaacac catcgtaaca gcaagagcag gaaaagacct tgtctcaagt   300
cttgtctcag gtctattaac aatcggtcct agatttggtg gtgccattga tgatgcagca   360
cgatacttca aggacgcttg tgacaggaat ctcacacctt atgaattcgt ggaaggcatg   420
aagaagaaag gaatccgtgt ccctggcatt ggtcacagga taaagagcag agacaacaga   480
gacaaaagag tggagctgct tcagaaattt gcacggtcta acttccctgc agtgaagtac   540
atggaatacg cagtccaagt agagacatac acactgtcta aagccaacaa cctggtactc   600
aacgtcgatg gagccattgg atctctcttc ttagaccttc tcgctggaag tgggatgttc   660
acaaaacaag agatagacga aatagttcag atcggttatc tcaacggcct cttcgtcctc   720
gctcgatcca tcggtttaat cgggcacaca ttcgatcaga agagactgaa gcagccactg   780
taccgacacc cgtgggaaga tgtcttgtac accaagtaat catatcatta ttcacttctt   840
```

-continued

| | |
|---|---|
| ctggtcgttc cttattcctg ttatcattct ctcccattca gttaggctat gtttgattat | 900 |
| atatttgttc tgacactcta tctgttgtga tctcttaatg cttgaaaaaa taaaagaaag | 960 |
| ttcaatttta gaagaattat aatgttttga ttctaaatta ctcacactgg cggccgccac | 1020 |
| gtggagctcc | 1030 |

<210> SEQ ID NO 10
<211> LENGTH: 272
<212> TYPE: PRT
<213> ORGANISM: Arabidopsis Thaliana

<400> SEQUENCE: 10

```
Asp Leu Ser Ser Ala Ile Lys Ser Gly Lys Val Arg Ala Pro Thr His
  1               5                  10                  15

Ile Ile Ser Thr Ile Ser Asp Asp Arg Gly Glu Glu Pro Cys Tyr Ala
             20                  25                  30

Gly Val Pro Met Ser Ser Ile Ile Glu Gln Gly Tyr Gly Val Gly Asp
         35                  40                  45

Val Ile Ser Leu Leu Trp Phe Lys Arg Ser Leu Pro Arg Tyr Cys Thr
     50                  55                  60

Lys Phe Ile Glu Ile Cys Ile Met Leu Cys Ala Asp His Gly Pro Cys
 65                  70                  75                  80

Val Ser Gly Ala His Asn Thr Ile Val Thr Ala Arg Ala Gly Lys Asp
             85                  90                  95

Leu Val Ser Ser Leu Val Ser Gly Leu Leu Thr Ile Gly Pro Arg Phe
        100                 105                 110

Gly Gly Ala Ile Asp Asp Ala Ala Arg Tyr Phe Lys Asp Ala Cys Asp
        115                 120                 125

Arg Asn Leu Thr Pro Tyr Glu Phe Val Glu Gly Met Lys Lys Lys Gly
    130                 135                 140

Ile Arg Val Pro Gly Ile Gly His Arg Ile Lys Ser Arg Asp Asn Arg
145                 150                 155                 160

Asp Lys Arg Val Glu Leu Leu Gln Lys Phe Ala Arg Ser Asn Phe Pro
                165                 170                 175

Ala Val Lys Tyr Met Glu Tyr Ala Val Gln Val Glu Thr Tyr Thr Leu
            180                 185                 190

Ser Lys Ala Asn Asn Leu Val Leu Asn Val Asp Gly Ala Ile Gly Ser
        195                 200                 205

Leu Phe Leu Asp Leu Leu Ala Gly Ser Gly Met Phe Thr Lys Gln Glu
    210                 215                 220

Ile Asp Glu Ile Val Gln Ile Gly Tyr Leu Asn Gly Leu Phe Val Leu
225                 230                 235                 240

Ala Arg Ser Ile Gly Leu Ile Gly His Thr Phe Asp Gln Lys Arg Leu
                245                 250                 255

Lys Gln Pro Leu Tyr Arg His Pro Trp Glu Asp Val Leu Tyr Thr Lys
                260                 265                 270
```

<210> SEQ ID NO 11
<211> LENGTH: 2203
<212> TYPE: DNA
<213> ORGANISM: Arabidopsis Thaliana

<400> SEQUENCE: 11

| | |
|---|---|
| cgcggccgcg tcgactttct ctctaccacc atttattctc tccttaatca ctgactcgac | 60 |
| tcgggtcgtg accagttttt tctatctgag ctatggcaac gggacagctt ttttctcgta | 120 |

-continued

| | |
|---|---|
| ccacacaagc tttgttctac aactataagc agcttcctgt tcaacgaatg ctcgatttcg | 180 |
| actttctctg tggacgtgaa acgccttctg ttgctggaat cataaatcct ggttctgaag | 240 |
| gttttcaaaa gctctttttc gggcaggagg aaatcgctat ccctgttcat gccgccattg | 300 |
| aggcagcttg tgctgcgcat ccaacagcgg atgtattcat caactttgca tcttttagga | 360 |
| gtgctgctgc ttcatccatg gctgctttga agcagccgac tattaaagtt gtggcaatta | 420 |
| tagctgaagg tgttccagaa tcagacacta agcagctgat tgcgtatgct cgtgcaaaca | 480 |
| ataaggttgt tattggaccg gctactgttg gaggtattca agctggagcc tttaagattg | 540 |
| gtgatactgc aggaacaatt gataacatta tccagtgcaa gctatacaga cctggatctg | 600 |
| ttggttttgt ctccaaatct ggtggaatgt ctaatgaaat gtacaatact gttgcccgtg | 660 |
| tgactgatgg gatctacgaa ggcattgcta ttggtggaga cgtgttccca ggatcgactt | 720 |
| tatctgacca catccttcgg tttaacaaca tcccacagat aaaaatgatg gttgtacttg | 780 |
| gagagcttgg aggaagagat gaatactctc ttgttgaagc tttgaaagag ggaaaagtca | 840 |
| ataaacctgt ggttgcttgg gtcagtggaa cttgtgcacg actcttcaag tctgaagtac | 900 |
| agtttggtca tgcaggtgcc aaaagtggcg gcgagatgga gtctgcacaa gccaagaatc | 960 |
| aagctctcat agatgctgga gctattgttc ccacttcatt tgaagctcta gaatctgcaa | 1020 |
| tcaaagagac ttttgagaaa ctggttgaag aaggaaaggt ctctcctatc aaggaagtca | 1080 |
| ttcctccaca aatccctgag gatctcaatt ctgcaattaa gagtgggaaa gtccgggctc | 1140 |
| ctactcacat catctccacc atatctgatg acagagggga ggaaccatgc tatgctggtg | 1200 |
| ttccaatgtc ttccatcatc gaacaaggct atggagtggg tgatgtcatt tcccttctat | 1260 |
| ggttcaaacg tagtctacct cgttactgta caaaattcat tgagatatgc ataatgctgt | 1320 |
| gtgctgatca cggtccatgc gtctccggcg ctcacaacac cattgtaaca gcaagagcag | 1380 |
| gcaaagacct cgtctcaagt cttgtctcag gtttattgac cattggtccc cgatttggtg | 1440 |
| gtgccattga tgacgctgct cgatacttca agacgcgtg tgacaggaat ctcacacctt | 1500 |
| atgaatttgt tgagggaatg aagaaaaagg gaatccgagt ccccgggatt ggacacagga | 1560 |
| tcaagagcag agacaacaga gacaaaagag tggagcttct tcagaaattt gctcggtcca | 1620 |
| acttcccatc agtgaagtac atggagtacg cagtgacagt ggagacatac acgctctcaa | 1680 |
| aggcaaacaa cctcgtactc aacgttgatg gagccattgg atctctcttc ttggaccttc | 1740 |
| tagctggaag tgggatgttc actaaacaag agattgacga gattgttcag atcggttatc | 1800 |
| tcaacggtct gtttgttctt gctcgctcca tcggtttgat cgggcacacg tttgatcaga | 1860 |
| agagattgaa gcagccactg tatcgtcacc catgggaaga tgtgttgtac accaagtaaa | 1920 |
| actcatttca atcctatttt tgttattatt ccaattaatt agccttttaa aattcttctg | 1980 |
| agagatgttt acttaaaaaa tgcatatcta tatgctcttc ttctgtctct tttgttgtca | 2040 |
| tgtatgtttg ttcacttctt cttctttttt caattattta aactttcttt gtctctcttt | 2100 |
| ctctgttaca tccaaatcac catttttttgg gattctatga gtcatgctca tgcatgtcta | 2160 |
| tatcttaatc gtgatttgtc cttcgaaagt cgacgcggcc gcg | 2203 |

<210> SEQ ID NO 12
<211> LENGTH: 608
<212> TYPE: PRT
<213> ORGANISM: Arabidopsis Thaliana

<400> SEQUENCE: 12

Met Ala Thr Gly Gln Leu Phe Ser Arg Thr Thr Gln Ala Leu Phe Tyr

-continued

```
  1               5                  10                 15
Asn Tyr Lys Gln Leu Pro Val Gln Arg Met Leu Asp Phe Asp Phe Leu
            20                  25                 30
Cys Gly Arg Glu Thr Pro Ser Val Ala Gly Ile Ile Asn Pro Gly Ser
            35                  40                 45
Glu Gly Phe Gln Lys Leu Phe Phe Gly Gln Glu Ile Ala Ile Pro
    50                  55                 60
Val His Ala Ala Ile Glu Ala Ala Cys Ala Ala His Pro Thr Ala Asp
 65                  70                 75                 80
Val Phe Ile Asn Phe Ala Ser Phe Arg Ser Ala Ala Ser Ser Met
                 85                  90                 95
Ala Ala Leu Lys Gln Pro Thr Ile Lys Val Ala Ile Ile Ala Glu
            100                 105                110
Gly Val Pro Glu Ser Asp Thr Lys Gln Leu Ile Ala Tyr Ala Arg Ala
            115                 120                125
Asn Asn Lys Val Val Ile Gly Pro Ala Thr Val Gly Gly Ile Gln Ala
    130                 135                140
Gly Ala Phe Lys Ile Gly Asp Thr Ala Gly Thr Ile Asp Asn Ile Ile
145                 150                 155                160
Gln Cys Lys Leu Tyr Arg Pro Gly Ser Val Gly Phe Val Ser Lys Ser
                165                 170                175
Gly Gly Met Ser Asn Glu Met Tyr Asn Thr Val Ala Arg Val Thr Asp
                180                 185                190
Gly Ile Tyr Glu Gly Ile Ala Ile Gly Gly Asp Val Phe Pro Gly Ser
                195                 200                205
Thr Leu Ser Asp His Ile Leu Arg Phe Asn Asn Ile Pro Gln Ile Lys
    210                 215                220
Met Met Val Val Leu Gly Glu Leu Gly Gly Arg Asp Glu Tyr Ser Leu
225                 230                 235                240
Val Glu Ala Leu Lys Glu Gly Lys Val Asn Lys Pro Val Val Ala Trp
                245                 250                255
Val Ser Gly Thr Cys Ala Arg Leu Phe Lys Ser Glu Val Gln Phe Gly
                260                 265                270
His Ala Gly Ala Lys Ser Gly Gly Glu Met Glu Ser Ala Gln Ala Lys
            275                 280                285
Asn Gln Ala Leu Ile Asp Ala Gly Ala Ile Val Pro Thr Ser Phe Glu
    290                 295                300
Ala Leu Glu Ser Ala Ile Lys Glu Thr Phe Glu Lys Leu Val Glu Glu
305                 310                 315                320
Gly Lys Val Ser Pro Ile Lys Glu Val Ile Pro Gln Ile Pro Glu
            325                 330                335
Asp Leu Asn Ser Ala Ile Lys Ser Gly Lys Val Arg Ala Pro Thr His
            340                 345                350
Ile Ile Ser Thr Ile Ser Asp Asp Arg Gly Glu Glu Pro Cys Tyr Ala
            355                 360                365
Gly Val Pro Met Ser Ser Ile Ile Glu Gln Gly Tyr Gly Val Gly Asp
    370                 375                380
Val Ile Ser Leu Leu Trp Phe Lys Arg Ser Leu Pro Arg Tyr Cys Thr
385                 390                 395                400
Lys Phe Ile Glu Ile Cys Ile Met Leu Cys Ala Asp His Gly Pro Cys
                405                 410                415
Val Ser Gly Ala His Asn Thr Ile Val Thr Ala Arg Ala Gly Lys Asp
            420                 425                430
```

| Leu | Val | Ser | Ser | Leu | Val | Ser | Gly | Leu | Leu | Thr | Ile | Gly | Pro | Arg | Phe |
|---|---|---|---|---|---|---|---|---|---|---|---|---|---|---|---|
| | | 435 | | | | 440 | | | | 445 | | | | | |

| Gly | Gly | Ala | Ile | Asp | Asp | Ala | Ala | Arg | Tyr | Phe | Lys | Asp | Ala | Cys | Asp |
|---|---|---|---|---|---|---|---|---|---|---|---|---|---|---|---|
| | 450 | | | | 455 | | | | 460 | | | | | | |

| Arg | Asn | Leu | Thr | Pro | Tyr | Glu | Phe | Val | Glu | Gly | Met | Lys | Lys | Lys | Gly |
|---|---|---|---|---|---|---|---|---|---|---|---|---|---|---|---|
| 465 | | | | 470 | | | | 475 | | | | | | 480 | |

| Ile | Arg | Val | Pro | Gly | Ile | Gly | His | Arg | Ile | Lys | Ser | Arg | Asp | Asn | Arg |
|---|---|---|---|---|---|---|---|---|---|---|---|---|---|---|---|
| | | | 485 | | | | 490 | | | | | 495 | | | |

| Asp | Lys | Arg | Val | Glu | Leu | Leu | Gln | Lys | Phe | Ala | Arg | Ser | Asn | Phe | Pro |
|---|---|---|---|---|---|---|---|---|---|---|---|---|---|---|---|
| | | 500 | | | | | 505 | | | | | 510 | | | |

| Ser | Val | Lys | Tyr | Met | Glu | Tyr | Ala | Val | Thr | Val | Glu | Thr | Tyr | Thr | Leu |
|---|---|---|---|---|---|---|---|---|---|---|---|---|---|---|---|
| | 515 | | | | | 520 | | | | | 525 | | | | |

| Ser | Lys | Ala | Asn | Asn | Leu | Val | Leu | Asn | Val | Asp | Gly | Ala | Ile | Gly | Ser |
|---|---|---|---|---|---|---|---|---|---|---|---|---|---|---|---|
| | 530 | | | | | 535 | | | | | 540 | | | | |

| Leu | Phe | Leu | Asp | Leu | Leu | Ala | Gly | Ser | Gly | Met | Phe | Thr | Lys | Gln | Glu |
|---|---|---|---|---|---|---|---|---|---|---|---|---|---|---|---|
| 545 | | | | 550 | | | | | 555 | | | | | 560 | |

| Ile | Asp | Glu | Ile | Val | Gln | Ile | Gly | Tyr | Leu | Asn | Gly | Leu | Phe | Val | Leu |
|---|---|---|---|---|---|---|---|---|---|---|---|---|---|---|---|
| | | | 565 | | | | | 570 | | | | | 575 | | |

| Ala | Arg | Ser | Ile | Gly | Leu | Ile | Gly | His | Thr | Phe | Asp | Gln | Lys | Arg | Leu |
|---|---|---|---|---|---|---|---|---|---|---|---|---|---|---|---|
| | | 580 | | | | | 585 | | | | | 590 | | | |

| Lys | Gln | Pro | Leu | Tyr | Arg | His | Pro | Trp | Glu | Asp | Val | Leu | Tyr | Thr | Lys |
|---|---|---|---|---|---|---|---|---|---|---|---|---|---|---|---|
| 595 | | | | | 600 | | | | | 605 | | | | | |

<210> SEQ ID NO 13
<211> LENGTH: 1221
<212> TYPE: DNA
<213> ORGANISM: Arabidopsis Thaliana

<400> SEQUENCE: 13

```
atgtctgcga tactccaagg agctggagct gcaacggctc tctcgccgtt taattctatc      60
gattccaaca aactcgttgc tccttctcgc tcttctcttt cagtgaggag caagagatac     120
attgttgccg atctgatag taaaagcttt ggttctagcc tcgtagctcg tcgctctgag     180
ccgttgatac caaatgctgt tacgacgaag gcggacactg ctgcgagctc tacttcatca     240
aagcctgggt atgagctatt acttttcgag gctcttcaag aaggtctaga agaagagatg     300
gacagagatc cacatgtatg tgtcatgggt gaagatgtag gccattacgg aggctcatac     360
aaagtaacta aaggcctagc tgataagttt ggcgatctca gggttctgga cactccaatc     420
tgtgaaaacg ccttcaccgg tatgggcatt ggagccgcca tgacaggact aagacccgtc     480
atcgaaggta tgaacatggg gtttctactc ttagccttca accaaatctc caacaactgt     540
ggtatgcttc actatacatc cggtggtcaa ttcactatcc cggttgttat ccgtgggcct     600
ggaggtgtgg gccggcagct cggagccgag cattcccagc gtctcgagtc ttacttccag     660
tcaatccctg gatccagat ggtggcttgc tcaacacctt acaacgctaa aggattgatg     720
aaagcggcga taagaagtga gaatcctgtg attctgtttg aacacgttct gctctataac     780
ctcaaggaga gtattccgga tgaagaatac atatgtaatc tggaagaagc agaaatggtc     840
agacccggtg aacacatcac gatactgacg tattcaagga tgaggtacca tgtaatgcag     900
gctgcaaaga cgctggtgaa caagggtat gatccagagg ttatcgacat aaggtcgttg     960
aagccgtttg atctctacac aattggaaac tcggtgaaga agacacaccg ggttttgatt    1020
gtggaggaat gtatgagaac gggaggaatc ggagccagtt tgacggctgc aataaacgag    1080
aactttcatg attacttaga tgctccggtg atgtgtttgt cttctcagga tgtcccaact    1140
```

```
ccttacgccg gtacattgga agaatggacg gttgttcagc cagctcagat cgtcactgcc    1200
gtcgaacaac tttgccagta a                                              1221
```

<210> SEQ ID NO 14
<211> LENGTH: 406
<212> TYPE: PRT
<213> ORGANISM: Arabidopsis Thaliana

<400> SEQUENCE: 14

```
Met Ser Ala Ile Leu Gln Gly Ala Gly Ala Thr Ala Leu Ser Pro
 1               5                  10                  15

Phe Asn Ser Ile Asp Ser Asn Lys Leu Val Ala Pro Ser Arg Ser Ser
                 20                  25                  30

Leu Ser Val Arg Ser Lys Arg Tyr Ile Val Ala Gly Ser Asp Ser Lys
             35                  40                  45

Ser Phe Gly Ser Ser Leu Val Ala Arg Arg Ser Glu Pro Leu Ile Pro
     50                  55                  60

Asn Ala Val Thr Thr Lys Ala Asp Thr Ala Ala Ser Ser Thr Ser Ser
 65                  70                  75                  80

Lys Pro Gly His Glu Leu Leu Leu Phe Glu Ala Leu Gln Glu Gly Leu
                 85                  90                  95

Glu Glu Glu Met Asp Arg Asp Pro His Val Cys Val Met Gly Glu Asp
                100                 105                 110

Val Gly His Tyr Gly Gly Ser Tyr Lys Val Thr Lys Gly Leu Ala Asp
            115                 120                 125

Lys Phe Gly Asp Leu Arg Val Leu Asp Thr Pro Ile Cys Glu Asn Ala
    130                 135                 140

Phe Thr Gly Met Gly Ile Gly Ala Ala Met Thr Gly Leu Arg Pro Val
145                 150                 155                 160

Ile Glu Gly Met Asn Met Gly Phe Leu Leu Leu Ala Phe Asn Gln Ile
                165                 170                 175

Ser Asn Asn Cys Gly Met Leu His Tyr Thr Ser Gly Gly Gln Phe Thr
            180                 185                 190

Ile Pro Val Val Ile Arg Gly Pro Gly Gly Val Gly Arg Gln Leu Gly
    195                 200                 205

Ala Glu His Ser Gln Arg Leu Glu Ser Tyr Phe Gln Ser Ile Pro Gly
    210                 215                 220

Ile Gln Met Val Ala Cys Ser Thr Pro Tyr Asn Ala Lys Gly Leu Met
225                 230                 235                 240

Lys Ala Ala Ile Arg Ser Glu Asn Pro Val Ile Leu Phe Glu His Val
                245                 250                 255

Leu Leu Tyr Asn Leu Lys Glu Ser Ile Pro Asp Glu Glu Tyr Ile Cys
            260                 265                 270

Asn Leu Glu Glu Ala Glu Met Val Arg Pro Gly Glu His Ile Thr Ile
    275                 280                 285

Leu Thr Tyr Ser Arg Met Arg Tyr His Val Met Gln Ala Ala Lys Thr
    290                 295                 300

Leu Val Asn Lys Gly Tyr Asp Pro Glu Val Ile Asp Ile Arg Ser Leu
305                 310                 315                 320

Lys Pro Phe Asp Leu Tyr Thr Ile Gly Asn Ser Val Lys Lys Thr His
                325                 330                 335

Arg Val Leu Ile Val Glu Glu Cys Met Arg Thr Gly Gly Ile Gly Ala
            340                 345                 350
```

-continued

```
Ser Leu Thr Ala Ala Ile Asn Glu Asn Phe His Asp Tyr Leu Asp Ala
        355                 360                 365
Pro Val Met Cys Leu Ser Ser Gln Asp Val Pro Thr Pro Tyr Ala Gly
    370                 375                 380
Thr Leu Glu Glu Trp Thr Val Val Gln Pro Ala Gln Ile Val Thr Ala
385                 390                 395                 400
Val Glu Gln Leu Cys Gln
                405

<210> SEQ ID NO 15
<211> LENGTH: 2083
<212> TYPE: DNA
<213> ORGANISM: Arabidopsis Thaliana
<220> FEATURE:
<221> NAME/KEY: exon
<222> LOCATION: (1)..(453)
<221> NAME/KEY: exon
<222> LOCATION: (455)..(781)
<221> NAME/KEY: exon
<222> LOCATION: (783)..(785)
<221> NAME/KEY: exon
<222> LOCATION: (785)..(1133)
<221> NAME/KEY: exon
<222> LOCATION: (1135)..(2083)

<400> SEQUENCE: 15
aaaataaaaa gagtatatct ctcacacaca tacacaaact tgacagtttt ttaatttctc       60
tgttagtgaa ctcaaacctt cccatttcca tggacaccaa aatcggatcg atcgatgatt      120
gcaagccgac gaacggcgac gtctgtagtc aacaaacgg caccgtcgca acaatccaca      180
actctgttcc ttcctccgct atcaccatca actactgcga cgcgactctc ggccgtcact      240
tagctcgtcg tctcgtccaa gccggcgtta cggatgtttt ctctgttccc ggagatttca      300
acctcacttt gcttgatcac ctcatggctg agccggacct caacctaatc ggatgttgta      360
acgagctaaa cgccggttac gctgccgacg gttacgctag atctcgtgga gtcggcgctt      420
gcgttgttac cttcaccgtt ggtggactca gcgttttaaa cgcgatcgct ggtgcttaca      480
gcgagaatct tcctcttatc tgtatcgtcg gaggtcctaa ctctaacgat tatggcacta      540
accggattct tcatcacacc attggattac ctgattttag ccaagagctt aggtgcttcc      600
aaacggtgac ttgttatcag gcggtggtga acaatttaga tgatgctcat gaacagattg      660
ataaagcaat atcaacagct ttgaaagaga gcaagcctgt gtatataagt gtaagctgta      720
acttagcagc gattcctcat catacattta gccgtgatcc tgtccctttt tctctagctc      780
caagattgag caacaagatg ggtttagaag ctgcggtgga agcaacattg gagtttctga      840
ataaggctgt gaagccagtt atggttggtg gtcctaagtt gcgtgtggct aaagcttgtg      900
atgcctttgt tgagctagct gatgcttcag gctatgcttt ggcgatgatg ccttctgcga      960
aaggctttgt accagagcac catcctcatt tcattggaac ttattgggga gcagtgagca     1020 ctccttttg ctctgagatt gtggaatctg cggatgctta cattttgca ggtccaatct     1080 tcaacgacta tagctctgtt ggttactcgc ttctcctcaa gaaagaaaaa gccatcgttg     1140
tgcaacctga tcgtatcact gtggccaatg gtcctacttt tggttgcatt ttgatgagcg     1200
atttcttcag ggaattgtct aagagggtga agcgtaacga gactgcatat gagaactacc     1260
ataggatctt tgtccctgaa ggtaagccat tgaagtgtga atcaagagag ccattgagag     1320
ttaacacaat gttccagcac attcagaaga tgctctctag tgaaaccgct gtgattgctg     1380
aaaccggtga ttcttggttc aattgccaaa aactaaagct gccaaaagga tgtgggtacg     1440
```

```
                                         -continued agtttcagat gcagtatgga tcgattgggt ggtctgttgg tgcaactcta ggatacgcac   1500
aggcatcacc agagaagcga gtgttggcat tcatcggtga tgggagtttc caagtcacgg   1560
ttcaggacat atcaacaatg ctgcgtaatg gacagaagac gatcatcttc ttgattaaca   1620
atggtggcta caccattgaa gtagagattc atgacggtcc ttataacgtg attaagaact   1680
ggaactacac tggtctcgtt gacgccattc ataacggtga aggcaattgc tggactgcaa   1740
aggtgagata cgaagaggag ttagtggagg cgattacgac agcgacgacg gagaagaaag   1800
attgtctatg tttcatagaa gtgattcttc acaaggatga tacgagcaaa gagttgcttg   1860 agtgggctc acgcgtctct gctgctaaca gccgtcctcc caatcctcag tagaagaagc   1920
aacacagaat cttcaatgct tcttaccaat ttagtgacat tttctgataa gtgttgattt   1980
ttcgaccgtt gggtttaatc atgtttcaaa cttattagta tctctttcca tgtcgcttta   2040
tcatggaata aagtaaagct cctttgcaa aaaaaaaaaa aaa                      2083
```

<210> SEQ ID NO 16
<211> LENGTH: 607
<212> TYPE: PRT
<213> ORGANISM: Arabidopsis Thaliana

<400> SEQUENCE: 16

```
Met Asp Thr Lys Ile Gly Ser Ile Asp Asp Cys Lys Pro Thr Asn Gly
  1               5                  10                  15

Asp Val Cys Ser Pro Thr Asn Gly Thr Val Ala Thr Ile His Asn Ser
             20                  25                  30

Val Pro Ser Ser Ala Ile Thr Ile Asn Tyr Cys Asp Ala Thr Leu Gly
         35                  40                  45

Arg His Leu Ala Arg Arg Leu Val Gln Ala Gly Val Thr Asp Val Phe
     50                  55                  60

Ser Val Pro Gly Asp Phe Asn Leu Thr Leu Leu Asp His Leu Met Ala
 65                  70                  75                  80

Glu Pro Asp Leu Asn Leu Ile Gly Cys Cys Asn Glu Leu Asn Ala Gly
                 85                  90                  95

Tyr Ala Ala Asp Gly Tyr Ala Arg Ser Arg Gly Val Gly Ala Cys Val
            100                 105                 110

Val Thr Phe Thr Val Gly Gly Leu Ser Val Leu Asn Ala Ile Ala Gly
        115                 120                 125

Ala Tyr Ser Glu Asn Leu Pro Leu Ile Cys Ile Val Gly Gly Pro Asn
    130                 135                 140

Ser Asn Asp Tyr Gly Thr Asn Arg Ile Leu His His Thr Ile Gly Leu
145                 150                 155                 160

Pro Asp Phe Ser Gln Glu Leu Arg Cys Phe Gln Thr Val Thr Cys Tyr
                165                 170                 175

Gln Ala Val Val Asn Asn Leu Asp Asp Ala His Glu Gln Ile Asp Lys
            180                 185                 190

Ala Ile Ser Thr Ala Leu Lys Glu Ser Lys Pro Val Tyr Ile Ser Val
        195                 200                 205

Ser Cys Asn Leu Ala Ala Ile Pro His His Thr Phe Ser Arg Asp Pro
    210                 215                 220

Val Pro Phe Ser Leu Ala Pro Arg Leu Ser Asn Lys Met Gly Leu Glu
225                 230                 235                 240

Ala Ala Val Glu Ala Thr Leu Glu Phe Leu Asn Lys Ala Val Lys Pro
                245                 250                 255

Val Met Val Gly Gly Pro Lys Leu Arg Val Ala Lys Ala Cys Asp Ala
```

```
                        260                 265                 270
    Phe Val Glu Leu Ala Asp Ala Ser Gly Tyr Ala Leu Ala Met Met Pro
            275                 280                 285
    Ser Ala Lys Gly Phe Val Pro Glu His His Pro His Phe Ile Gly Thr
        290                 295                 300
    Tyr Trp Gly Ala Val Ser Thr Pro Phe Cys Ser Glu Ile Val Glu Ser
    305                 310                 315                 320
    Ala Asp Ala Tyr Ile Phe Ala Gly Pro Ile Phe Asn Asp Tyr Ser Ser
                    325                 330                 335
    Val Gly Tyr Ser Leu Leu Lys Lys Glu Lys Ala Ile Val Val Gln
                340                 345                 350
    Pro Asp Arg Ile Thr Val Ala Asn Gly Pro Thr Phe Gly Cys Ile Leu
            355                 360                 365
    Met Ser Asp Phe Phe Arg Glu Leu Ser Lys Arg Val Lys Arg Asn Glu
        370                 375                 380
    Thr Ala Tyr Glu Asn Tyr His Arg Ile Phe Val Pro Glu Gly Lys Pro
    385                 390                 395                 400
    Leu Lys Cys Glu Ser Arg Glu Pro Leu Arg Val Asn Thr Met Phe Gln
                    405                 410                 415
    His Ile Gln Lys Met Leu Ser Ser Glu Thr Ala Val Ile Ala Glu Thr
                420                 425                 430
    Gly Asp Ser Trp Phe Asn Cys Gln Lys Leu Lys Leu Pro Lys Gly Cys
            435                 440                 445
    Gly Tyr Glu Phe Gln Met Gln Tyr Gly Ser Ile Gly Trp Ser Val Gly
        450                 455                 460
    Ala Thr Leu Gly Tyr Ala Gln Ala Ser Pro Glu Lys Arg Val Leu Ala
    465                 470                 475                 480
    Phe Ile Gly Asp Gly Ser Phe Gln Val Thr Val Gln Asp Ile Ser Thr
                    485                 490                 495
    Met Leu Arg Asn Gly Gln Lys Thr Ile Ile Phe Leu Ile Asn Asn Gly
                500                 505                 510
    Gly Tyr Thr Ile Glu Val Glu Ile His Asp Gly Pro Tyr Asn Val Ile
            515                 520                 525
    Lys Asn Trp Asn Tyr Thr Gly Leu Val Asp Ala Ile His Asn Gly Glu
        530                 535                 540
    Gly Asn Cys Trp Thr Ala Lys Val Arg Tyr Glu Glu Glu Leu Val Glu
    545                 550                 555                 560
    Ala Ile Thr Thr Ala Thr Thr Glu Lys Lys Asp Cys Leu Cys Phe Ile
                    565                 570                 575
    Glu Val Ile Leu His Lys Asp Asp Thr Ser Lys Glu Leu Leu Glu Trp
                580                 585                 590
    Gly Ser Arg Val Ser Ala Ala Asn Ser Arg Pro Pro Asn Pro Gln
            595                 600                 605

<210> SEQ ID NO 17
<211> LENGTH: 2017
<212> TYPE: DNA
<213> ORGANISM: Arabidopsis Thaliana
<220> FEATURE:
<221> NAME/KEY: exon
<222> LOCATION: (1)..(1000)
<221> NAME/KEY: exon
<222> LOCATION: (1002)..(1508)
<221> NAME/KEY: exon
<222> LOCATION: (1510)..(1519)
<221> NAME/KEY: exon
<222> LOCATION: (1521)..(1531)
```

```
<221> NAME/KEY: exon
<222> LOCATION: (1533)..(2017)

<400> SEQUENCE: 17
```

| | | | | | |
|---|---|---|---|---|---|
| aaaagtacag | ttttctcata | gctctattgt | tcgaaaattc | tgaaacgaac | gttaccacta | 60 |
| tggacactaa | gatcggatct | atcgacgcgt | gtaacccgac | caaccacgat | atcggcggtc | 120 |
| ctccaaacgg | cggagtctcc | accgttcaaa | acacaagtcc | acttcactcc | accaccgtca | 180 |
| gccctgcga | cgcgactctt | ggccgttacc | tagcaagacg | gttagtcgaa | atcggcgtca | 240 |
| ccgatgtctt | ctccgttcct | ggtgatttca | acctgacgct | tctcgatcac | ctaatcgccg | 300 |
| aaccaaacct | caagctgatc | ggttgctgca | acgagcttaa | cgccggatac | gctgctgacg | 360 |
| gttacgctag | atctcgcggt | gttggtgcgt | cgtcgttac | gttcaccgtc | ggtggattga | 420 |
| gtgttctgaa | tgcgatcgcc | ggtgcttaca | gtgagaatct | gcctctgatt | tgcatcgtcg | 480 |
| gtggtccaaa | ctccaacgat | tacggtacca | ataggattct | tcatcataca | attggtttac | 540 |
| ctgatttcac | tcaagagctt | aggtgttttc | aagctgttac | ttgttttcaa | gctgtgatta | 600 |
| ataacttaga | agaggctcat | gaacttatcg | atactgcgat | ttcaactgct | ttgaaagaaa | 660 |
| gcaaacctgt | ttatatcagt | atcagctgta | atttaccggc | gattcctctt | ccgacgttta | 720 |
| gtcgtcatcc | tgttccgttc | atgcttccga | tgaaggttag | caatcagatt | ggtttagatg | 780 |
| cggcggtgga | ggcagctgct | gagttcttga | acaaagctgt | gaagccagtt | cttgttggtg | 840 |
| ggccgaaaat | gcgggttgcg | aaagccgcg | atgcttttgt | tgagcttgct | gatgcttctg | 900 |
| gctatggtct | tgctgtgatg | ccttctgcta | aaggacaagt | acctgagcat | cacaagcatt | 960 |
| ttatagggac | gtattgggga | gctgtgagta | cagcttttg | tgctgaaatc | gttgaatctg | 1020 |
| cggatgctta | tctgttgca | ggtccgattt | tcaacgatta | cagttctggt | gggtattctc | 1080 |
| tgcttctcaa | gaaggagaag | gcaatcatcg | ttcagcctga | tcgggttact | atcggtaacg | 1140 |
| gacctgcgtt | tggatgtgtt | cttatgaagg | attttctaag | cgagttggct | aaacgaatta | 1200 |
| agcacaacaa | cacttcttat | gagaattatc | acaggatcta | tgtcccagaa | ggaaagccctt | 1260 |
| tgagagataa | cccgaatgag | tctttgaggg | ttaatgtact | gttccaacac | attcagaata | 1320 |
| tgctctcttc | tgagtctgct | gtgcttgctg | agacaggaga | ttcctggttc | aactgtcaga | 1380 |
| agctgaagct | ccctgaagga | tgcggttacg | aattccaaat | gcagtacgga | tcaattggct | 1440 |
| ggtcagtggg | tgctactcta | ggctatgctc | aagccatgcc | aaacaggcgt | gtcattgctt | 1500 |
| gtattggaga | tggtagttg | caggtaaccg | cgcaggatgt | atctacgatg | atacggtgtg | 1560 |
| ggcaaaagac | cataatcttc | ctcatcaaca | acggaggcta | caccattgag | gtggaaattc | 1620 |
| acgatggtcc | ttacaatgtc | ataaagaact | ggaactacac | agcttttgtt | gaggccatac | 1680 |
| acaatggaga | aggaaaatgc | tggactgcca | aggtgagatg | cgaggaggag | ttagtgaaag | 1740 |
| caatcaacac | ggcaaccaat | gaggaaaaag | agagcttttg | tttcattgaa | gtgatagtgc | 1800 |
| acaaagacga | tacaagcaag | gaactttgg | agtggggctc | tagagtctct | gctgctaata | 1860 |
| gtcgtccccc | aaatccgcag | tagagtatat | aaatgcactc | aacttatata | tatttcagat | 1920 |
| ttggtagtgt | cttcaccgtt | ctatgtaaag | tagtgtggat | cctttacac | ccatctggat | 1980 |
| gggaaaaaaa | tgtgtgtccc | cttgaggata | taaactg | | | 2017 |

```
<210> SEQ ID NO 18
<211> LENGTH: 607
<212> TYPE: PRT
<213> ORGANISM: Arabidopsis Thaliana
```

<400> SEQUENCE: 18

```
Met Asp Thr Lys Ile Gly Ser Ile Asp Ala Cys Asn Pro Thr Asn His
 1               5                  10                  15

Asp Ile Gly Gly Pro Pro Asn Gly Gly Val Ser Thr Val Gln Asn Thr
             20                  25                  30

Ser Pro Leu His Ser Thr Thr Val Ser Pro Cys Asp Ala Thr Leu Gly
             35                  40                  45

Arg Tyr Leu Ala Arg Arg Leu Val Glu Ile Gly Val Thr Asp Val Phe
         50                  55                  60

Ser Val Pro Gly Asp Phe Asn Leu Thr Leu Leu Asp His Leu Ile Ala
 65                  70                  75                  80

Glu Pro Asn Leu Lys Leu Ile Gly Cys Cys Asn Glu Leu Asn Ala Gly
                 85                  90                  95

Tyr Ala Ala Asp Gly Tyr Ala Arg Ser Arg Gly Val Gly Ala Cys Val
             100                 105                 110

Val Thr Phe Thr Val Gly Gly Leu Ser Val Leu Asn Ala Ile Ala Gly
         115                 120                 125

Ala Tyr Ser Glu Asn Leu Pro Leu Ile Cys Ile Val Gly Gly Pro Asn
    130                 135                 140

Ser Asn Asp Tyr Gly Thr Asn Arg Ile Leu His His Thr Ile Gly Leu
145                 150                 155                 160

Pro Asp Phe Thr Gln Glu Leu Arg Cys Phe Gln Ala Val Thr Cys Phe
                165                 170                 175

Gln Ala Val Ile Asn Asn Leu Glu Glu Ala His Glu Leu Ile Asp Thr
            180                 185                 190

Ala Ile Ser Thr Ala Leu Lys Glu Ser Lys Pro Val Tyr Ile Ser Ile
        195                 200                 205

Ser Cys Asn Leu Pro Ala Ile Pro Leu Pro Thr Phe Ser Arg His Pro
    210                 215                 220

Val Pro Phe Met Leu Pro Met Lys Val Ser Asn Gln Ile Gly Leu Asp
225                 230                 235                 240

Ala Ala Val Glu Ala Ala Glu Phe Leu Asn Lys Ala Val Lys Pro
                245                 250                 255

Val Leu Val Gly Gly Pro Lys Met Arg Val Ala Lys Ala Ala Asp Ala
            260                 265                 270

Phe Val Glu Leu Ala Asp Ala Ser Gly Tyr Gly Leu Ala Val Met Pro
        275                 280                 285

Ser Ala Lys Gly Gln Val Pro Glu His His Lys His Phe Ile Gly Thr
    290                 295                 300

Tyr Trp Gly Ala Val Ser Thr Ala Phe Cys Ala Glu Ile Val Glu Ser
305                 310                 315                 320

Ala Asp Ala Tyr Leu Phe Ala Gly Pro Ile Phe Asn Asp Tyr Ser Ser
                325                 330                 335

Gly Gly Tyr Ser Leu Leu Lys Lys Glu Lys Ala Ile Ile Val Gln
            340                 345                 350

Pro Asp Arg Val Thr Ile Gly Asn Gly Pro Ala Phe Gly Cys Val Leu
        355                 360                 365

Met Lys Asp Phe Leu Ser Glu Leu Ala Lys Arg Ile Lys His Asn Asn
    370                 375                 380

Thr Ser Tyr Glu Asn Tyr His Arg Ile Tyr Val Pro Glu Gly Lys Pro
385                 390                 395                 400

Leu Arg Asp Asn Pro Asn Glu Ser Leu Arg Val Asn Val Leu Phe Gln
                405                 410                 415
```

-continued

His Ile Gln Asn Met Leu Ser Ser Glu Ser Ala Val Leu Ala Glu Thr
             420                 425                 430
Gly Asp Ser Trp Phe Asn Cys Gln Lys Leu Lys Leu Pro Glu Gly Cys
         435                 440                 445
Gly Tyr Glu Phe Gln Met Gln Tyr Gly Ser Ile Gly Trp Ser Val Gly
     450                 455                 460
Ala Thr Leu Gly Tyr Ala Gln Ala Met Pro Asn Arg Arg Val Ile Ala
465                 470                 475                 480
Cys Ile Gly Asp Gly Ser Leu Gln Val Thr Ala Gln Asp Val Ser Thr
                 485                 490                 495
Met Ile Arg Cys Gly Gln Lys Thr Ile Ile Phe Leu Ile Asn Asn Gly
             500                 505                 510
Gly Tyr Thr Ile Glu Val Glu Ile His Asp Gly Pro Tyr Asn Val Ile
         515                 520                 525
Lys Asn Trp Asn Tyr Thr Ala Phe Val Glu Ala Ile His Asn Gly Glu
     530                 535                 540
Gly Lys Cys Trp Thr Ala Lys Val Arg Cys Glu Glu Glu Leu Val Lys
545                 550                 555                 560
Ala Ile Asn Thr Ala Thr Asn Glu Glu Lys Glu Ser Phe Cys Phe Ile
                 565                 570                 575
Glu Val Ile Val His Lys Asp Asp Thr Ser Lys Glu Leu Leu Glu Trp
             580                 585                 590
Gly Ser Arg Val Ser Ala Ala Asn Ser Arg Pro Pro Asn Pro Gln
         595                 600                 605

<210> SEQ ID NO 19
<211> LENGTH: 1863
<212> TYPE: DNA
<213> ORGANISM: Arabidopsis Thaliana

<400> SEQUENCE: 19
gagagaagag gaggagaatt cgaagaataa aagataagaa ctttgacgtt ttgaagctta     60
aagcttgaaa cttgtttcat ccatggcggc tcgtagagtg tcttctcttt tatctcgatc    120
tttttcagct tcctctccct tactgtttcg ttctcaaggg agaaattgtt acaatggagg    180
gatcttaagg agatttggaa cctcttctgc tgctgctgag gaaatcataa acccatctgt    240
tcaagtttct cacacacagc tcctcatcaa tgggaacttt gttgactctg cttctggtaa    300
gacgtttccg actcttgatc cgaggacagg cgaagtcatt gctcatgtag ctgaaggcga    360
tgctgaagat atcaatcgag ctgtgaaagc tgcaaggacg gcctttgatg aaggaccttg    420
gcctaaaatg agtgcttatg aaaggtcaag agttttgttg aggtttgcag atttggttga    480
gaaacacagc gaagagctcg cgtctctaga cacatgggac aatggcaagc cttaccaaca    540
atccttgacc gcagagattc ccatgttttgc aagattgttc cgttactatg ctggatgggc    600
ggataagatt catggactaa caattccagc tgatggaaac tatcaagttc acacattaca    660
tgaaccgata ggtgtagctg acagatcat accgtgaat tttccactttt tgatgtttgc    720 ttggaaagtt ggtcctgctc ttgcttgtgg taacaccatt gtcctcaaaa ccgctgagca    780
aacacctctc acggctttct atgctggaaa gcttttcctt gaagcgggtc ttcctcctgg    840
tgttctgaat attgtttcgg gattcggtgc aacagcaggt gctgccctcg cgagtcatat    900
ggatgtagac aagcttgctt ttacaggatc gactgatacg gggaaagtta tacttggatt    960
ggctgctaac agcaatctta agcccgtaac tctggaactt ggagggaaat caccgttcat   1020

-continued

```
cgtattcgaa gatgctgata ttgataaagc tgtagagctt gcacactttg ccctcttctt    1080
caaccagggg caatgttgct gcgcggggtc tcggacattt gttcatgaga aagtgtatga    1140
tgagtttgtt gagaaatcaa aggcacgcgc attgaaacgt gttgttggtg atcctttcag    1200
gaaaggcatt gaacagggtc ctcagatcga tttgaagcaa tttgagaaag tgatgaagta    1260
cataaagtca ggtatcgaaa gcaatgctac tcttgaatgt ggtggtgatc agattggaga    1320
caaaggttac ttcatccaac ctactgtctt ctctaatgtt aaggatgaca tgcttatcgc    1380
tcaagacgag attttcggtc cagtccaatc gatcttgaag ttcagtgatg tggatgaggt    1440
gataaagagg gcgaacgaga cgaagtacgg gctagcggca ggggttttca cgaagaatct    1500
ggacacggca acagggttt caagggcttt gaaagctggt accgtatggg ttaactgctt    1560
cgacgtattt gatgcagcca taccatttgg tggttacaag atgagtggga atgggagaga    1620
gaaaggcata tacagtctca ataattactt gcagatcaag gcagtcgtca ctgctctaaa    1680
taagcctgcc tggatctgat ctctggagtg tggtttcagc atcataaatg ctcaaacaaa    1740
agaaatagac tctataaagt tacaatagta ataattaagg tcatggtttg taatttgagt    1800
aacggattgt gatacttcta ataaattttt cattgttgtt tattcatcaa aaaaaaaaaa    1860
aaa                                                                  1863
```

<210> SEQ ID NO 20
<211> LENGTH: 538
<212> TYPE: PRT
<213> ORGANISM: Arabidopsis Thaliana

<400> SEQUENCE: 20

```
Met Ala Ala Arg Arg Val Ser Ser Leu Leu Ser Arg Ser Phe Ser Ala
 1               5                  10                  15

Ser Ser Pro Leu Leu Phe Arg Ser Gln Gly Arg Asn Cys Tyr Asn Gly
             20                  25                  30

Gly Ile Leu Arg Arg Phe Gly Thr Ser Ala Ala Ala Glu Glu Ile
         35                  40                  45

Ile Asn Pro Ser Val Gln Val Ser His Thr Gln Leu Leu Ile Asn Gly
     50                  55                  60

Asn Phe Val Asp Ser Ala Ser Gly Lys Thr Phe Pro Thr Leu Asp Pro
 65                  70                  75                  80

Arg Thr Gly Glu Val Ile Ala His Val Ala Glu Gly Asp Ala Glu Asp
                 85                  90                  95

Ile Asn Arg Ala Val Lys Ala Ala Arg Thr Ala Phe Asp Glu Gly Pro
            100                 105                 110

Trp Pro Lys Met Ser Ala Tyr Glu Arg Ser Arg Val Leu Leu Arg Phe
        115                 120                 125

Ala Asp Leu Val Glu Lys His Ser Glu Glu Leu Ala Ser Leu Glu Thr
    130                 135                 140

Trp Asp Asn Gly Lys Pro Tyr Gln Gln Ser Leu Thr Ala Glu Ile Pro
145                 150                 155                 160

Met Phe Ala Arg Leu Phe Arg Tyr Tyr Ala Gly Trp Ala Asp Lys Ile
                165                 170                 175

His Gly Leu Thr Ile Pro Ala Asp Gly Asn Tyr Gln Val His Thr Leu
            180                 185                 190

His Glu Pro Ile Gly Val Ala Gly Gln Ile Ile Pro Trp Asn Phe Pro
        195                 200                 205

Leu Leu Met Phe Ala Trp Lys Val Gly Pro Ala Leu Ala Cys Gly Asn
    210                 215                 220
```

```
Thr Ile Val Leu Lys Thr Ala Glu Gln Thr Pro Leu Thr Ala Phe Tyr
225                 230                 235                 240

Ala Gly Lys Leu Phe Leu Glu Ala Gly Leu Pro Pro Gly Val Leu Asn
            245                 250                 255

Ile Val Ser Gly Phe Ala Thr Ala Gly Ala Ala Leu Ala Ser His
            260                 265                 270

Met Asp Val Asp Lys Leu Ala Phe Thr Gly Ser Thr Asp Thr Gly Lys
        275                 280                 285

Val Ile Leu Gly Leu Ala Ala Asn Ser Asn Leu Lys Pro Val Thr Leu
    290                 295                 300

Glu Leu Gly Gly Lys Ser Pro Phe Ile Val Phe Glu Asp Ala Asp Ile
305                 310                 315                 320

Asp Lys Ala Val Glu Leu Ala His Phe Ala Leu Phe Phe Asn Gln Gly
                325                 330                 335

Gln Cys Cys Cys Ala Gly Ser Arg Thr Phe Val His Glu Lys Val Tyr
            340                 345                 350

Asp Glu Phe Val Glu Lys Ser Lys Ala Arg Ala Leu Lys Arg Val Val
        355                 360                 365

Gly Asp Pro Phe Arg Lys Gly Ile Glu Gln Gly Pro Gln Ile Asp Leu
    370                 375                 380

Lys Gln Phe Glu Lys Val Met Lys Tyr Ile Lys Ser Gly Ile Glu Ser
385                 390                 395                 400

Asn Ala Thr Leu Glu Cys Gly Gly Asp Gln Ile Gly Asp Lys Gly Tyr
                405                 410                 415

Phe Ile Gln Pro Thr Val Phe Ser Asn Val Lys Asp Asp Met Leu Ile
            420                 425                 430

Ala Gln Asp Glu Ile Phe Gly Pro Val Gln Ser Ile Leu Lys Phe Ser
        435                 440                 445

Asp Val Asp Glu Val Ile Lys Arg Ala Asn Glu Thr Lys Tyr Gly Leu
    450                 455                 460

Ala Ala Gly Val Phe Thr Lys Asn Leu Asp Thr Ala Asn Arg Val Ser
465                 470                 475                 480

Arg Ala Leu Lys Ala Gly Thr Val Trp Val Asn Cys Phe Asp Val Phe
                485                 490                 495

Asp Ala Ala Ile Pro Phe Gly Gly Tyr Lys Met Ser Gly Asn Gly Arg
            500                 505                 510

Glu Lys Gly Ile Tyr Ser Leu Asn Asn Tyr Leu Gln Ile Lys Ala Val
        515                 520                 525

Val Thr Ala Leu Asn Lys Pro Ala Trp Ile
    530                 535

<210> SEQ ID NO 21
<211> LENGTH: 1614
<212> TYPE: DNA
<213> ORGANISM: Arabidopsis Thaliana

<400> SEQUENCE: 21
agagagagag agagaaatac aaagaaaaat aaatggagaa cggcaaatgc aacggagcca      60
cgacggtgaa gttaccggag atcaaattca ccaagctttt catcaacggc agttcattg     120 atgctgcttc aggaagacg tttgagacga tagaccctag gaacggtgaa gtgatcgcaa     180
caatagccga aggagacaaa gaagacgttg acttggccgt taacgctgca cgttacgcct     240
tcgaccatgg tccttggcct cgcatgaccg gcttcgagag ggcaaagctt ataaacaaat     300
```

-continued

```
tcgcagactt aatagaggaa aacattgaag aattggctaa acttgatgcg gttgacggtg    360
gaaaattgtt ccaattgggg aaatatgctg atattccggc cacagccggt cattttcgat    420
acaatgcggg tgcagcggat aaaatccacg gcgagactct taaaatgacg cgtcaatcgt    480
tgtttggata caccctcaaa gaaccaattg gagtggttgg taatatcatc ccttggaatt    540
tcccaagcat tatgtttgcc acaaaggtag ctccggctat ggctgctggt tgcaccatgg    600
tggtcaagcc agctgaacag acttcactct ctgctttgtt ctatgcccat ctctcaaaag    660
aagcgggaat tcctgatggt gtgctcaaca ttgtaactgg ttttggatca actgctggag    720
ctgccattgc ctcccatatg gacgtagaca agttagtttt cactgggtca acagatgttg    780
gaaggaagat aatgcaagcc gcagccgcaa gtaatctcaa aaagtttcc cttgaattag     840 gcgggaaatc gccacttctc atattcaacg acgctgatat tgacaaagcc gccgatcttg    900
cgcttctcgg ttgctttttac aacaagggtg aaatttgcgt ggcgagctct cgtgtgtttg    960
ttcaagaagg tatatacgat aaggttgtgg agaagttagt agagaaggct aaagattgga   1020
ccgttggtga tccttttgat tccactgctc gacaaggacc tcaagtggat aaaagacagt   1080
ttgagaagat tctatcttac attgagcacg gtaaaaacga aggagcgacc ttattaactg   1140
gaggaaaagc cattggagac aaaggatatt tcatccaacc aactatattc gcagatgtca   1200
ctgaggatat gaagatatac caagatgaaa tctttggacc agtcatgtca ctgatgaaat   1260
tcaagacggt agaggaaggg atcaaatgcg caaacaacac gaaatacggt cttgcagcag   1320
gaatactaag ccaagacata gacttgatca acacggtttc gaggtcaatc aaagctggaa   1380
tcatttgggt taattgctac ttcgggtttg atcttgactg tccttatggt ggctacaaga   1440
tgagtggtaa ttgtcgtgaa agtggcatgg acgctctcga caactatcta caaaccaaat   1500
ccgtcgttat gcctcttcac aattcccctt ggatgtaata aaattgtcca taacacatag   1560
aaaaaaactt aatccaatga taataaggcg gcttgaatta aaaaaaaaaa aaaa          1614
```

<210> SEQ ID NO 22
<211> LENGTH: 501
<212> TYPE: PRT
<213> ORGANISM: Arabidopsis Thaliana

<400> SEQUENCE: 22

```
Met Glu Asn Gly Lys Cys Asn Gly Ala Thr Thr Val Lys Leu Pro Glu
  1               5                  10                  15

Ile Lys Phe Thr Lys Leu Phe Ile Asn Gly Gln Phe Ile Asp Ala Ala
             20                  25                  30

Ser Gly Lys Thr Phe Glu Thr Ile Asp Pro Arg Asn Gly Glu Val Ile
         35                  40                  45

Ala Thr Ile Ala Glu Gly Asp Lys Glu Asp Val Asp Leu Ala Val Asn
     50                  55                  60

Ala Ala Arg Tyr Ala Phe Asp His Gly Pro Trp Pro Arg Met Thr Gly
 65                  70                  75                  80

Phe Glu Arg Ala Lys Leu Ile Asn Lys Phe Ala Asp Leu Ile Glu Glu
                 85                  90                  95

Asn Ile Glu Glu Leu Ala Lys Leu Asp Ala Val Asp Gly Gly Lys Leu
            100                 105                 110

Phe Gln Leu Gly Lys Tyr Ala Asp Ile Pro Ala Thr Ala Gly His Phe
        115                 120                 125

Arg Tyr Asn Ala Gly Ala Ala Asp Lys Ile His Gly Glu Thr Leu Lys
    130                 135                 140
```

-continued

```
Met Thr Arg Gln Ser Leu Phe Gly Tyr Thr Leu Lys Glu Pro Ile Gly
145                 150                 155                 160

Val Val Gly Asn Ile Ile Pro Trp Asn Phe Pro Ser Ile Met Phe Ala
                165                 170                 175

Thr Lys Val Ala Pro Ala Met Ala Ala Gly Cys Thr Met Val Val Lys
            180                 185                 190

Pro Ala Glu Gln Thr Ser Leu Ser Ala Leu Phe Tyr Ala His Leu Ser
        195                 200                 205

Lys Glu Ala Gly Ile Pro Asp Gly Val Leu Asn Ile Val Thr Gly Phe
    210                 215                 220

Gly Ser Thr Ala Gly Ala Ala Ile Ala Ser His Met Asp Val Asp Lys
225                 230                 235                 240

Val Ser Phe Thr Gly Ser Thr Asp Val Gly Arg Lys Ile Met Gln Ala
                245                 250                 255

Ala Ala Ala Ser Asn Leu Lys Lys Val Ser Leu Glu Leu Gly Gly Lys
            260                 265                 270

Ser Pro Leu Leu Ile Phe Asn Asp Ala Asp Ile Asp Lys Ala Ala Asp
        275                 280                 285

Leu Ala Leu Leu Gly Cys Phe Tyr Asn Lys Gly Glu Ile Cys Val Ala
    290                 295                 300

Ser Ser Arg Val Phe Val Gln Glu Gly Ile Tyr Asp Lys Val Val Glu
305                 310                 315                 320

Lys Leu Val Glu Lys Ala Lys Asp Trp Thr Val Gly Asp Pro Phe Asp
                325                 330                 335

Ser Thr Ala Arg Gln Gly Pro Gln Val Asp Lys Arg Gln Phe Glu Lys
            340                 345                 350

Ile Leu Ser Tyr Ile Glu His Gly Lys Asn Glu Gly Ala Thr Leu Leu
        355                 360                 365

Thr Gly Gly Lys Ala Ile Gly Asp Lys Gly Tyr Phe Ile Gln Pro Thr
    370                 375                 380

Ile Phe Ala Asp Val Thr Glu Asp Met Lys Ile Tyr Gln Asp Glu Ile
385                 390                 395                 400

Phe Gly Pro Val Met Ser Leu Met Lys Phe Lys Thr Val Glu Glu Gly
                405                 410                 415

Ile Lys Cys Ala Asn Asn Thr Lys Tyr Gly Leu Ala Ala Gly Ile Leu
            420                 425                 430

Ser Gln Asp Ile Asp Leu Ile Asn Thr Val Ser Arg Ser Ile Lys Ala
        435                 440                 445

Gly Ile Ile Trp Val Asn Cys Tyr Phe Gly Phe Asp Leu Asp Cys Pro
    450                 455                 460

Tyr Gly Gly Tyr Lys Met Ser Gly Asn Cys Arg Glu Ser Gly Met Asp
465                 470                 475                 480

Ala Leu Asp Asn Tyr Leu Gln Thr Lys Ser Val Val Met Pro Leu His
                485                 490                 495

Asn Ser Pro Trp Met
            500
```

<210> SEQ ID NO 23
<211> LENGTH: 1772
<212> TYPE: DNA
<213> ORGANISM: Arabidopsis Thaliana
<220> FEATURE:
<221> NAME/KEY: exon
<222> LOCATION: (1)..(834)
<221> NAME/KEY: exon
<222> LOCATION: (836)..(930)

```
<221> NAME/KEY: exon
<222> LOCATION: (932)..(939)
<221> NAME/KEY: exon
<222> LOCATION: (941)..(1772)

<400> SEQUENCE: 23
caaaaaagtt agccatggca tcaagaagag tttcttcgct gctctctcgc tctttcatgt      60
cctcctcacg ttctatcttc tctcttagag gcatgaacag aggagctcaa agatacagta    120
acctcgctgc tgctgtcgaa aacactatta ctccaccagt gaaagttgaa cacacacagc    180
ttctaatcgg tggaagattc gttgatgcag tgtcaggaaa aactttccct actttggatc    240
caagaaatgg agaagtgatt gctcaagtgt ctgaaggtga tgcagaagac gtgaaccgcg    300
cggttgcagc tgcacgaaag gcttttgatg aaggaccatg gcctaaaatg acagcttatg    360
agagatcaaa gatactgttt cgtttcgctg atttaatcga gaaacataat gatgagattg    420
ctgctcttga gacttgggat aatgggaaac cttatgaaca atctgctcaa attgaagtac    480
caatgcttgc tagggtgttc cggtactatg ctggttgggc agacaagata catggaatga    540
caatgccagg agatggtcca caccatgtgc agaccttaca tgagcctata ggagtcgctg    600
gacaaatcat cccatggaac ttccctcttc tcatgctttc ttggaaactt ggaccagctt    660
tagcttgcgg taacaccgtt gttctcaaaa ctgctgagca aactcctcta tctgctcttc    720
ttgttgggaa actacttcat gaggctggac ttcctgatgg agttgtgaat atagtttctg    780
gatttggggc tactgctggt gcagctatag ctagtcacat ggacgttgat aaggttgctt    840
tcaccgggtc tactgatgtt gggaagatta ttcttgagtt agcttcaaaa agcaacctta    900
aggcagtgac tcttgagctg gaggaaagtc accattcatt tgtatgtgaa gatgctgatg    960
tggatcaggc cgttgagctt gcacatttcg ctttgttctt taaccaggga caatgttgtt   1020
gtgctggttc gcgtacattt gtacatgaac gtgtgtatga tgagtttgta gagaaagcta   1080
aagctcgtgt actcaagcga aatgttggag atcccttcaa gtcaggcatt gagcaaggtc   1140
cccaggtaga ctcagagcaa ttcaacaaaa tcctgaagta catcaaacat ggagttgagg   1200
ctggagccac attacaagct ggaggtgaca ggcttggttc caagggttac tacattcaac   1260
ctactgtctt ctcagatgtg aaagatgaca tgctcatagc aacagacgag attttcgggc   1320
cggttcaaac catactgaaa ttcaaggatc ttgatgaggt gattgcaagg gccaacaact   1380
caaggtacgg tttagctgct ggagtgttca cacagaatct tgacacagca caccggctga   1440
tgcgagcact cagagttggg actgtttgga tcaactgttt tgatgtactt gatgcatcaa   1500
ttccatttgg agggtataag atgagtggca ttggtagaga gaaaggtatc tacagtctca   1560
acaattactt gcaagtcaag gctgttgtta cttccctcaa gaaccctgcc tggctctaaa   1620
ccataccagg tggttacact tatttctcga gtttggttta tgatttgcac ttttgctttg   1680
aaaacctgga gttgtactgt gtctctagga tttctagatt ttgagagtaa tttatcttca   1740
atacattttg caataaagct acatgacaat gg                                  1772

<210> SEQ ID NO 24
<211> LENGTH: 534
<212> TYPE: PRT
<213> ORGANISM: Arabidopsis Thaliana

<400> SEQUENCE: 24

Met Ala Ser Arg Arg Val Ser Ser Leu Leu Ser Arg Ser Phe Met Ser
 1               5                  10                  15

Ser Ser Arg Ser Ile Phe Ser Leu Arg Gly Met Asn Arg Gly Ala Gln
```

-continued

```
                20                  25                  30
Arg Tyr Ser Asn Leu Ala Ala Val Glu Asn Thr Ile Thr Pro Pro
            35                  40                  45

Val Lys Val Glu His Thr Gln Leu Leu Ile Gly Gly Arg Phe Val Asp
 50                  55                  60

Ala Val Ser Gly Lys Thr Phe Pro Thr Leu Asp Pro Arg Asn Gly Glu
 65                  70                  75                  80

Val Ile Ala Gln Val Ser Glu Gly Asp Ala Glu Asp Val Asn Arg Ala
                85                  90                  95

Val Ala Ala Ala Arg Lys Ala Phe Asp Glu Gly Pro Trp Pro Lys Met
            100                 105                 110

Thr Ala Tyr Glu Arg Ser Lys Ile Leu Phe Arg Phe Ala Asp Leu Ile
            115                 120                 125

Glu Lys His Asn Asp Glu Ile Ala Ala Leu Glu Thr Trp Asp Asn Gly
            130                 135                 140

Lys Pro Tyr Glu Gln Ser Ala Gln Ile Glu Val Pro Met Leu Ala Arg
145                 150                 155                 160

Val Phe Arg Tyr Tyr Ala Gly Trp Ala Asp Lys Ile His Gly Met Thr
                165                 170                 175

Met Pro Gly Asp Gly Pro His His Val Gln Thr Leu His Glu Pro Ile
            180                 185                 190

Gly Val Ala Gly Gln Ile Ile Pro Trp Asn Phe Pro Leu Leu Met Leu
            195                 200                 205

Ser Trp Lys Leu Gly Pro Ala Leu Ala Cys Gly Asn Thr Val Val Leu
    210                 215                 220

Lys Thr Ala Glu Gln Thr Pro Leu Ser Ala Leu Leu Val Gly Lys Leu
225                 230                 235                 240

Leu His Glu Ala Gly Leu Pro Asp Gly Val Val Asn Ile Val Ser Gly
                245                 250                 255

Phe Gly Ala Thr Ala Gly Ala Ala Ile Ala Ser His Met Asp Val Asp
            260                 265                 270

Lys Val Ala Phe Thr Gly Ser Thr Asp Val Gly Lys Ile Ile Leu Glu
            275                 280                 285

Leu Ala Ser Lys Ser Asn Leu Lys Ala Val Thr Leu Glu Leu Glu Glu
290                 295                 300

Ser His His Ser Phe Val Cys Glu Asp Ala Asp Val Asp Gln Ala Val
305                 310                 315                 320

Glu Leu Ala His Phe Ala Leu Phe Phe Asn Gln Gly Gln Cys Cys Cys
                325                 330                 335

Ala Gly Ser Arg Thr Phe Val His Glu Arg Val Tyr Asp Glu Phe Val
            340                 345                 350

Glu Lys Ala Lys Ala Arg Ala Leu Lys Arg Asn Val Gly Asp Pro Phe
            355                 360                 365

Lys Ser Gly Ile Glu Gln Gly Pro Gln Val Asp Ser Glu Gln Phe Asn
            370                 375                 380

Lys Ile Leu Lys Tyr Ile Lys His Gly Val Glu Ala Gly Ala Thr Leu
385                 390                 395                 400

Gln Ala Gly Gly Asp Arg Leu Gly Ser Lys Gly Tyr Tyr Ile Gln Pro
                405                 410                 415

Thr Val Phe Ser Asp Val Lys Asp Asp Met Leu Ile Ala Thr Asp Glu
            420                 425                 430

Ile Phe Gly Pro Val Gln Thr Ile Leu Lys Phe Lys Asp Leu Asp Glu
            435                 440                 445
```

```
Val Ile Ala Arg Ala Asn Asn Ser Arg Tyr Gly Leu Ala Ala Gly Val
    450                 455                 460

Phe Thr Gln Asn Leu Asp Thr Ala His Arg Leu Met Arg Ala Leu Arg
465                 470                 475                 480

Val Gly Thr Val Trp Ile Asn Cys Phe Asp Val Leu Asp Ala Ser Ile
                485                 490                 495

Pro Phe Gly Gly Tyr Lys Met Ser Gly Ile Gly Arg Glu Lys Gly Ile
            500                 505                 510

Tyr Ser Leu Asn Asn Tyr Leu Gln Val Lys Ala Val Val Thr Ser Leu
        515                 520                 525

Lys Asn Pro Ala Trp Leu
    530

<210> SEQ ID NO 25
<211> LENGTH: 1718
<212> TYPE: DNA
<213> ORGANISM: Arabidopsis Thaliana
<220> FEATURE:
<221> NAME/KEY: exon
<222> LOCATION: (1)..(942)
<221> NAME/KEY: exon
<222> LOCATION: (944)..(1453)
<221> NAME/KEY: exon
<222> LOCATION: (1455)..(1558)
<221> NAME/KEY: exon
<222> LOCATION: (1560)..(1620)
<221> NAME/KEY: exon
<222> LOCATION: (1622)..(1718)

<400> SEQUENCE: 25
aacaaacaag gtctagcttt ttataaccaa actctgcttc tgaacagagt tagtcaaaga      60
gagagaagcc atggaagcta tgaaggagac tgtggaggag agcttgagag agatgagaga     120
gacgtttgcg agtgggagga cgaggagtct gaagtggagg aaggcacaga tcggagctat     180
atacgagatg gttaaagaca acgaagacaa gatctgcaat gctctgtttc aagatttggg     240
caaacacagt actgaagctt ttagagatga gcttggtgtt gtcttgcgaa cagctactgt     300
tgcaatcaac tgtcttgata atgggccgt ccccaaacat agcaaacttc ctctgttgtt     360
ctacccagca aaagggaaag tcatatcgga accctatggg acggttcttg ttctgtctag     420
ctggaatttt cctatatctt tgtctctgga tccattgatt ggggcaatag cagcaggaaa     480
taccgtgctt tcaagtcat ctgaactaag ccctaacgca tctgccttcc ttgccaagac     540
aattccagct tatctcgata ctaaagccat caaagttatc gaaggaggac ctgatgtcgc     600
tactatcctc ttgcagcatc aatgggacaa gatcttcttc accggagtc ccaagattgg     660 aaggatcata atggctgcag cagcacagca tctgactcct gtgacattgg agcttggtgg     720
aaaatgtccc accattgttg atcatcacac catttcaaag aacatcaagt cggttgtcaa     780
gaggattgct ggaggaaaat ggggatcttg caatggacaa gcttgtatct ctgtagatta     840
cgttcttatc gaaagagtt tcgcgcctac tctgattgat atgttgaagc tacgataaa     900 gtctttcttt ggcgaaaatc ctaaagaatc tggatgtctc tcaaggattg caaacaagca     960
ccacgttcag agactgtctc gtcttcttag cgatcctcgt gtccaagctt ccatcgtcta    1020
tggtggttct atagacgaag ataagctgta tgttgagcca acgatcttgt ggaccctcc    1080 tcttgattct gagatcatga atgaagagat ctttggtcca attctcccga ttatcacggt    1140
acgtgacatc caagaaagca tagggatcat aatacaaaaa ccgaagccac ttgccattta    1200
tgcattcaca aatgacgaga accttaaaac tagaattttg tcagaaacat cctcaggaag    1260
```

```
tgttaccttc aatgacgtca tgatccagta tatgtgtgat gcgttacctt ttggaggagt    1320
gggagaaagt ggaataggga ggtatcacgg gaaatactca tttgattgtt tcagtcacga    1380
gaaagcaata atggaaggaa gcttaggtat ggatcttgaa gctcgatacc ctccatggaa    1440
caacttcaag ctcaccttca tcagactcgc atttcgtgaa gcttacttca agcttatcct    1500
ccttatgctt ggtcttaaaa gataaaaggg ggaaagtgag agacagagac acatacacac    1560
aaacagagac aatataagtg attgaattac atcacactta tgtttgctta tcatatcttc    1620
acctaataag tctcattccg aatgttttac atttctttca agcttgagag attctatata    1680
aagtgatttg atatctaaaa aaaaaaaaaa aaaaaaaa                            1718
```

<210> SEQ ID NO 26
<211> LENGTH: 433
<212> TYPE: PRT
<213> ORGANISM: Arabidopsis Thaliana

<400> SEQUENCE: 26

```
Met Glu Ala Met Lys Glu Thr Val Glu Glu Ser Leu Arg Glu Met Arg
  1               5                  10                  15

Glu Thr Phe Ala Ser Gly Arg Thr Arg Ser Leu Lys Trp Arg Lys Ala
                 20                  25                  30

Gln Ile Gly Ala Ile Tyr Glu Met Val Lys Asp Asn Glu Asp Lys Ile
             35                  40                  45

Cys Asn Ala Leu Phe Gln Asp Leu Gly Lys His Ser Thr Glu Ala Phe
         50                  55                  60

Arg Asp Glu Leu Gly Val Val Leu Arg Thr Ala Thr Val Ala Ile Asn
 65                  70                  75                  80

Cys Leu Asp Lys Trp Ala Val Pro Lys His Ser Lys Leu Pro Leu Leu
                 85                  90                  95

Phe Tyr Pro Ala Lys Gly Lys Val Ile Ser Glu Pro Tyr Gly Thr Val
                100                 105                 110

Leu Val Leu Ser Ser Trp Asn Phe Pro Ile Ser Leu Ser Leu Asp Pro
            115                 120                 125

Leu Ile Gly Ala Ile Ala Ala Gly Asn Thr Val Leu Leu Lys Ser Ser
        130                 135                 140

Glu Leu Ser Pro Asn Ala Ser Ala Phe Leu Ala Lys Thr Ile Pro Ala
145                 150                 155                 160

Tyr Leu Asp Thr Lys Ala Ile Lys Val Ile Glu Gly Gly Pro Asp Val
                165                 170                 175

Ala Thr Ile Leu Leu Gln His Gln Trp Asp Lys Ile Phe Phe Thr Gly
            180                 185                 190

Ser Pro Lys Ile Gly Arg Ile Ile Met Ala Ala Ala Ala Gln His Leu
        195                 200                 205

Thr Pro Val Thr Leu Glu Leu Gly Gly Lys Ser Cys Ile Ser Val Asp
    210                 215                 220

Tyr Val Leu Ile Glu Lys Ser Phe Ala Pro Thr Leu Ile Asp Met Leu
225                 230                 235                 240

Lys Pro Thr Ile Lys Ser Phe Phe Gly Glu Asn Pro Lys Glu Ser Gly
                245                 250                 255

Cys Leu Ser Arg Ile Ala Asn Lys His His Val Gln Arg Leu Ser Arg
            260                 265                 270

Leu Leu Ser Asp Pro Arg Pro Thr Ile Leu Leu Asp Pro Pro Leu Asp
        275                 280                 285
```

```
Ser Glu Ile Met Asn Glu Ile Phe Gly Pro Ile Leu Pro Ile Ile
    290                 295                 300

Thr Val Arg Asp Ile Gln Glu Ser Ile Gly Ile Ile Asn Thr Lys Pro
305                 310                 315                 320

Lys Pro Leu Ala Ile Tyr Ala Phe Thr Asn Asp Glu Asn Leu Lys Thr
                325                 330                 335

Arg Ile Leu Ser Glu Thr Ser Ser Gly Ser Val Thr Phe Asn Asp Val
            340                 345                 350

Met Ile Gln Tyr Met Cys Asp Ala Leu Pro Phe Gly Val Gly Glu
        355                 360                 365

Ser Gly Ile Gly Arg Tyr His Gly Lys Tyr Ser Phe Asp Cys Phe Ser
    370                 375                 380

His Glu Lys Ala Ile Met Glu Gly Ser Leu Gly Met Asp Leu Glu Ala
385                 390                 395                 400

Arg Tyr Pro Pro Trp Asn Asn Phe Lys Leu Thr Phe Ile Arg Leu Ala
                405                 410                 415

Phe Arg Glu Ala Tyr Phe Lys Leu Ile Leu Leu Met Leu Gly Leu Lys
                420                 425                 430

Arg
```

<210> SEQ ID NO 27
<211> LENGTH: 2205
<212> TYPE: DNA
<213> ORGANISM: Arabidopsis Thaliana

<400> SEQUENCE: 27

```
aaactccgcc tccgtttgtt ggctatttac actcactctg tctccgccgg tagatttgtc      60
agctgcgtct tcctcgtttt ctctctctct gtctgtgtct cttagaatgc aatcagctat     120
ggcgctttcg ttctcccaga cgtcgtttac aagaccaaac cacgtgctcg atcatctgg      180
ttctgttttc tctacgccca gaagtctccg gttctgcgga ctccggcggg aagcgtttgg     240
tttctcaacg tcgaatcagt tggctattcg cagtaaccga atccaatttc taagtaggaa     300
gtcattccaa gtcccgcctt ctgcttcaag taatggtaat ggcgctccac cgaaatcttt     360
cgattacgat ttgatcatca tcggagctgg agttggtggc cacggagctg ctttgcacgc     420
cgttgaaaag ggacttaaaa cagccattat tgaaggagat gttgttggag ggacttgtgt     480
taacagagga tgtgtgcctt ctaaagctct tcttgctgtt agtggtcgaa tgcgggaact     540
tcagaacgaa catcacatga agtccttttgg tctccaggtt tcagctgctg gatatgatcg     600
tcagggtgtg gcagatcatg ctaataatct ggctaccaaa atacgaaaca atctgaccaa     660
ttcaatgaag gcaattggtg ttgacatatt gactggatttt ggcagtgttc tgggtccaca     720
aaaggttaaa tatgggaagg acaatattat tactgcaaaa gatataatca ttgccactgg     780
atctgtgccg tttgtcccta aggaattgaa gttgatgga aagactgtga tcaccagtga     840
ccatgctttg aaattagagt ctgtccctga gtggattgca attgtaggaa gtggttatat     900
tggtcttgag ttcagtgatg tttacacagc tcttggaagt gaggtaactt ttatagaagc     960
actggatcag ctaatgcctg gatttgatcc tgagatcagt aagctagctc agagggtttt    1020
gataaatcca agaagattg actatcatac tggagtcttt gcaagcaaaa ttactccggc    1080
aagggatggg aaaccagttc tgattgagct tattgatgcc aaaaccaagg aacctaagga    1140
tactttggag gtagatgctg ctcttattgc tactgggaga gctccattca ccaatggact    1200
tggcttggaa aatgtcaatg ttgtgacgca gagaggtttt ataccagttg atgagcgaat    1260
```

-continued

```
gcgtgtgatc gatggaaagg ggactctggt tccgaacttg tactgcattg gtgatgccaa      1320
tggtaaattg atgcttgcac atgcagccag tgcccaagga atttctgtgg tcgagcaagt      1380
cagcggcaga gatcatgtgc ttaatcatct tagcatccca gctgcttgct ttactcatcc      1440
tgaaatcagc atggtgggat taacagagcc tcaagcaaaa gaaaaggcg agaaggaagg       1500 atttaaagtt agtgttgtca agacaagttt caaggctaac acaaaggccc tagctgaaaa      1560
tgaaggagaa ggaatagcta agatgatata ccgacctgac aatggtgaaa tcttaggagt      1620
tcatatattt ggactgcatg cagctgacct tatccatgaa gcttctaatg cgattgctct      1680
aggaacgcgt attcaggaca taaaattggc agttcatgca catccaacac tctctgaggt      1740
cctcgacgaa ctgttcaaag cagccaaggt tgaaagtcat gctacgacaa ggacagtaag      1800 tgaaaagtg gttgtataat aagaaaccaa aaacttattg gggtggggag aaacatcttg       1860
aagaaagaaa atttgtgatt gtactttagg gagatgcaaa gataaagcta aacacgaacc      1920
aggaagatcg aaaggaaga agaagaggag gagatgatga gaaacaacct tccgtaagta       1980
aagacttgaa agatatatct acaaggcctt cttctttctt tgagaatatt tctgttggag      2040
tcttgtctct gctttcactt atatttgttt aattgttcca tggtttcaat tagtggagat      2100
tgtggttttg gttattgtat gtttgtttga tgtgaacgat tttggatgat tcttctcttt      2160
ttactagtaa aatcacttgt ctgtcaaaaa aaaaaaaaaa aaaaa                      2205
```

<210> SEQ ID NO 28
<211> LENGTH: 570
<212> TYPE: PRT
<213> ORGANISM: Arabidopsis Thaliana

<400> SEQUENCE: 28

```
Met Gln Ser Ala Met Ala Leu Ser Phe Ser Gln Thr Ser Phe Thr Arg
  1               5                  10                  15

Pro Asn His Val Leu Gly Ser Ser Gly Ser Val Phe Ser Thr Pro Arg
             20                  25                  30

Ser Leu Arg Phe Cys Gly Leu Arg Arg Glu Ala Phe Gly Phe Ser Thr
         35                  40                  45

Ser Asn Gln Leu Ala Ile Arg Ser Asn Arg Ile Gln Phe Leu Ser Arg
     50                  55                  60

Lys Ser Phe Gln Val Ser Ala Ser Ala Ser Asn Gly Asn Gly Ala
 65                  70                  75                  80

Pro Pro Lys Ser Phe Asp Tyr Asp Leu Ile Ile Gly Ala Gly Val
                 85                  90                  95

Gly Gly His Gly Ala Ala Leu His Ala Val Glu Lys Gly Leu Lys Thr
                100                 105                 110

Ala Ile Ile Glu Gly Asp Val Val Gly Gly Thr Cys Val Asn Arg Gly
            115                 120                 125

Cys Val Pro Ser Lys Ala Leu Leu Ala Val Ser Gly Arg Met Arg Glu
        130                 135                 140

Leu Gln Asn Glu His His Met Lys Ser Phe Gly Leu Gln Val Ser Ala
145                 150                 155                 160

Ala Gly Tyr Asp Arg Gln Gly Val Ala Asp His Ala Asn Asn Leu Ala
                165                 170                 175

Thr Lys Ile Arg Asn Asn Leu Thr Asn Ser Met Lys Ala Ile Gly Val
            180                 185                 190

Asp Ile Leu Thr Gly Phe Gly Ser Val Leu Gly Pro Gln Lys Val Lys
        195                 200                 205
```

```
Tyr Gly Lys Asp Asn Ile Ile Thr Ala Lys Asp Ile Ile Ala Thr
        210                 215                 220

Gly Ser Val Pro Phe Val Pro Lys Gly Ile Glu Val Asp Gly Lys Thr
225                 230                 235                 240

Val Ile Thr Ser Asp His Ala Leu Lys Leu Glu Ser Val Pro Glu Trp
                245                 250                 255

Ile Ala Ile Val Gly Ser Gly Tyr Ile Gly Leu Glu Phe Ser Asp Val
            260                 265                 270

Tyr Thr Ala Leu Gly Ser Glu Val Thr Phe Ile Glu Ala Leu Asp Gln
        275                 280                 285

Leu Met Pro Gly Phe Asp Pro Glu Ile Ser Lys Leu Ala Gln Arg Val
290                 295                 300

Leu Ile Asn Pro Arg Lys Ile Asp Tyr His Thr Gly Val Phe Ala Ser
305                 310                 315                 320

Lys Ile Thr Pro Ala Arg Asp Gly Lys Pro Val Leu Ile Glu Leu Ile
                325                 330                 335

Asp Ala Lys Thr Lys Glu Pro Lys Asp Thr Leu Glu Val Asp Ala Ala
            340                 345                 350

Leu Ile Ala Thr Gly Arg Ala Pro Phe Thr Asn Gly Leu Gly Leu Glu
        355                 360                 365

Asn Val Asn Val Val Thr Gln Arg Gly Phe Ile Pro Val Asp Glu Arg
370                 375                 380

Met Arg Val Ile Asp Gly Lys Gly Thr Leu Val Pro Asn Leu Tyr Cys
385                 390                 395                 400

Ile Gly Asp Ala Asn Gly Lys Leu Met Leu Ala His Ala Ala Ser Ala
                405                 410                 415

Gln Gly Ile Ser Val Val Glu Gln Val Ser Gly Arg Asp His Val Leu
            420                 425                 430

Asn His Leu Ser Ile Pro Ala Ala Cys Phe Thr His Pro Glu Ile Ser
        435                 440                 445

Met Val Gly Leu Thr Glu Pro Gln Ala Lys Glu Lys Gly Glu Lys Glu
450                 455                 460

Gly Phe Lys Val Ser Val Lys Thr Ser Phe Lys Ala Asn Thr Lys
465                 470                 475                 480

Ala Leu Ala Glu Asn Glu Gly Glu Gly Ile Ala Lys Met Ile Tyr Arg
                485                 490                 495

Pro Asp Asn Gly Glu Ile Leu Gly Val His Ile Phe Gly Leu His Ala
            500                 505                 510

Ala Asp Leu Ile His Glu Ala Ser Asn Ala Ile Ala Leu Gly Thr Arg
        515                 520                 525

Ile Gln Asp Ile Lys Leu Ala Val His Ala His Pro Thr Leu Ser Glu
530                 535                 540

Val Leu Asp Glu Leu Phe Lys Ala Ala Lys Val Glu Ser His Ala Thr
545                 550                 555                 560

Thr Arg Thr Val Ser Glu Lys Val Val Val
                565                 570
```

<210> SEQ ID NO 29
<211> LENGTH: 2120
<212> TYPE: DNA
<213> ORGANISM: Arabidopsis Thaliana

<400> SEQUENCE: 29
cacacgtgtc ggagtctgcc gtttgaactg ttcgccgttc tccttcccca cgtggctctc        60

-continued

```
acaagataac gtcaggcaga ccgagaaata aaaggcccaa tgggctcaga gttggatatt      120
atagccggga attttgaaat ctccggttta aagacgagaa acgtgacacg tgtcatctcc      180
gctttgatat ctccgcctcc gctcgtcgag tgagactagt acagacttgt catctccgtc      240
actccctttt tctctacaca gatctctcat tcactctctc gtacacaatg caatcggttc      300
tttctctttc cttctcacaa gcatcgcttc ctttagcgaa tcgtacgctt tgttcatcca      360
acgcagctcc ttctacgccg agaaatctcc ggttctgtgg actccggcga aagcgtttt       420 gcttctctcc gtcgaagcaa ttgacctcgt gccgtttcca tattcagagt aggagaatcg      480
aagtctccgc cgctgcttct tcttccgctg aaatggagc tccatcgaaa tcattcgatt       540
atgatttgat cattatcgga gctggagttg gtggccatgg agctgcattg cacgccgtcg      600
agaagggact caaaactgct atcattgaag agatgttgt tggaggtact tgcgttaaca       660
gaggctgtgt gccttccaaa gctctacttg ctgttagtgg taggatgagg gaactccaga      720
acgaacatca catgaaggct tttggttgc aggtttcagc tgctggttat gaccgccaag       780
gtgtggctga ccacgcaagt aacctggcta ccaaaattag gaataatctc accaattcta      840
tgaaggcact tggtgttgac atattgacag gttttggcgc tgttctgggc ccacaaaagg      900
ttaaatatgg tgacaatatt atcaccggaa agatataat catcgcaact ggatctgtac       960
cgttcgtccc gaaaggaatt gaagttgatg gaaagactgt tatcacaagt gatcatgcat     1020
tgaaattgga gtccgttcct gactggattg cgatagtagg aagtggttat atcggtcttg     1080
agttcagtga tgtttacacg gcccttggaa gtgaggtaac ttttattgag gcactggatc     1140
aactaatgcc tggatttgat cctgagatca gtaagctggc tcaaagggtt ctaataaata     1200
caagaaaaat tgactaccat actggagtat ttgcaagcaa aatcactcca gcaaaggatg     1260
ggaaaccagt gctgattgaa ctaattgatg ccaaaaccaa ggaacccaag gatactttgg     1320
aggttgacgc tgctctaatt gctactggaa gagctccatt caccaatggt cttggcctgg     1380
aaaatatcaa tgttaccaca caaagaggtt ttataccagt tgatgagcga atgcgtgtta     1440
ttgatggaaa tggaaagctg gttccccact tgtactgcat cggtgatgcc aatggtaaac     1500
tgatgcttgc tcatgcagct agtgctcaag gaatttctgt ggtggagcaa gtcacaggta     1560
gagatcatgt gcttaatcat cttagcatcc cagctgcttg ttttactcat cctgaaataa     1620
gtatggtggg attgacagag cctcaagcga gagagaaagc tgagaaagag ggattcaaag     1680
taagtatcgc caagacaagt ttcaaggcaa acacaaaggc cctagccgaa aatgaaggag     1740
aaggactcgc taagatgata tacagacctg acaatggtga aatccttgga gttcatatat     1800
ttggattgca tgctgctgat cttatccatg aagcatcaaa cgcgattgct ttaggaacac     1860
gtattcagga cataaaactt gctgttcatg cacatccaac actgtctgaa gttgtagacg     1920
aactgtttaa agcagccaag gtcgatagtc cagcttcagt aacagcacaa agtgtgaaag     1980
ttactgtgta aacatgaaga atttaagagc agcctgtaac aaaagttttg tggaaaagac     2040
atttgtactt caccaatatt catcaaagga cgaagattgc gtctctaaaa aaaaaaaaa      2100 aaaaaaaaaa aaaaaaaaa                                                  2120
```

<210> SEQ ID NO 30
<211> LENGTH: 567
<212> TYPE: PRT
<213> ORGANISM: Arabidopsis Thaliana

<400> SEQUENCE: 30

Met Gln Ser Val Leu Ser Leu Ser Phe Ser Gln Ala Ser Leu Pro Leu

-continued

```
  1               5              10              15
Ala Asn Arg Thr Leu Cys Ser Ser Asn Ala Pro Ser Thr Pro Arg
             20              25              30

Asn Leu Arg Phe Cys Gly Leu Arg Arg Glu Ala Phe Cys Phe Ser Pro
             35              40              45

Ser Lys Gln Leu Thr Ser Cys Arg Phe His Ile Gln Ser Arg Arg Ile
 50              55              60

Glu Val Ser Ala Ala Ser Ser Ser Ala Gly Asn Gly Ala Pro Ser
 65              70              75              80

Lys Ser Phe Asp Tyr Asp Leu Ile Ile Gly Ala Gly Val Gly Gly
             85              90              95

His Gly Ala Ala Leu His Ala Val Glu Lys Gly Leu Lys Thr Ala Ile
             100             105             110

Ile Glu Gly Asp Val Val Gly Thr Cys Val Asn Arg Gly Cys Val
             115             120             125

Pro Ser Lys Ala Leu Leu Ala Val Ser Gly Arg Met Arg Glu Leu Gln
130             135             140

Asn Glu His His Met Lys Ala Phe Gly Leu Gln Val Ser Ala Ala Gly
145             150             155             160

Tyr Asp Arg Gln Gly Val Ala Asp His Ala Ser Asn Leu Ala Thr Lys
             165             170             175

Ile Arg Asn Asn Leu Thr Asn Ser Met Lys Ala Leu Gly Val Asp Ile
             180             185             190

Leu Thr Gly Phe Gly Ala Val Leu Gly Pro Gln Lys Val Lys Tyr Gly
             195             200             205

Asp Asn Ile Ile Thr Gly Lys Asp Ile Ile Ala Thr Gly Ser Val
210             215             220

Pro Phe Val Pro Lys Gly Ile Glu Val Asp Gly Lys Thr Val Ile Thr
225             230             235             240

Ser Asp His Ala Leu Lys Leu Glu Ser Val Pro Asp Trp Ile Ala Ile
             245             250             255

Val Gly Ser Gly Tyr Ile Gly Leu Glu Phe Ser Asp Val Tyr Thr Ala
             260             265             270

Leu Gly Ser Glu Val Thr Phe Ile Glu Ala Leu Asp Gln Leu Met Pro
             275             280             285

Gly Phe Asp Pro Glu Ile Ser Lys Leu Ala Gln Arg Val Leu Ile Asn
             290             295             300

Thr Arg Lys Ile Asp Tyr His Thr Gly Val Phe Ala Ser Lys Ile Thr
305             310             315             320

Pro Ala Lys Asp Gly Lys Pro Val Leu Ile Glu Leu Ile Asp Ala Lys
             325             330             335

Thr Lys Glu Pro Lys Asp Thr Leu Glu Val Asp Ala Ala Leu Ile Ala
             340             345             350

Thr Gly Arg Ala Pro Phe Thr Asn Gly Leu Gly Leu Glu Asn Ile Asn
             355             360             365

Val Thr Thr Gln Arg Gly Phe Ile Pro Val Asp Glu Arg Met Arg Val
             370             375             380

Ile Asp Gly Asn Gly Lys Leu Val Pro His Leu Tyr Cys Ile Gly Asp
385             390             395             400

Ala Asn Gly Lys Leu Met Leu Ala His Ala Ser Ala Gln Gly Ile
             405             410             415

Ser Val Val Glu Gln Val Thr Gly Arg Asp His Val Leu Asn His Leu
             420             425             430
```

-continued

```
Ser Ile Pro Ala Ala Cys Phe Thr His Pro Glu Ile Ser Met Val Gly
        435                 440                 445
Leu Thr Glu Pro Gln Ala Arg Glu Lys Ala Glu Lys Glu Gly Phe Lys
    450                 455                 460
Val Ser Ile Ala Lys Thr Ser Phe Lys Ala Asn Thr Lys Ala Leu Ala
465                 470                 475                 480
Glu Asn Glu Gly Glu Gly Leu Ala Lys Met Ile Tyr Arg Pro Asp Asn
                485                 490                 495
Gly Glu Ile Leu Gly Val His Ile Phe Gly Leu His Ala Ala Asp Leu
            500                 505                 510
Ile His Glu Ala Ser Asn Ala Ile Ala Leu Gly Thr Arg Ile Gln Asp
        515                 520                 525
Ile Lys Leu Ala Val His Ala His Pro Thr Leu Ser Glu Val Val Asp
    530                 535                 540
Glu Leu Phe Lys Ala Ala Lys Val Asp Ser Pro Ala Ser Val Thr Ala
545                 550                 555                 560
Gln Ser Val Lys Val Thr Val
                565
```

<210> SEQ ID NO 31
<211> LENGTH: 32
<212> TYPE: DNA
<213> ORGANISM: Artificial Sequence
<220> FEATURE:
<221> NAME/KEY: Source
<222> LOCATION: (1)...(32)
<223> OTHER INFORMATION: Artificial

<400> SEQUENCE: 31
tcgaggatcc gcggccgcaa gcttcctgca gg                           32

<210> SEQ ID NO 32
<211> LENGTH: 33
<212> TYPE: DNA
<213> ORGANISM: Artificial Sequence
<220> FEATURE:
<221> NAME/KEY: Source
<223> OTHER INFORMATION: (1)...(33)
<223> OTHER INFORMATION: Artificial

<400> SEQUENCE: 32
tcgacctgca ggaagctttg cggccgcgga tcc                          33

<210> SEQ ID NO 33
<211> LENGTH: 32
<212> TYPE: DNA
<213> ORGANISM: Artificial Sequence
<220> FEATURE:
<221> NAME/KEY: Source
<222> LOCATION: (1)...(32)
<223> OTHER INFORMATION: Artificial

<400> SEQUENCE: 33
tcgacctgca ggaagcttgc ggccgcggat cc                           32

<210> SEQ ID NO 34
<211> LENGTH: 32
<212> TYPE: DNA
<213> ORGANISM: Artificial Sequence
<220> FEATURE:
<221> NAME/KEY: Source
<222> LOCATION: (1)...(32)
<223> OTHER INFORMATION: Artificial

```
<400> SEQUENCE: 34
tcgaggatcc gcggccgcaa gcttcctgca cg                                32

<210> SEQ ID NO 35
<211> LENGTH: 36
<212> TYPE: DNA
<213> ORGANISM: Artificial Sequence
<220> FEATURE:
<221> NAME/KEY: Source
<222> LOCATION: (1)...(36)
<223> OTHER INFORMATION: Artificial

<400> SEQUENCE: 35
tcgaggatcc gcggccgcaa gcttcctgca ggagct                            36

<210> SEQ ID NO 36
<211> LENGTH: 28
<212> TYPE: DNA
<213> ORGANISM: Artificial Sequence
<220> FEATURE:
<221> NAME/KEY: Source
<222> LOCATION: (1)...(28)
<223> OTHER INFORMATION: Artificial

<400> SEQUENCE: 36
cctgcaggaa gcttgcggcc gcggatcc                                     28

<210> SEQ ID NO 37
<211> LENGTH: 39
<212> TYPE: DNA
<213> ORGANISM: Artificial Sequence
<220> FEATURE:
<221> NAME/KEY: Source
<222> LOCATION: (1)...(39)
<223> OTHER INFORMATION: Artificial

<400> SEQUENCE: 37
gatcacctgc aggaagcttg cggccgcgga tccaatgca                         39

<210> SEQ ID NO 38
<211> LENGTH: 31
<212> TYPE: DNA
<213> ORGANISM: Artificial Sequence
<220> FEATURE:
<221> NAME/KEY: Source
<222> LOCATION: (1)...(31)
<223> OTHER INFORMATION: Artificial

<400> SEQUENCE: 38
ttggatccgc ggccgcaagc ttcctgcagg t                                 31
```

MATERIALS AND METHODS FOR THE ALTERATION OF ENZYME AND ACETYL COA LEVELS IN PLANTS

This application claims priority to U.S. provisional patent application Ser. No. 60/090,717, filed Jun. 26, 1998.

GOVERNMENT SUPPORT

This invention was made, in part, with funding from the National Science Foundation under Grant No. IBN-9696154 and from the Department of Energy to the Consortium for Plant Biotechnology Research via the Prime Agreement No. DE-FC05-92OR22072. Therefore, the United States of America may have certain rights in the invention.

TECHNICAL FIELD OF THE INVENTION

The present invention relates to nucleic acid and amino acid sequences of acetyl CoA synthetase (ACS), plastidic pyruvate dehydrogenase (pPDH), ATP citrate lyase (ACL), pyruvate decarboxylase (PDC) from Arabidopsis, and aldehyde dehydrogenase (ALDH) from Arabidopsis. The present invention also relates to a recombinant vector comprising (i) a nucleic acid sequence encoding an aforementioned enzyme, (ii) an antisense sequence thereto or (iii) a ribozyme therefor, a cell transformed with such a vector, antibodies to the enzymes, a plant cell, a plant tissue, a plant organ or a plant in which the level of an enzyme or acetyl CoA, or the capacity to produce acetyl CoA, has been altered, and a method of producing such a plant cell, plant tissue, plant organ or plant. In addition, the present invention relates to a recombinant vector comprising (i) an antisense sequence to a nucleic acid sequence encoding PDC, the $E1_\alpha$ subunit of pPDH, the $E1_\beta$ subunit of pPDH, the E2 subunit of pPDH, mitochondrial pyruvate dehydrogenase (mtPDH) or ALDH or (ii) a ribozyme that can cleave an RNA molecule encoding PDC, $E1_\alpha$pPDH, $E1_\beta$pPDH, E2 pPDH, mtPDH or ALDH.

BACKGROUND OF THE INVENTION

ACS and pPDH are two enzymes that are responsible for the generation of acetyl CoA in the plastids, e.g., chloroplasts, of plants. ACS generates acetyl CoA as follows:

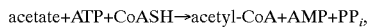

acetate+ATP+CoASH→acetyl-CoA+AMP+$PP_i$, wherein ATP represents adenine triphosphate, CoASH represents coenzyme A, acetyl-CoA represents acetyl coenzyme A, AMP represents adenine monophosphate, and $PP_i$ represents inorganic pyrophosphate, and wherein the acetate includes that which results from the conversion of acetaldehyde and $NAD^+$ to acetate and NADH, wherein the acetaldehyde, in turn, results from the breakdown of pyruvate, which releases $CO_2$. pPDH generates acetyl CoA as follows:

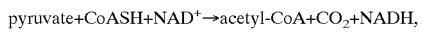

pyruvate+CoASH+$NAD^+$→acetyl-CoA+$CO_2$+NADH, wherein $NAD^+$ represents nicotinamide adenine dinucleotide and NADH represents the reduced form of $NAD^+$ and wherein the pyruvate results from glycolysis. Glycolysis involves the conversion of sugar phosphates, which have been produced from starch, photosynthesis or the importation of triose and hexose phosphates from the cytosol, to pyruvate.

Various studies of relative activity of enzymes in embryos and leaves of plants, such as spinach, castor bean, barley and Brassica have been conducted (see, Kang and Rawsthorne, Plant J 6: 795–805 (1994); Miernyk and Dennis, J. Exper. Bot. 34: 712–718 (1983); Smith et al., Plant Physiol. 98: 1233–1238 (1992); Liedvogel and Bauerle, Planta 169: 481–489 (1986); Murphy and Leech, FEBS Letter 77: 164–168 (1977); Roughan et al., Biochem. J. 158: 593–601 (1976); Roughan et al., Biochem. J. 184: 565–569 (1978); Roughan et al., Biochem. J. 184: 193–202 (1979); Springer and Heise, Planta 177: 417–421 (1989); Schulze-Siebert and Shultz, Plant Physiol. 84: 1233–1237 (1987); and Heintze et al., Plant Physiol. 93: 1121–1127 (1990)). Such studies suggest that acetate is the preferred substrate for fatty acid synthesis in chloroplasts, while pyruvate is the preferred substrate for fatty acid synthesis in plastids in embryos.

The acetyl CoA so produced is then involved in fatty acid biosynthesis, i.e., the synthesis of the basic building blocks of membrane lipids, fats and waxes. A similar reaction is effected by mtPDH in the mitochondrion.

ACS is exclusively found in the plastids of plants and is strongly regulated by light (Sauer and Heise, Z. Naturforsch 38 c: 399–404 (1983)). The amount of ACS is fairly constant between spinach, pea and amaranthus chloroplasts; there is about 20% more in corn chloroplasts. Given that the partially purified enzyme is completely DTT-dependent suggests that its activity in vivo may be regulated by the ferredoxin/thioredoxin system (Zeiher and Randall, Plant Physiol. 96: 382–389 (1991)). There is some potential for weak feedback inhibition by acetyl CoA. The enzyme also has a high pH requirement, along with a dependency on a high ATP($Mg^{2+}$-ATP)/ADP ratio (Sauer and Heise (1983), supra). The ACS reaction should be substrate saturated because $K_m$ values for acetate are between 0.02 and 0.10 mM in spinach (Sauer and Heise (1983), supra; Zeiher and Randall (991), supra; and Treede and Heise, Z. Naturforsch 40 c: 496–502 (1985)), peas (Treede and Heise (1985), supra), amaranthus (Roughan and Ohlrogge, Anal. Biochem. 216: 77–82 (1 994)) and potatoes (Huang and Stumpf, Arch Biochem. Biophys. 140: 158–173 (1970)), whereas the concentration of cellular acetate is estimated to be about 1.0 mM (Kuhn et al., Arch Biochem. Biophys. 209: 441–450 (1981)).

The pPDH appears to have the same general structure as mtPDH, being composed of a pyruvate dehydrogenase component ($E1_\alpha$ and $E1_\beta$), a transacetylase component (E2), and dehydrolipoamide dehydrogenase (E3) subunits. The molecular weight of pPDH and its cofactor requirements are also similar to mtPDH, although affinities for $NAD^+$ and TPP vary somewhat (Camp and Randall, Plant Physiol. 77: 571–577 (1985); Miernyk et al. (1983), supra; and Conner et al., Planta 200: 195–202 (1996)). pPDH, which is less sensitive to acetyl CoA than mtPDH, has an optimal pH of about 8.0 and requires about 10 mM $Mg^{2+}$ for maximal activity. While the activity of mtPDH is controlled by a sophisticated kinase/phosphatase system, which phosphorylates and thereby inactivates the $E1_\alpha$ subunit, pPDH is not subject to such regulation. However, pPDH is strongly regulated by the NADH/$NAD^+$ ratio and is moderately regulated by light. Regulation by ATP, NADPH, fatty acyl CoAs and glycolytic intermediates is minor (Camp et al., Biochim. Biophys. Acta 933: 269–275 (1988); and Qi et al., J. Exp. Bot. 47: 1889–1896 (1996)).

PDH activity varies from one tissue to the next with mtPDH activity varying 15-fold and pPDH activity varying 6-fold (Lernmark and Gardestrom, Plant Physiol. 106: 1633–1638 (1994)). The ratio of pPDH/mtPDH also varies between plants, with 6.5 times more activity in the chloroplasts than in the mitochondria of wheat leaves to 6.7 times more activity in the mitochondria than in the chloroplasts of peas. Although chloroplasts have proportionally less PDH activity than mitochondria in pea as compared to wheat, the chloroplasts have nearly as much PDH as mitochondria in absolute terms.

ACL is an enzyme that is responsible for the generation of acetyl CoA. ACL generates acetyl CoA as follows:

$$\text{citrate} + \text{ATP} + \text{CoASH} \rightarrow \text{acetyl-CoA} + \text{oxaloacetate} + \text{ADP} + P_i,$$

wherein ADP represents adenosine diphosphate and $P_i$ represents orthophosphate and wherein the citrate is that which is generated in the TCA cycle in the mitochondrion.

The activity of ACL has been found to correlate with lipid accumulation in developing seeds of *Brassica napus* L. (Ratledge et al., *Lipids* 32(1): 7–12 (1997)) and in the supernatant of a developing soybean (*Glycine max* L. Merr., var. Harosoy 63) cotyledon homogenate (Nelson et al., *Plant Physiol.* 55: 69–72 (1975)). ACL also has been found in crude extracts from the endosperm tissue of germinating castor bean (*Ricinus communis* cv. Hale) and has been found to be maximally active in 4–5-day old seedlings (Fritsch et al., *Plant Physiol.* 63: 687–691 (1979)).

PDC is a cytosolic enzyme that is responsible for the generation of acetaldehyde from pyruvate. PDC generates acetaldehyde from pyruvate as follows:

$$\text{pyruvate} \rightarrow \text{acetaldehyde} + CO_2.$$

The acetaldehyde so produced can be acted upon by ALDH.

ALDH is responsible for the generation of acetate from acetaldehyde. ALDH generates acetate from acetaldehyde as follows:

$$\text{acetaldehyde} + NAD^+ + H_2O \rightarrow \text{acetate} + NADH^+ + H^+.$$

The acetate so produced can then enter the plastids, where it can be converted to acetyl CoA through the action of ACS.

ACH is an enzyme that is known to exist in yeast and is believed to exist in the mitochondria of plants. ACH is believed to generate acetate from acetyl CoA pools present in the mitochondria. The acetate so produced is then believed to be released from the mitochondrion into the cytosol. The cytosolic acetate can then enter the plastids, wherein it can be converted to acetyl CoA through the action of ACS.

Acetyl CoA is the common precursor of a large number of phytochemicals, which have widely varied biological functions and which represent renewable, energy-rich products of agriculture (e.g., fats, oils, waxes, isoprenoids and bioplastics (e.g., polyhydroxybutyrate) or which affect agricultural production (e.g., flavonoids, stilbenoids, isoprenoids and malonyl derivatives) (Goodwin and Mercer, *Introduction to Plant Biochemistry*, $2_{nd}$ ed., Pergamon Press, New York (1988)). These phytochemicals are synthesized either by the carboxylation or sequential condensation of acetyl CoA.

Carboxylation of acetyl CoA (via the intermediate malonyl CoA) leads to the biosynthesis of fatty acids (e.g., membranes, oils, cuticle, suberin and cutin), flavonoids (e.g., pigments, phytoalexins and plant protection), stilbenoids (e.g., plant protection and pharmaceuticals), acridones, malonic acid, and a variety of malonyl derivatives (aminocyclopropane carboxylic acids, D-amino acids, flavonoids and pesticides). Fatty acids are the building blocks of all cellular membranes. In addition, fatty acids are utilized in developmentally regulated processes in the biogenesis of seed oils, cuticle, cutin and suberin. Most seed oils are triacylglycerols. Flavonoids are a group of water-soluble phenolic compounds that have a wide range of biological activities as pigments and they accumulate in responses of plants to biotic and abiotic stresses (e.g., drought, fungal and bacterial pathogens, and salt stress). Stilbenoids are thought to play a role in plant defense mechanisms. The acridones are a class of alkaloids that have a wide spectrum of antimicrobial, antimolluscosidal and antiviral activities. Numerous malonyl derivatives exist in plants, including those of D-amino acids, flavonoids and xenobiotics, such as pesticides. The malonation of aminocyclopropanecarboxylic acid, which is the precursor of ethylene, may influence the generation of the hormone ethylene.

The condensation of acetyl CoA (via the intermediates acetoacetyl CoA and HMG CoA) leads to the biosynthesis of isoprenoids. Examples of isoprenoids include sterols, phytoalexins, abscisic acid, gibberellins, phytoene, β-carotene, phytol, natural rubber, plant protection and pharmaceuticals. Isoprenoids are also significant constituents of many essential oils and fragrances.

In addition, and of great excitement to the biotechnology industry, acetoacetyl CoA is the precursor for the production of a potentially new agricultural product from transgenic plants, namely polyhydroxybutyrate (PHB, a type of bioplastic). Research to date indicates that the production of transgenic bioplastics may be limited by the supply of acetyl CoA (Nawrath et al., *PNAS USA* 91: 12760–12764 (1994)).

The pathways that utilize acetyl CoA as a precursor are spatially and temporally compartmentalized. Fatty acids and sterols are synthesized by all cells for membrane biogenesis. The accumulation of most of the other acetyl CoA-derived phytochemicals is highly cell-specific and occurs in specific subcellular compartments at particular stages of development or in response to particular environmental signals. For example, acetyl CoA is required in plastids for de novo fatty acid synthesis, which produces 18-carbon fatty acids. The elongation of 18-carbon fatty acids to fatty acids of 20 carbons and longer requires a cytosolic acetyl CoA pool. Acetyl CoA is also required in the cytosol for the biosynthesis of isoprenoids, flavonoids, and several, if not all, of the malonated derivatives: In addition, fatty acid synthesis in the plastid should be maximal during triacylglycerol deposition in oil seed as well as during times of maximum membrane formation, such as during the conversion of proplastids to chloroplasts.

Therefore, in view of the above, there remains a need for materials and methods to alter the level of enzymes involved in acetyl CoA production and, consequently, acetyl CoA levels in plants. Accordingly, it is an object of the present invention to provide such materials and methods. These and other objects and advantages of the present invention, as well as additional inventive features, will become apparent to one of ordinary skill in the art from the following description.

BRIEF SUMMARY OF THE INVENTION

In one embodiment, the present invention provides isolated or purified nucleic acid molecules. One isolated or purified nucleic acid molecule encodes a plant plastidic ACS, such as that which is isolated from Arabidopsis, and a continuous fragment thereof comprising at least about 20 nucleotides. Preferably, the ACS-encoding nucleic acid molecule is (i) DNA and comprises SEQ ID NO: 1 or a sequence that encodes SEQ ID NO: 2, (ii) RNA and comprises a sequence encoded by SEQ ID NO: 1 or a sequence that encodes SEQ ID NO: 2, or (iii) a nucleic acid molecule that hybridizes to either one of the foregoing under stringent conditions. Also provided is an isolated or purified nucleic acid molecule encoding a modified ACS and a continuous fragment thereof comprising at least about 20 nucleotides.

Also in this regard, the present invention further provides an isolated or purified nucleic acid molecule encoding the E3 subunit of a plant pPDH (E3 pPDH), such as that which is isolated from Arabidopsis, and a continuous fragment thereof comprising at least about 20 nucleotides. Preferably, the E3 pPDH-encoding nucleic acid molecule is (i) DNA and comprises SEQ ID NO: 27 (E3-1 pPDH) or SEQ ID NO: 29 (E3-2 pPDH) or a sequence that encodes SEQ ID NO: 28 (E3-1 pPDH) or SEQ ID NO: 30 (E3-2 pPDH), (ii) RNA and comprises a sequence encoded by SEQ ID NO: 27 or SEQ ID NO: 29 or a sequence that encodes SEQ ID NO: 28 or SEQ ID NO: 30, or (iii) a nucleic acid molecule that hybridizes to either one of the foregoing under stringent conditions. Also provided is an isolated or purified nucleic acid molecule encoding a modified E3 subunit of pPDH and a continuous fragment thereof comprising at least about 20 nucleotides.

Another isolated or purified nucleic acid molecule encodes the A subunit of a plant ACL (ACL-A), such as that which is isolated from Arabidopsis, and a continuous fragment thereof comprising at least about 20 nucleotides. Preferably, the ACL-A-encoding nucleic acid molecule is (i) DNA and comprises SEQ ID NO: 7 or a sequence that encodes SEQ ID NO: 8, (ii) RNA and comprises a sequence encoded by SEQ ID NO: 7 or a sequence that encodes SEQ ID NO: 8 or (iii) a nucleic acid molecule that hybridizes to either one of the foregoing under stringent conditions.

Also provided is an isolated or purified nucleic acid molecule encoding a modified A subunit of ACL and a continuous fragment thereof comprising at least about 20 nucleotides.

In this regard, the present invention further provides an isolated or purified nucleic acid molecule encoding the B subunit of a plant ACL (ACL-B), such as that which is isolated from Arabidopsis, and a continuous fragment thereof comprising at least about 20 nucleotides. Preferably, the ACL-B-encoding nucleic acid molecule is (i) DNA and comprises SEQ ID NO: 9 (ACL-B1) or SEQ ID NO: 11 (ACL-B2) or a sequence that encodes SEQ ID NO: 10 (ACL-B1) or SEQ ID NO: 12 (ACL-B2), (ii) RNA and comprises a sequence encoded by SEQ ID NO: 9 or SEQ ID NO: 11 or a sequence that encodes SEQ ID NO: 10 or SEQ ID NO: 12, or (iii) a nucleic acid molecule that hybridizes to either one of the foregoing under stringent conditions. Also provided is an isolated or purified nucleic acid molecule encoding a modified B subunit of ACL and a continuous fragment thereof comprising at least about 20 nucleotides.

An isolated and purified nucleic acid molecule comprising the nucleotide sequence of SEQ ID NO: 15 or SEQ ID NO: 17 or encoding the amino acid sequence of SEQ ID NO: 16 or SEQ ID NO: 18 is also provided by the present invention.

Likewise, an isolated and purified nucleic acid molecule comprising the nucleotide sequence of SEQ ID NO: 21 or encoding the amino acid sequence of SEQ ID NO: 22 or a continuous fragment of either of the foregoing comprising at least about 20 nucleotides or a nucleic acid molecule that hybridizes to any of the foregoing under stringent conditions.

Similarly, an isolated and purified nucleic acid molecule comprising the nucleotide sequence of SEQ ID NO: 25 or encoding the amino acid sequence of SEQ ID NO: 26 or a continuous fragment of either of the foregoing comprising at least about 20 nucleotides or a nucleic acid molecule that hybridizes to any of the foregoing under stringent conditions.

In another embodiment, the present invention also provides a vector comprising a nucleic acid molecule as described above, a host cell comprising such a vector, and a polypeptide produced by such a host cell. Also provided are vectors comprising or encoding an antisense sequence that hybridizes to or a ribozyme that cleaves an RNA molecule encoding plastidic ACS, the $E1_\alpha$ subunit of pPDH, the $E1_\beta$ subunit of pPDH, the E2 subunit of pPDH, the E3 subunit of pPDH, the A subunit of ACL, the B subunit of ACL, PDC, ACH, mtPDH or ALDH, and a host cell comprising such a vector. In addition, antisense molecules, ribozymes and antibodies are provided.

In yet another embodiment, the present invention provides a method of altering the level of an enzyme in a plant cell, a plant tissue, a plant organ or a plant. The method comprises contacting the plant cell, plant tissue, plant organ or plant with a vector comprising a nucleic acid molecule selected from the group consisting of (i) a gene encoding an enzyme or, if the enzyme is comprised of subunits, a subunit of an enzyme selected from the group consisting of plastidic ACS, pPDH, ACL, pyruvate decarboxylase, acetyl CoA hydrolase, mitochondrial pyruvate dehydrogenase and aldehyde dehydrogenase, (ii) a nucleic acid molecule comprising or encoding an antisense molecule to an RNA molecule transcribed from a gene of (i), and (iii) a nucleic acid molecule comprising or encoding a ribozyme to an RNA molecule transcribed from a gene of (i). The vector comprising a nucleic acid molecule of (i) increases or decreases the level of an enzyme in the plant cell, plant tissue, plant organ or plant, whereas the vector comprising or encoding a nucleic acid molecule of (ii) or (iii) decreases the level of an enzyme in the plant cell, plant tissue, plant organ or plant. Preferably, the alteration of the enzyme results in an alteration of the level of acetyl CoA in the plant cell, plant tissue, plant organ or plant. Accordingly, the present invention further provides a plant cell, a plant tissue, a plant organ and a plant in which the level of acetyl CoA has been altered in accordance with the method.

BRIEF DESCRIPTION OF THE DRAWINGS

FIG. 1 is a description of cDNA [SEQ ID NO: 1] and amino acid [SEQ ID NO: 2] sequences for ACS.

FIG. 2 is a description of cDNA [SEQ ID NO: 3] and amino acid [SEQ ID NO: 4] sequences for the $E1_\alpha$ subunit of pPDH.

FIG. 3 is a description of cDNA [SEQ ID NO: 5] and amino acid [SEQ ID NO: 6] sequences for the $E1_\beta$-1 subunit of pPDH.

FIG. 4 is a description of cDNA [SEQ ID NO: 7] and amino acid [SEQ ID NO: 8] sequences for the A subunit of ACL.

FIG. 5 is a description of cDNA [SEQ ID NO: 9] and amino acid [SEQ ID NO: 10] sequences for the B-1 subunit of ACL.

FIG. 6 is a description of cDNA [SEQ ID NO: 11 ] and amino acid [SEQ ID NO: 12] sequences for the B-2 subunit of ACL.

FIG. 7 is a description of cDNA [SEQ ID NO: 13] and amino acid [SEQ ID NO: 14] sequences for the $E1_\beta$-2 subunit of pPDH.

FIG. 8A is a description of the cDNA sequence [SEQ ID NO: 15] of PDC-1 from Arabidopsis.

FIG. 8B is a description of the amino acid sequence [SEQ ID NO: 16] of PDC-1 from Arabidopsis.

FIG. 9A is a description of the cDNA sequence [SEQ ID NO: 17] of PDC-2 from Arabidopsis.

FIG. 9B is a description of the amino acid sequence [SEQ ID NO: 18] of PDC-2 from Arabidopsis.

FIG. 10A is a description of the cDNA sequence [SEQ ID NO: 19] of ALDH-1 from Arabidopsis.

FIG. 10B is a description of the amino acid sequence [SEQ ID NO: 20] of ALDH-1 from Arabidopsis.

FIG. 11A is a description of the cDNA sequence [SEQ ID NO: 21] of ALDH-2 from Arabidopsis.

FIG. 11B is a description of the amino acid sequence [SEQ ID NO: 22] of ALDH-2 from Arabidopsis.

FIG. 12A is a description of the cDNA sequence [SEQ ID NO: 23] of ALDH-3 from Arabidopsis.

FIG. 12B is a description of the amino acid sequence [SEQ ID NO: 24] of ALDH-3 from Arabidopsis.

FIG. 13 is a description of cDNA [SEQ ID NO: 25] and amino acid [SEQ ID NO: 26] sequences for ALDH-4 from Arabidopsis.

FIG. 14 is a description of cDNA [SEQ ID NO: 27] and amino acid, [SEQ ID NO: 28] sequences for the E3-1 subunit of pPDH from Arabidopsis.

FIG. 15 is a description of cDNA [SEQ ID NO: 29] and amino acid [SEQ ID NO: 30] sequences for the E3-2 subunit of pPDH from Arabidopsis.

DETAILED DESCRIPTION OF THE INVENTION

In one embodiment, the present invention provides isolated or purified nucleic acid molecules. By "isolated" is meant the removal of a nucleic acid from its natural environment. By "purified" is meant that a given nucleic acid, whether one that has been removed from nature (including genomic DNA and MRNA) or synthesized (including cDNA) and/or amplified under laboratory conditions, has been increased in purity, wherein "purity" is a relative term, not "absolute purity." "Nucleic acid molecules" is intended to encompass a polymer of DNA or RNA, i.e., a polynucleotide, which can be single-stranded or double-stranded and which can contain non-natural or altered nucleotides.

One isolated or purified nucleic acid molecule encodes a plant ACS, such as that which is isolated from Arabidopsis, and a continuous fragment thereof comprising at least about 20 nucleotides. Preferably, the ACS-encoding nucleic acid molecule is (i) DNA and comprises SEQ ID NO: 1 or a sequence that encodes SEQ ID NO: 2, (ii) RNA and comprises a sequence encoded by SEQ ID NO: 1 or a sequence that encodes SEQ ID NO: 2, or (iii) a nucleic acid molecule that hybridizes to either of the foregoing under stringent conditions. Also provided is an isolated or purified nucleic acid molecule encoding a modified ACS, which comprises one or more insertions, deletions and/or substitutions, and a continuous fragment thereof comprising at least about 20 nucleotides. Desirably, the modified ACS does not differ functionally from the corresponding unmodified ACS, such as that comprising SEQ ID NO: 2. Preferably, the modified ACS converts acetate to acetyl-CoA at least about 50%, more preferably at least about 75%, and most preferably at least about 90% as well as the corresponding unmodified ACS, such as that comprising SEQ ID NO: 2, as determined by in vitro assay using labeled acetate. Use of the word "labeled" herein is intended to mean any means of detection, such as a radioactive isotope.

The cDNA encoding ACS from Arabidopsis encodes a 76.7 kDa protein. The ACS of Arabidopsis is similar to that of E. coli and yeast, which contains two isoforms. Southern blot analysis of Arabidopsis DNA indicates that ACS is a single-copy gene. The ACS sequence from Arabidopsis is 56% similar and 48% identical to the ACS sequence of yeast and 66% similar and 58% identical to the ACS sequence of Arabidopsis. The sequence for ACS is available from GenBank as accession no. AF036618.

Another isolated or purified nucleic acid molecule provided by the present invention encodes the $E1_\alpha$ subunit of a plant pPDH ($E1_\alpha$pPDH), such as that which is isolated from Arabidopsis, and a continuous fragment thereof comprising at least about 20 nucleotides (see, also, Johnston et al., BBA 1321: 200–206 (1997)). Preferably, the $E1_\alpha$pPDH-encoding nucleic acid molecule is (i) DNA and comprises SEQ ID NO: 3 or a sequence that encodes SEQ ID NO: 4, (ii) RNA and comprises a sequence encoded by SEQ ID NO: 3 or a sequence that encodes SEQ ID NO: 4, or (iii) a nucleic acid molecule that hybridizes to either one of the foregoing under stringent conditions. Also provided is an isolated or purified nucleic acid molecule encoding a modified $E1_\alpha$pPDH subunit, which comprises one or more insertions, deletions and/or substitutions, and a continuous fragment thereof comprising at least about 20 nucleotides. Desirably, the modified $E1_\alpha$pPDH subunit does not differ functionally from the corresponding unmodified $E1_\alpha$pDPH, such as that comprising SEQ ID NO: 4. Preferably, the modified $E1_\alpha$ subunit of a plant pPDH, together with the remaining unmodified subunits of pPDH, does not differ functionally from a corresponding unmodified pPDH. Preferably, the modified pPDH converts pyruvate to acetyl-CoA at least about 50%, more preferably at least about 75%, most preferably at least about 90% as well as the corresponding unmodified pPDH, such as that comprising the $E1_\alpha$ subunit comprising SEQ ID NO: 4, as determined by in vitro assay in the presence of labeled pyruvate.

The cDNA encoding the $E1_\alpha$ subunit of pPDH from Arabidopsis encodes a 47 kDa protein. The $E1_\alpha$ subunit is similar to that of Porphyra purpurea chloroplasts. Southern blot analysis of Arabidopsis DNA indicates that the Ela subunit is a single copy gene. The $E1_\alpha$ subunit sequence from Arabidopsis is 61% identical to the $E1_\alpha$ subunit of Porphyra purpurea $E1_\alpha$ subunit sequence.

In this regard, the present invention further provides an isolated or purified nucleic acid molecule encoding the $E1_\beta$ subunit of a plant pPDH ($E1_\alpha$pPDH), such as that which is isolated from Arabidopsis, and a continuous fragment thereof comprising at least about 20 nucleotides (see also Johnston et al. (1997), supra). Preferably, the $E1_\beta$pPDH-encoding nucleic acid molecule is (i) DNA and comprises SEQ ID NO: 5 ($E1_\beta$-1pPDH) or SEQ ID NO: 13 ($E1_\beta$-2 pPDH) or a sequence that encodes SEQ ID NO: 6 or SEQ ID NO: 14, (ii) RNA and comprises a sequence encoded by SEQ ID NO: 5 or SEQ ID NO: 13 or a sequence that encodes SEQ ID NO: 6 or SEQ ID NO: 14, or (iii) a nucleic acid molecule that hybridizes to either one of the foregoing under stringent conditions. Also provided is an isolated or purified nucleic acid molecule encoding a modified $E1_\beta$ subunit of pPDH, which comprises one or more insertions, deletions and/or substitutions, and a continuous fragment thereof comprising at least about 20 nucleotides. Desirably, the modified $E1_\beta$pPDH subunit does not differ functionally from the corresponding unmodified $E1_\beta$pPDH subunit, such as that comprising SEQ ID NO: 6 or SEQ ID NO: 14. Preferably, the modified $E1_\beta$ subunit of a plant pPDH, together with the remaining unmodified subunits of pPDH, does not differ functionally from a corresponding unmodified pPDH. Preferably, the modified pPDH converts pyruvate to acetyl-CoA at least about 50%, more preferably at least about 75%, most preferably at least about 90% as well as the corresponding unmodified pPDH, such as that comprising the $E1_\beta$ subunit comprising SEQ ID NO: 6 or SEQ ID NO: 14, as determined by in vitro assay using labeled pyruvate.

The $E1_\beta$ subunit of pPDH is encoded by at least two genes in Arabidopsis designated $E1_\beta$-1 and $E1_\beta$-2, which are about 95% identical at the amino acid level. The cDNA encoding the $E1_\beta$-1 subunit of pPDH from Arabidopsis encodes a 44 kDa protein. The $E1_\beta$-1 subunit of pPDH of Arabidopsis is 78% similar and 70% identical to the pPDH of *Porphyra purpurea* and 52% similar and 41% identical to the $E1_\beta$ subunit of mtPDH.

Also in this regard, the present invention further provides an isolated or purified nucleic acid molecule encoding the E3 subunit of a plant pPDH (E3 PPDH), such as that which is isolated from Arabidopsis, and a continuous fragment thereof comprising at least about 20 nucleotides. Preferably, the E3 pPDH-encoding nucleic acid molecule is (i) DNA and comprises SEQ ID NO: 27 (E3-1 pPDH) or SEQ ID NO: 29 (E3-2 PPDH) or a sequence that encodes SEQ ID NO: 28 (E3-1 pPDH) or SEQ ID NO: 30 (E3-2 pPDH), (ii) RNA and comprises a sequence encoded by SEQ ID NO: 27 or SEQ ID NO: 29 or a sequence that encodes SEQ ID NO: 28 or SEQ ID NO: 30, or (iii) a nucleic acid molecule that hybridizes to either one of the foregoing under stringent conditions. Also provided is an isolated or purified nucleic acid molecule encoding a modified E3 subunit of pPDH, which comprises one or more insertions, deletions and/or substitutions, and a continuous fragment thereof comprising at least about 20 nucleotides. Desirably, the modified E3 pPDH subunit does not differ functionally from the corresponding unmodified E3 pPDH subunit, such as that comprising SEQ ID NO: 28 or SEQ ID NO: 30. Preferably, the modified E3 subunit of a plant pPDH, together with the remaining unmodified subunits, does not differ functionally from a corresponding unmodified pPDH. Preferably, the modified pPDH converts pyruvate to acetyl-CoA at least about 50%, more preferably at least about 75%, most preferably at least about 90% as well as the corresponding unmodified pPDH, such as that comprising the E3 subunit comprising SEQ ID NO: 28 or SEQ ID NO: 30, as determined by in vitro assay using labeled pyruvate.

Yet another isolated or purified nucleic acid molecule encodes the A subunit of a plant ACL (ACL-A), such as that which is isolated from Arabidopsis, and a continuous fragment thereof comprising at least about 20 nucleotides. Preferably, the ACL-A-encoding nucleic acid molecule is (i) DNA and comprises SEQ ID NO: 7 or a sequence that encodes SEQ ID NO: 8, (ii) RNA and comprises a sequence encoded by SEQ ID NO: 7 or a sequence that encodes SEQ ID NO: 8, or (iii). a nucleic acid molecule that hybridizes to either one of the foregoing under stringent conditions. Also provided is an isolated or purified nucleic acid molecule encoding a modified A subunit of a plant ACL, which comprises one or more insertions, deletions and/or substitutions, and a continuous fragment thereof comprising at least about 20 nucleotides. Desirably, the modified ACL-A subunit does not differ functionally from the corresponding unmodified ACL-A subunit, such as that comprising SEQ ID NO: 8. Preferably, the modified ACL converts citrate to acetyl-CoA at least about 50%, more preferably at least about 75%, most preferably at least about 90% as well as the corresponding unmodified ACL, such as that comprising the A subunit comprising SEQ ID NO: 8, as determined by in vitro assay using labeled citrate.

In this regard, the present invention further provides an isolated or purified nucleic acid molecule encoding the B subunit of a plant ACL (ACL-B), such as that which is isolated from Arabidopsis, and a continuous fragment thereof comprising at least about 20 nucleotides. Preferably, the ACL-B-encoding nucleic acid molecule is (i) DNA and comprises SEQ ID NO: 9 (ACL-B1) or SEQ ID NO: 11 (ACL-B2) or a sequence that encodes SEQ ID NO: 10 or SEQ ID NO: 12, (ii) RNA and comprises a sequence encoded by SEQ ID NO: 9 or SEQ ID NO: 11 or a sequence that encodes SEQ ID NO: 10 or SEQ ID NO: 12, or (iii) a nucleic acid molecule that hybridizes to either one of the foregoing under stringent conditions. Also provided is an isolated or purified nucleic acid molecule encoding a modified B subunit of a plant ACL, which comprises one or more insertions, deletions and/or substitutions, and a continuous fragment thereof comprising at least about 20 nucleotides. Desirably, the modified ACL-B subunit does not differ functionally from the corresponding unmodified ACL-B subunit, such as that comprising SEQ ID NO: 10 or SEQ ID NO: 12. Preferably, the modified ACL converts citrate to acetyl-CoA at least about 50%, more preferably at least about 75%, most preferably at least about 90% as well as the corresponding unmodified ACL, such as that comprising the B subunit comprising SEQ ID NO: 10 or SEQ ID NO: 12, as determined by in vitro assay using labeled citrate.

ACL is encoded by a small gene family in Arabidopsis. The cDNA encoding ACL-A from Arabidopsis encodes a 45 kDa protein, whereas the cDNA encoding ACL-B from Arabidopsis encodes a 70 kDa protein. ACL-A is encoded by at least two genes in Arabidopsis which are designated ACL-A1 and ACL-A2. ACL-B is encoded by at least two genes in Arabidopsis which are designated ACL-B 1 and ACL-B2. The ACL of Arabidopsis is 50% similar to that of the human and the rat.

An isolated and purified nucleic acid molecule comprising the nucleotide sequence of SEQ ID NO: 15 or SEQ ID NO: 17 or encoding the amino acid sequence of SEQ ID NO: 16 or SEQ ID NO: 18 is also provided by the present invention.

Likewise, an isolated and purified nucleic acid molecule comprising the nucleotide sequence of SEQ ID NO: 21 or encoding the amino acid sequence of SEQ ID NO: 22 or a continuous fragment of either of the foregoing comprising at least about 20 nucleotides or a nucleic acid molecule that hybridizes to any of the foregoing under stringent conditions.

Yet another isolated or purified nucleic acid molecule provided by the present invention is that which encodes a plant ACH. Such a nucleic acid molecule, including a continuous fragment thereof of at least about 20 nucleotides in length, can be isolated from a plant in accordance with Example 9.

With respect to the above, one of ordinary skill in the art knows how to generate insertions, deletions and/or substitutions in a given nucleic acid molecule. Also with respect to the above, "does not differ functionally from" is intended to mean that the modified enzyme has enzymatic activity characteristic of the unmodified enzyme. In other words, it acts upon the same substrate and generates the same product. The modified enzyme, however, can be more or less active than the unmodified enzyme as desired in accordance with the present invention.

Nucleic-acid molecules encoding ACS, pPDH and ACL can be isolated from any plant source. Suitable plant sources include, but are not limited to, Arabidopsis, soybean, alfalfa, corn, wheat, sorghum, barley, rice, oats, rye, soybean, rapeseed, canola, cotton, safflower, peanut, palm, sorghum, sunflower, beet, and various vegetable and fruit crops, such as cucumber, tomato, peppers, and the like.

With respect to the above isolated or purified nucleic acid molecules, it is preferred that the one or more substitution(s) do(es) not result in a change in an amino acid of the enzyme. Alternatively, and also preferred, is that the one or more substitution(s) result(s) in the substitution of an amino acid with another amino acid of approximately equivalent size, shape and charge.

Also with respect to the above isolated or purified nucleic acid molecules, a "continuous fragment of at least about 20 nucleotides of the isolated or purified nucleic acid molecule," a given nucleic acid molecule is a continuous fragment that, for example, encodes an amino acid molecule that can carry out the same function as the corresponding complete amino acid molecule. For example, a fragment of an isolated or purified nucleic acid molecule encoding a plant ACS can be a continuous fragment of the ACS-encoding nucleic acid molecule that encodes an amino acid molecule that can convert acetate to acetyl-CoA in the presence of ATP and CoASH, but not necessarily as well as the corresponding complete amino acid molecule.

The above isolated or purified nucleic acid molecules also can be characterized in terms of "percentage of sequence identity." In this regard, a given nucleic acid molecule as described above can be compared to a nucleic acid molecule encoding a corresponding gene (i.e., the reference sequence) by optimally aligning the nucleic acid sequences over a comparison window, wherein the portion of the polynucleotide sequence in the comparison window may comprise additions or deletions (i.e., gaps) as compared to the reference sequence, which does not comprise additions or deletions, for optimal alignment of the two sequences. The percentage of sequence identity is calculated by determining the number of positions at which the identical nucleic acid base occurs in both sequences, i.e., the number of matched positions, dividing the number of matched positions by the total number of positions in the window of comparison, and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information, Bethesda, Md.), or by inspection. Sequences are typically compared using BESTFIT or BlastN with default parameters.

"Substantial sequence identity" means that at least 75%, preferably at least 80%, more preferably at least 90%, and most preferably at least 95% of the sequence of a given nucleic acid molecule is identical to a given reference sequence. Typically, two polypeptides are considered to be substantially identical if at least 40%, preferably at least 60%, more preferably at least 90%, and most preferably at least 95% of the amino acids of which the polypeptides are comprised are identical to or represent conservative substitutions of the amino acids of a given reference sequence.

Another indication that polynucleotide sequences are substantially identical is if two molecules selectively hybridize to each other under stringent conditions. The phrase "selectively hybridizing to" refers to the selective binding of a single-stranded nucleic acid probe to a single-stranded target DNA or RNA sequence of complementary sequence when the target sequence is present in a preparation of heterogeneous DNA and/or RNA. Stringent conditions are sequence-dependent and will be different in different circumstances. Generally, stringent conditions are selected to be about 20° C. lower than the thermal melting point (Tm) for the specific sequence at a defined ionic strength and pH. The Tm is the temperature (under defined ionic strength and pH) at which 50% of the target sequence hybridizes to a perfectly matched probe.

In view of the above, "stringent conditions" preferably allow for from about 25% to about 5% mismatch, more preferably from about 15% to about 5% mismatch, and most preferably from about 10% to about 5% mismatch. "At least moderately stringent conditions" preferably allow for from about 40% to about 15% mismatch, more preferably from about 30% to about 15% mismatch, and most preferably from about 20% to about 15% mismatch. "Low stringency conditions" preferably allow for from about 60% to about 35% mismatch, more preferably from about 50% to about 35% mismatch, and most preferably from about 40% to about 35% mismatch. With respect to the preceding ranges of mismatch, 1% mismatch corresponds to one degree decrease in the melting temperature.

One of ordinary skill in the art will appreciate, however, that two polynucleotide sequences can be substantially different at the nucleic acid level, yet encode substantially similar, if not identical, amino acid sequences, due to the degeneracy of the genetic code. The present invention is intended to encompass such polynucleotide sequences.

The above-described nucleic acid molecules, as well as the additional nucleic acid molecules described below with respect to the present inventive method, can be used, in whole or in part (i.e., as fragments), to identify and isolate corresponding genes from other plants as well as nonplants (e.g., yeast and bacterium) for use in the context of the present inventive method using conventional means as known in the art. For example, such molecules or fragments thereof can be used in chromosome walking, genomic subtraction, which requires the availability of strains having deletions of the target gene (Strauss and Ausubel, PNAS USA 87: 1889–1893 (1990); and Sun et al., *Plant Cell* 4: 119–128 (1992)), transposon (Chuck et al., *Plant Cell* 5: 371–378 (1993); Dean et al., *Plant J.* 2: 69–81 (1992); Grevelding et al., PNAS USA 899: 6085–6089 (1992); Swinburne et al., *Plant Cell* 4: 583–595 (1992); Fedoroff and Smith, *Plant J.* 3: 273–289 (1993); and Tsay et al., *Science* 260: 342–344 (1993)) and T-DNA tagging (Feldmann, *Plant J.* 1: 71–82 (1991); Feldmann et al., *Science* 243: 1351–1354 (1989); Herman et al., *Plant Cell* 11: 1051–1055 (1989); Konz et al., *EMBO J.* 9: 1337–1346 (1989); and Kieber et al., *Cell* 72: 427–441 (1993)), and heterologous probe selection techniques in accordance with methods well-known in the art. Although T-DNA tagging, chromosome walking or heterologous probe selection can identify a DNA fragment that putatively contains the gene of interest, the DNA fragment must be confirmed by genetic complementation or some other means.

In another embodiment, the present invention also provides a vector comprising a nucleic acid molecule as described above. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology,* Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, 2 mµ plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. A preferred cloning vector is selected from the group consisting of the pUC series the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121 and pBIN19 (Clonetech, Palo Alto, Calif.). Examples of animal expression vectors include pEUK-C 1, pMAM and pMAM-neo (Clonetech).

A plant expression vector can comprise a native or nonnative promoter operably linked to a nucleic acid molecule encoding ACS, pPDH or ACL as described above. The selection of promoters, e.g., strong, weak, inducible, tissue-specific and developmental-specific, is within the skill in the art. Similarly, the combining of a nucleic acid molecule as described above with a promoter is also within the skill in the art.

The expression vector optionally further comprises a transit peptide sequence between the promoter and coding sequence. For those genes that are normally expressed in the mitochondrion or plastid, it is preferred that the expression vector comprise a mitochondrial or plastidic transit peptide, respectively. Numerous plant gene products are known to contain transit peptide sequences. For example, the small subunit of ribulose bisphosphate carboxylase, ferredoxin, chlorophyll a/b binding protein, and the like, comprise transit peptide sequences. Such transit peptide sequences can be isolated/synthesized and used in expression vectors in accordance with the present invention. Regardless of the source of the DNA fragment coding for the transit peptide, it should include a translation initiation codon and an amino acid sequence recognized by and functional in the organelle of the host plant cell or plant.

The present invention not only provides a vector comprising a nucleic acid molecule as described above but also provides a vector comprising or encoding an antisense sequence that hybridizes to or a ribozyme that cleaves an RNA molecule encoding a plant plastidic acetyl CoA synthetase, the $E1_\alpha$ subunit of a plant plastidic pyruvate dehydrogenase, the $E1_\alpha$ subunit of a plant plastidic dehydrogenase, the E2 subunit of a plant plastidic pyruvate dehydrogenase, the E3 subunit of a plant plastidic pyruvate dehydrogenase, the A subunit of a plant ATP-citrate lyase, the B subunit of a plant ATP-citrate lyase, a plant pyruvate decarboxylase, a plant acetyl CoA hydrolase, a plant mitochondrial pyruvate dehydrogenase, and a plant aldehyde dehydrogenase. The present invention also provides the antisense molecules, which preferably are at least about 20 nucleotides in length, and the ribozymes, which preferably comprise at least about 20 continuous nucleotides complementary to the target sequence on each side of the active site of the ribozyme.

In view of the above, the present invention provides a host cell comprising a vector as described above. In addition, the present invention provides a polypeptide produced by a host cell comprising a vector as described above.

Suitable hosts include E. coli, B. subtilis, P. aerugenosa, S. cerevisiae, and N. crassa. E. coli, in particular E. coli TB-1, TG-2, $DH5_\alpha$, XL-Blue MRF' (Stratagene), SA2821 and Y1090 are preferred hosts. A more preferred host is XL-Blue MRF' or TG02.

In addition to the above, the present invention provides polyclonal antibodies to ACS, pPDH $E1_\alpha$ and $E1_\beta$, and ACL A and B. Such polyclonal antibodies can be produced in accordance with the methods of Examples 2, 4 and 6 or other methods known in the art.

In yet another embodiment, the present invention provides a method of altering the level of an enzyme in a plant cell, a plant tissue, a plant organ or a plant. The method comprises contacting the plant cell, plant tissue, plant organ or plant with a vector comprising a nucleic acid molecule selected from the group consisting of (i) a gene encoding an enzyme or, if the enzyme is comprised of subunits, a subunit of an enzyme selected from the group consisting of plastidic acetyl CoA synthetase, plastidic pyruvate dehydrogenase, ATP-citrate lyase, pyruvate decarboxylase, acetyl CoA hydrolase, mitochondrial pyruvate dehydrogenase and aldehyde dehydrogenase, (ii) a nucleic acid molecule comprising or encoding an antisense molecule to an RNA molecule transcribed from a gene of (i), and (iii) a nucleic acid molecule comprising a ribozyme to an RNA molecule transcribed from a gene of (i). The vector comprising a nucleic acid molecule of (i) increases the level of an enzyme in the plant cell, plant tissue, plant organ or plant, whereas the vector comprising a nucleic acid molecule of (ii) or (iii) decreases the level of an enzyme in the plant cell, plant tissue, plant organ or plant. Preferably, the alteration of the enzyme results in an alteration of the level of acetyl CoA in the plant cell, plant tissue, plant organ or plant. Accordingly, the present invention further provides a plant cell, a plant tissue, a plant organ and a plant in which the level of acetyl CoA has been altered in accordance with the method.

Preferably, the nucleic acid molecule used in the present inventive method is one of those described above or one of those described below. In this regard, nucleic acid molecules that correspond to the above-described plant nucleic acid molecules but which have been isolated from animal, bacterial or yeast sources can be used in the context of the present inventive method to increase the level of an enzyme in a plant cell, a plant tissue, a plant organ or a plant, provided that a cDNA sequence is used in those instances where the animal, bacterial or yeast genomic sequence contains introns that may not be properly processed in a plant. In addition, it may be necessary to alter the cDNA sequence so that it contains codon sequences that are preferred in plant species over animal, bacterial or yeast species. However, to the extent that antisense or ribozyme sequences are employed in the present inventive method, it would be advantageous to use a nucleic acid molecule isolated from a plant that is of the same origin as the plant cell, plant tissue, plant organ or plant in which the level of an enzyme is to be altered.

An isolated or purified nucleic acid molecule encoding PDC for use in the present inventive method can be obtained in accordance with methods known in the art. A cDNA clone encoding PDC1 from maize is available from GenBank as accession number X177555 (genomic DNA X 59546). Partial clones Z21721 and L11312 for PDC-22 and partial clones Z21722 and L11313 for PDC-3 from maize are also available from GenBank. cDNA and deduced amino acid sequences for PDC-1 and PDC-2 from Arabidopsis are provided herein as SEQ ID NOS: 15–18 as set forth in FIGS. 8A–9B. Alternatively, an isolated or purified nucleic acid molecule encoding a PDC that has been modified by one or more insertions, deletions and/or substitutions, wherein the encoded PDC does not differ functionally from the unmodified PDC, can be used. Preferably, the modified PDC converts pyruvate to acetaldehyde preferably at least about 50%, more preferably at least about 75%, most preferably at least about 90% as well as the unmodified PDC as determined by in vitro assay using labeled pyruvate.

An isolated or purified nucleic acid molecule encoding the E2 subunit of pPDH for use in the present inventive method can be obtained in accordance with methods known in the art. A cDNA clone encoding E2 pPDH is available from Mooney et al., Biochemistry Department, University of Missouri (Mooney et al., *Plant Physiol.* 120: 443–451 (1999)). Alternatively, an isolated or purified nucleic acid molecule encoding the E2 subunit of pPDH that has been modified by one or more insertions, deletions and/or substitutions, wherein the encoded E2 subunit of pPDH does not differ functionally from the unmodified E2 subunit of pPDH, can be used. Preferably, a pPDH comprising a modified E2 subunit of pPDH converts pyruvate to acetyl-CoA preferably at least about 50%, more preferably at least about 75%, most preferably at least about 90% as well as a pPDH comprising an unmodified E2 subunit as determined by in vitro assay in the presence of labeled pyruvate.

An isolated or purified nucleic acid molecule encoding ACH can be isolated from a plant for use in the present inventive method using the ACH gene from *Saccharomyces cervisiae* (GenBank Accession No. M31036; Lee et al., *J. Biol. Chem.* 265: 7413–7418 (1990)). For example, existing *Saccharomyces cerevisiae* mutants (Lee et al., *Biochim. Biophys. Acta* 1297(1): 105–109 (1996); and Minet et al., *Plant J.* 2: 417–422 (1992)) can be complemented with a library expressing Arabidopsis cDNAs in a plasmid that can replicate and express those genes in yeast (see, for example, Wang et al., *Plant Molec. Biol.* 31: 1093–1104 (1996)). A clone that can complement the yeast mutant and restore wild-type growth capability is selected. Alternatively, a clone can be obtained by purifying the ACH to homogeneity and obtaining partial N-terminal sequence analysis. This sequence analysis is then reverse translated into a DNA sequence. The DNA sequence is then used to screen a cDNA library from Arabidopsis to find the clone containing the cDNA for ACH.

An isolated or purified nucleic acid molecule encoding mtPDH for use in the present inventive method can be obtained in accordance with methods known in the art. The mtPDH comprises four subunits. A cDNA clone encoding the $E1_\alpha$ subunit of mtPDH from Arabidopsis is described in Luethy et al., *Gene* 164(2): 251–254 (1995). The cDNA clone comprises 1435 bp in which there is a 1167 bp open reading frame encoding a43.0 kD polypeptide of 389 amino acids (pI 7.1). The $E1_\alpha$ subunit from Arabidopsis is 47–51% identical at the amino acid level to other eukaryotic sequences. A cDNA clone encoding the $E1_\beta$ subunit of mtPDH from Arabidopsis is described in Luethy et al., *Biochim. Biophys. Acta* 1187(1): 95–98 (1994). The cDNA clone comprises 1320 bp in which there is a 1089 bp open reading frame encoding a polypeptide of 363 amino acids with a predicted molecular mass of 39,190 Da and an isoelectric point of 4.9. A 29 amino acid presumptive mitochondrial targeting sequence is present at the amino terminus. A cDNA clone encoding the E2 subunit (dihydrolipoamide acetyltransferase) of mtPDH from Arabidopsis is described in Guan et al., *J. Biol. Chem.* 270(10): 5412–5417 (1995). The cDNA clone comprises 2.2 kb. Such sequences can be used in the present inventive method.

Alternatively, an isolated or purified nucleic acid molecule encoding an $E1_\alpha$, $E1_\beta$ or E2 subunit of mtPDH that differs from the $E1_\alpha$ or $E1_\beta$ subunits of the mtPDH of Luethy et al. or the E2 subunit of the mtPDH of Guan et al., respectively, by one or more insertions, deletions and/or substitutions, wherein the modified $E1_\alpha$, $E1_\beta$ or E2 subunit, together with the other unmodified subunits of mtPDH of Luethy et al. or Guan et al., does not differ functionally from an unmodified mtPDH. Preferably, the modified subunit, together with the other unmodified subunits, converts pyruvate to acetyl CoA at least about 70%, preferably at least about 75%, more preferably at least about 85%, most preferably at least about 90% as well as the unmodified mtPDH comprising the subunits disclosed by Leuthy et al. and Guan et al. as determined by in vitro assay in the presence of labeled pyruvate can be used.

An isolated or purified nucleic acid molecule encoding ALDH for use in the present inventive method can be obtained in accordance with the methods set forth in U.S. Pat. No. 5,684,242 (the '242 patent). The '242 patent discloses the nucleic acid sequence of ALDH as SEQ ID NO: 1 and the corresponding amino acid sequence as SEQ ID NO: 2. cDNA and deduced amino acid sequences for ALDH-1, ALDH-2, ALDH-3 and ALDH-4 from Arabidopsis are provided herein as SEQ ID NOS: 19–26 in FIGS. 10A–13. Alternatively, an isolated or purified nucleic acid molecule encoding ALDH that differs from the ALDH of the '242 patent or the Arabidopsis ALDH sequences as set forth herein by one or more insertions, deletions and/or substitutions, wherein the encoded ALDH does not differ functionally from the preceding ALDH, can be used. Preferably, the modified ALDH converts acetaldehyde to acetate preferably at least about 50%, more preferably at least about 75%, most preferably at least about 90% as well as the unmodified ALDH as determined by in vitro assay in the presence of labeled acetaldehyde.

Preferred vectors for use in the present inventive method are characterized as described above. Like vectors, which comprise a nucleic acid encoding PDC, E2 pPDH, ACH, ALDH or mtPDH as described above, also are preferred. Such vectors can be introduced into a plant by any suitable means. For example, cells in tissue culture can be transformed with a vector. This method is particularly useful for plants like maize, for example. Arabidopsis, on the other hand, preferably is transformed using the Agrobacterium-mediated infiltration method (see, e.g., Chang et al., *Plant J.* 5(4): 551–558 (1994); Katavic et al., *Molec. Gen. Genet.* 245(3): 363–370 (1994)).

If it is desired to increase the expression of a given gene, it is preferred to do so by introducing a gene encoding an enzyme or, if the enzyme is comprised of subunits, a subunit of an enzyme selected from the group consisting of plastidic acetyl CoA synthetase, plastidic pyruvate dehydrogenase, ATP-citrate lyase, aldehyde dehydrogenase, mitochondrial pyruvate dehydrogenase, pyruvate decarboxylase and acetyl CoA hydrolase. The gene is preferably introduced by way of a vector. It is preferred that either multiple extra copies of the gene are introduced into the plant cell, plant tissue, plant organ or plant or that a vector comprising a strong promoter, such as the CaMV 35 S promoter, is introduced into the plant cell, plant tissue, plant organ or plant such that the gene is expressed at a higher rate, thereby generating more mRNA, which, in turn, is translated into more of the encoded enzyme. Desirably, expression of an enzyme comprising subunits is increased by increasing the expression of all subunits. Expression of an enzyme comprising subunits can be decreased by decreasing the expression of a single subunit.

In this regard, if expression is desired in a given tissue, a tissue-specific promoter can be used in the vector. Examples of tissue-specific promoters and enhancers include those described in Guerineau, *Methods Mol. Biol.* 49: 1–32 (1995); Meisel et al., *Gent. Eng.* 19: 183–199 (1997); and Edwards et al., *Ann. Rev. Genet.* 24: 275–303 (1990)). Similarly, an organ-specific promoter can be used in the vector. Developmentally specific promoters and inducible promoters also can be used, such as those described in Gruner et al., *Eur. J. Biochem.* 220(1): 247–255 (1994); Caddick et al, *Nat. Biotech.* 16(2): 177–180 (1998); Moore et al., PNAS USA 95(1): 376–381 (1998); and Mett et al., PNAS USA 90(10): 4567–4571 (1993). Malate synthase and isocitrate lyase plant promoters are examples of developmentally specific promoters. Napin, phaseolin, oleosin, glycinin, cruciferin and betaconglycinin are examples of seed storage protein promoters. Inducible promoters, which can be used in those instances where the expression of a given gene is desired after a host plant has reached maturity, include temperature sensitive regulatory elements, heat shock promoters, stress response promoters, and chemically inducible promoters.

If it is desired to decrease the expression of a given gene, it is preferred to do so by introducing either a nucleic acid molecule comprising (i.e., in the case of an RNA vector) or encoding (i.e., in the case of a DNA vector) an antisense nucleic acid molecule to an RNA molecule transcribed from an aforementioned gene or a nucleic acid molecule comprising a ribozyme to an RNA molecule transcribed from such a gene (see, for example, Senior, *Biotech. Genet. Eng. Rev.* 15: 79–119 (1998); Bird et al., *Biotech. Genet. Eng. Rev.* 9: 207–227(1991); Matzke et al., *Trends Genet.* 11(1): 1–3 (1995); Baulcombe, *Plant Mol. Biol.* 32(1–2): 79–88 (1996); Castanatto et al., *Crit. Rev. Eukaryot. Gene Exp.* 2(4): 331–357 (1992); and Rossi, *Trends Biotechnol.* 13(8): 301–306 (1995)). In antisense technology, a nucleic acid segment from the desired plant gene can be cloned and operably linked to the promoter sequence such that the anti-sense strand of RNA is transcribed. For example, the 35 S promoter from CaMV can be fused to a cDNA encoding a given enzyme but in opposite orientation from normal.

The nucleic acid sequence introduced in antisense suppression generally is substantially identical to at least a portion, preferably at least about 20 continuous nucleotides, of the endogenous gene or gene to be repressed, but need not be identical. The vectors can, thus, be designed such that the inhibitory effect applies to other proteins within a family of genes exhibiting homology or substantial homology to the target gene. The introduced sequence also need not be full-length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective.

The plant cell, plant tissue, plant organ or plant is then contacted with the construct and the anti-sense strand of RNA is produced. In plant cells, it has been shown that anti-sense RNA inhibits gene expression (see, e.g., Sheehy et al., PNAS USA 85: 8805–8809 (1988); and Hiatt et al., U.S. Pat. No. 4,801,340). The resulting recombinant gene can be transformed into Arabidopsis plants, for example, using Agrobacterium-mediated transformation. Inhibition of expression of a given gene can be confirmed in a transformed plant cell by standard methods for measuring the presence and/or activity of a given enzyme. In this regard, it is important to point out that some plants, such as Arabidopsis, contain two genes, i.e., "paralogs," encoding a given enzyme, such as ACL, PDC and ALDH. In such instances, it is desirable to decrease the expression of a given gene with antisense RNA because the paralogous genes generate mRNAs that are nearly identical in sequence (as is the case of ACL, PDC and ALDH mRNAs) and, therefore, a single antisense RNA molecule can reduce and even block the expression of both paralogs, depending on the antisense molecule utilized.

Ribozymes also have been reported to have use as a means to inhibit expression of endogenous plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered and is, thus, capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988). Preferably, the ribozyme comprises at least about 20 continuous nucleotides complementary to the target sequence on each side of the active site of the ribozyme.

Techniques for contacting a plant cell, a plant tissue, a plant organ or a plant with a vector so that the vector is taken up by a plant cell, alone or as part of a plant tissue, a plant organ or a plant, and expressed therein are known in the art. Such methods involve plant tissue culture techniques, for example. Herein, "contacting" is intended to mean that the cell, tissue, organ or plant is brought into contact with the vector in such a manner that the vector enters the cell and is expressed therein.

The plant cell, plant tissue, plant organ or plant can be contacted with the vector by any suitable means, including direct transformation, e.g., polyethylene glycol precipitation (Paszkowski et al., *EMBO J.* 3: 2717–2722 (1984), cell bombardment, i.e., attaching the DNA to metallic pellets and blasting them through the plant's cell wall (Fromm et al., *Bio/Technology* 8: 833–839 (1990); Gordon-Kamm et al., *Plant Cell* 2: 603–618 (1990); and Klein et al., *Nature* 327: 70–73 (1987)). Exogenous DNA can be introduced into a dicotyledonous plant cell by insertion of the nucleic acid encoding a gene involved in acetyl CoA production into the Ti plasmid of Agrobacterium and adding suitable ingredients to promote transformation thereby (Horsch et al., *Science* 223: 496–498 (1984); Fraley et al., PNAS USA 80: 4803 (1983); and DeBlock et al.,*EMBO J.* 3: 1681–1689 (1984)). Other techniques are available for the introduction of exogenous DNA into a plant and/or a subset of its constituent cells, including electroporation (Fromm et al., PNAS USA 82: 5824 (1995), microinjection, protoplast-mediated gene transfer, and silicon carbide crystal-mediated gene transfer. These various techniques are discussed in *Genetic Engineer-*

*ing News* 14(4): at pages 1, 3 and 24, and are generally known in the art. See, for example, Weising et al., *Ann. Rev. Genet.* 22: 421–477 (1988)).

Transformed plant cells, which are derived by any of the above transformation techniques can be cultured to regenerate a whole plant, which possesses the desired transformed phenotype. Plant regeneration from cultured protoplasts is described in Evans et al., *Protoplast Isolation and Culture, Handbook of Plant Cell Culture,* MacMillan Publishing Co., New York, pp. 124–176 (1983); and Binding, *Regeneration of Plants, Plant Protoplasts,* CRC Press, Boca Raton, pp. 21–73 (1985). Regeneration also can be obtained from plant callus, explants, organs or parts thereof. Such regeneration techniques are described generally in Klee et al., *Ann. Rev. of Plant Phys.* 38: 467–486 (1987).

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Another method of decreasing acetyl CoA levels is co-supression. See, for example, Que et al., *Dev. Genet.* 22(1): 100–109 (1998) and Smyth, *Curr. Biol.* 7(12): R793–R795 (1997).

Alternatively, reverse genetics systems, which are well-known in the art, can be used to generate and isolate down-regulated or null mutants. One such system, the Trait Utility System for Corn, i.e., TUSC, is based on successful systems from other organisms (Ballinger et al., PNAS USA 86: 9402–9406 (1989); Kaiser et al., PNAS USA 87: 1686–1690 (1990); and Rushforth et al., *Mol. Cell. Biol.* 13: 902–910 (1993)). The central feature of the system is to identify Mu transposon insertions within a DNA sequence of interest in anticipation that at least some of these insertion alleles will be mutants. To develop the system in corn, DNA was collected from a large population of Mutator transposon stocks that were then self-pollinated to produce F2 seed. To find Mu transposon insertions within a specified DNA sequence, the collection of DNA samples is screened via PCR using a gene-specific primer and a primer that anneals to the inverted repeats of Mu transposons. A PCR product is expected only when the template DNA comes from a plant that contains a Mu transposon insertion within the target gene. Once such a DNA sample is identified, F2 seed from the corresponding plant is screened for a transposon insertion allele. Transposon insertion mutations of the an1 gene have been obtained via the TUSC procedure (Bensen et al., *Plant Cell* 7: 75–84 (1995)). This system is applicable to other plant species, at times modified as necessary in accordance with knowledge and skill in the art.

T-DNA insertional mutagenesis can be used to generate insertional mutations in one of the above-mentioned genes so as to affect adversely the expression of a given gene. Theoretically, about 100,000 independent T-DNA insertions are required for a 95% probability of getting an insertion in any given gene (McKinnet, *Plant J.* 8(4): 613–622 (1 995); and Forsthoefel et al., *Aust. J. Plant Physiol.* 19: 353–366 (1992)). Currently, there are 2,000 such T-DNA-tagged lines that are publicly available. Additional T-DNA-tagged lines are being generated and are being made available. In this regard, Monsanto (St. Louis, Mo.) currently has a collection of T-DNA tagged lines, which are reported to contain 90,000–150,000 T-DNA insertions. T-DNA tagged lines of plants can be screened using PCR. For example, a primer can be designed for one end of the T-DNA and another primer can be designed for the gene of interest and both primers can be used in PCR. If no PCR product is obtained, then there is no insertion in the gene of interest. In contrast, if a PCR product is obtained, then there is an insertion in the gene of interest. Insertional mutations, however, often generate null alleles, which can be lethal. Alternatively, if there is more than one gene that encodes for a given enzyme, a mutation in one of the genes may not result in decreased expression of the enzyme encoded by the gene.

Another alternative method to decrease expression of a given gene is to use a compound that inhibits expression of one of the above-mentioned genes or that inhibits the activity of the enzyme encoded by one of the above-mentioned genes. For example, glucose is known to inhibit PDC.

In addition to the above, gene replacement technology can be used to increase or decrease expression of a given gene. Gene replacement technology is based upon homologous recombination (see, Schnable et al., *Curr. Opinions Plant Biol.* 1: 123 (1998)). The nucleic acid of the enzyme of interest can be manipulated by mutagenesis (e.g., insertions, deletions, duplications or replacements) to either increase or decrease enzymatic function. The altered sequence can be introduced into the genome to replace the existing, e.g., wild-type, gene via homologous recombination (Puchta and Hohn, *Trends Plant Sci.* 1: 340 (1996); Kempin et al., *Nature* 389: 802 (1997)).

Also in addition to the above, organelle re-targeting can be used to increase or decrease expression of a given gene involved in acetyl CoA production. For example, one of the above-mentioned genes can be modified by removing its organelle-targeting sequence and replacing it with a novel organelle-targeting sequence (see, for example, Roesler et al., *Plant Physiol.* 113(1): 75–81 (1997) in re retargeting of a cystolic enzyme to the plastids; Moloney et al., *Biotechnol. Genet. Eng. Rev.* 14: 321–336 (1997); deCastro Silva et al., *Plant Mol. Biol.* 30(4): 769–780 (1996); and Cline et al., *Ann. Rev. Cell Dev. Biol.* 12: 1–26 (1996)). The altered sequence can then be introduced into the plant genome via standard transformation procedures.

The activity of a given enzyme can be measured by using labeled substrates in vitro. ACS activity can be assayed quickly and conveniently in vitro by incubating whole chloroplasts, chloroplast extracts or leaf extracts with labeled acetate, CoA, ATP and Mg and transferring aliquots of the reaction mixture to pieces of either Whatman No. 1 or DE81 filter paper as described by Roughan et al., *Analyt. Biochem.* 216: 77–82 (1994). The paper pieces are then washed to remove unreacted acetate. Acetyl CoA, which binds quantitatively to the paper, is then determined by scintillation counting. If desired, ACS can be further purified as described by Zeiher et al., *Plant. Physiol.* 96: 382–389 (1991) for use in in vitro assays.

Reducing pPDH in accordance with the above method is expected to result in a decrease in the pool of plastidic acetyl CoA, which, in turn, is expected to affect de novo fatty acid biosynthesis, i.e., synthesis of 18-carbon fatty acids. This would be most readily observable as a reduction in the accumulation of seed oils.

Reducing cytosolic ACL is expected to result in a decrease in the pool of cytosolic acetyl CoA, which, in turn, is expected to affect the biosynthesis of very long chain fatty acids and flavonoids. This would be most readily observable as a reduction of seed coat color (due to reduced flavonoids), a reduction of cuticle deposition on the aerial portion of the plant, and a reduction in 20- and 22-carbon fatty acids in the seed oil (due to reduced elongation of 18-carbon fatty acids).

Reducing PDC, ALDH and/or ACS is expected to affect the acetyl CoA pool. The reduction of ALDH is known to affect pollen development in plants (see U.S. Pat. No. 5,684,242).

Whether or not a given acetyl CoA-generating pathway affects another acetyl CoA pathway can be determined by measuring the effect on expression of acetyl CoA-generating genes and by measuring the generation of acetyl CoA pools in vivo. For example, using a transgenic plant, it can be determined whether or not the reduction in a given acetyl CoA generating enzyme causes compensatory alterations in the expression of other genes. As microarray chip technology becomes established and available (DeRisi et al., *Science* 278: 680–686 (1997)), the effect of a given genetic alteration on the expression of all cloned genes of Arabidopsis can be determined. Metabolic radiotracer studies can be performed to measure the generation of different acetyl CoA pools in vivo. In such studies, radioactively labeled precursors are provided to intact tissues and the radioactive label is monitored as the precursor is metabolized. By comparing wild-type plants and plants that have reduced activities of one of the acetyl CoA-generating enzymes, the source of different acetyl CoA pools can be determined as well as the effect of the reduction in a given acetyl CoA generating enzyme.

In addition to being useful in the study of acetyl CoA generation in plants, including the spatial and temporal patterns of expression of genes encoding enzymes required for acetyl CoA generation, the above-described method is useful in the generation of plants for the production of acetyl CoA-derived phytochemicals. The method is useful in the alteration of acetyl CoA levels in plants, including wild-type and mutant plants, such as alfalfa, corn, wheat, sorghum, barley, rice, oats, rye, soybean, rapeseed, canola, cotton, safflower, peanut, palm, sunflower, beet, and various vegetable and fruit crops, such as cucumber, tomato, peppers, and the like. By "alteration" is meant that the acetyl CoA level in a given plant (or plant cell, tissue or organ) is different as a result of the practice of the present inventive method as compared to a like plant, the acetyl CoA level of which has not been altered as a result of the practice of the present inventive method.

In view of the above method, the present invention also provides a bacterium, a yeast, an animal, including a cell, tissue or organ thereof, or a plant, including a cell, tissue or organ thereof, in which the level of an enzyme has been altered in accordance with the above-described method. Preferably, the present inventive method is used to generate a plant cell, a plant tissue, a plant organ or a plant. The plant cell can be cultured and kept as plant tissue culture cells or certain plant hormones known in the art can be added to the culture medium, thereby causing the plant tissue culture cells to differentiate and thereby form a new plant variety. Such plant culturing methods useful in the performance of this aspect of the invention are well known in the art. Accordingly, the present invention also provides a plant cell, a plant tissue, a plant organ and a plant in which the level of an enzyme has been altered. Preferably, the alteration of the level of an enzyme results in an alteration of the level of acetyl CoA.

The above method can be adapted for in vitro production of acetyl CoA, which, in turn, can be used to produce acetyl CoA phytochemicals. For example, the various enzymes required for acetyl CoA synthesis can be prepared from a suitable host and placed in a reaction vessel with suitable substrates, an energy source, co-factors and other ingredients known in the art so as to produce acetyl CoA.

EXAMPLES

The present invention is described further in the context of the following examples. These examples serve to illustrate further the present invention and are not intended to limit the scope of the invention.

Example 1

This example describes the cloning of ACS cDNA from Arabidopsis and the comparison of its sequence with ACS from *E. coli* and *S. cerevisiae*.

The deduced amino acid sequences of the ACS genes from *E. coli* and *S. cervisiae* were used to search the dbEST database (National Library of Medicine, National Institutes of Health, Bethesda, Md.) using the program BLAST. One *Arabidopsis thaliana* cDNA clone was identified as a possible ACS gene. This clone, 220J9T7 (accession number N38599), was obtained from the Arabidopsis Biological Research Center (ABRC) at Ohio State University.

Plasmid DNA from this clone was prepared and sequenced by the Biotechnology Instrumentation Facility of Iowa State University. Analysis of the sequence data revealed that this clone (J9) encoded approximately 40% of the C-terminal portion of ACS. Repeated searches of the dbEST database failed to reveal any longer clonal sequences.

cRACE (Maruyama et al., *Nucleic Acids Research* 23: 3796–3797 (1995)) was used to isolate the rest of the ACS gene. mRNA from *Arabidopsis thaliana* was prepared from fresh plant tissue. Nesting ACS-specific primers, based on the 5' end sequence of J9, were used in two sequential cDNA synthesis reactions to generate a specific single-stranded, antisense cDNA fragment encoding a fragment of ACS DNA 5' to the known J9 sequence. Ligation and circularization of this single-stranded cDNA by RNA ligase was followed by two sequential PCR amplifications, using nesting primer pairs based on J9 sequence. This process yielded an approximately 320 bp fragment of DNA encoding a further portion of the ACS gene. This fragment was cloned into the vector pBS (Stratagene), named J9E1, and sequenced.

The remainder of the ACS gene was obtained by PCR amplification of an *Arabidopsis thaliana* cDNA library constructed in the vector pSPORT (Life Technologies, Grand Island, N.Y.). Two nesting antisense primers were designed and synthesized that hybridize to the 5' terminus of J9E1. These primers were used in conjunction with two nesting sense vector primers specific to the vector pSPORT to amplify sequentially by PCR a further 270 bp fragment of ACS cDNA. This fragment was cloned in pBS, given the name J9E2, and sequenced.

Likewise, two more nesting antisense primers were designed and synthesized that corresponded to the 5' terminus of J9E2. Sequential PCR amplification of the cDNA library with these primers and the vector primers yielded a cDNA fragment encoding the rest of the ACS gene. This fragment was cloned in pBS, named J9E3, and sequenced.

All of the sequence data from clones J9, J9E1, J9E2 and J9E3 were aligned and condensed to give a single DNA sequence encoding the complete *Arabidopsis thaliana* ACS gene. This sequence was submitted to GenBank as accession no. AF036618. This DNA encodes a protein of 693 amino acids and has a calculated molecular weight of 76,678 daltons.

MACAW alignment of the cDNA sequence of ACS from Arabidopsis with the protein sequence of ACS from *E. coli* and the protein sequences of the two isoforms of ACS from S. cerevisiae shows that the ACS from Arabidopsis is 53% identical to the ACS from E. coli and 37% identical to the I isoform of ACS from S. cerevisiae and 40% identical to the II isoform of ACS from S. cerevisiae.

Example 2

This example describes the production of a polyclonal antibody to ACS from Arabidopsis.

PCR primers were designed such that the coding region of clone J9 would be amplified by PCR as a DNA fragment terminated by restriction sites suitable for cloning into the E. coli protein expression vector pMALC-2 (New England Biolabs, Beverly, Mass.). The expression vector clone J9-NT1/pMALC-2 was constructed according to the instructions furnished by the supplier of the vector. This clone, when transformed into E. coli and induced with isopropylthio-β-galactoside (IPTG), caused the production of a recombinant chimeric fusion protein consisting of the C-terminal portion of Arabidopsis thaliana ACS fused to the E. coli maltose binding protein (MBP). This recombinant protein was purified from one liter cultures of transformed E. coli and purified using the amylose column supplied by New England Biolabs, according to the manufacturer's protocols. The purified protein was assayed electrophoretically for purity, quantitated, and given to the Biotechnology Instrumentation Facility of Iowa State University for production of polyclonal antibodies in rabbits. Pre-immune and immune sera from the rabbits were tested for specificity and titer by immunoblotting against the original antigen recombinant protein.

Example 3

This example describes the cloning of cDNA for the $E1_\alpha$, $E1_\beta$ and E3 subunits of pPDH and the comparison of the sequence of the cDNA encoding the $E1_\beta$ subunit with the sequence of pPDH from red algae and mtPDH from Arabidopsis.

The dbEST database was searched with the deduced amino acid sequences of the $E1_\alpha$ and $E1_\beta$ subunits of PDH from Porphyra purpurea using the program BLAST. Clones identified as possible pPDHs were obtained from the ABRC at Ohio State University.

Arabidopsis thaliana EST clone 232D14T7 (N65567) and 232D13T7 (N65566) displayed a significant degree of homology to the $E1_\alpha$ subunit of PDH from Porphyra purpurea. Both clones contain identical nucleotide sequences encoding all but the first 50–70 amino acids of the $E1_\alpha$ subunit of pPDH, based on homology to other $E1_\alpha$ subunits of PDH. Clone 232D14T7 (D14) was chosen for sequencing. The DNA sequence of this clone comprises SEQ ID NO: 3 and the deduced amino acid sequence comprises SEQ ID NO: 4 (see FIG. 2 and Sequence Listing).

Arabidopsis thaliana EST clones 163C 12T7 (R2996; $E1_\beta$-1) and 169K3T7 (R64987; $E1_\beta$-1) displayed a significant degree of homology to the $E1_\beta$ subunit of PDH of Porphyra purpurea. These two clones are related to, but not identical to, the corresponding mtPDH of Arabidopsis thaliana. Clone 163C12T7 (C12) was chosen for sequencing. Clone C12 appears to encode almost all of the coding region of the $E1_\beta$ subunit of pPDH. The sequence of this clone comprises SEQ ID NO: 5 and the deduced amino acid sequence comprises SEQ ID NO: 6 (see FIG. 3 and Sequence Listing). A second $E1_\beta$ subunit gene ($E1_\beta$-2) was discovered in Arabidopsis by searching through the Arabidopsis genome sequence in Genbank. Careful analysis showed that the genomic sequence in the database was different from the cDNA sequence of $E1_\beta$-1. Thus, all of the cDNA EST clones were requested from the Arabidopsis Biological Resource Stock Center (Ohio State University, Columbus, Ohio) and sequenced. The cDNA sequences of $E1_\beta$-1 and $E1_\beta$-2 are nearly identical.

Genes encoding the E3 subunit of pPDH from Arabidopsis were isolated as follows. The Arabidopsis EST database was searched using the E3 gene for the cyanobacterium Synechocystis PCC 6803 (Engels et al., Microbiology 143: 3543–3553 (1997)). Two partial cDNA clones were obtained from the Arabidopsis Biological Resource Stock Center. The sequences were used as probes to screen a cDNA library. Near full-length clones were isolated. The genes were translated and transcribed in vitro and to verify that the genes were plastidic as opposed to mitochondrial. The translated proteins were imported into isolated chloroplasts and processed to mature form.

MACAW alignment of the cDNA sequence of $E1_\beta$ pPDH from Arabidopsis with the protein sequence of pPDH from red algae and the protein sequence of the mtPDH from Arabidopsis shows that the pPDH from Arabidopsis is 68% identical to the pPDH from red algae and 37% identical to the mtPDH from Arabidopsis.

Example 4

This example describes the production of polyclonal antibodies to the $E1_\alpha$ and $E1_\beta$ subunits of chloroplastic PDH.

Primers were designed such that the coding regions of D14 and C12 of Example 3 were incorporated into the E. coli expression vector pET24-a. After assembly of these two expression constructs, an expression cassette consisting of the vector promoter, the C 12 coding sequence, and the vector terminator was excised from the C 12 expression plasmid and incorporated into the D1 4 expression plasmid, yielding a tandem expression plasmid capable of simultaneously expressing both subunits of pPDH. These recombinant pPDHs were expressed in E. coli as insoluble inclusion bodies. These inclusion bodies were purified to near homogeneity. The resulting protein was sent to the Biotechnology Instrumentation Facility of Iowa State University for production of polyclonal antibodies in rabbits. Pre-immune and immune sera from the rabbits were tested for specificity and titer by immunoblotting against the original antigen recombinant proteins.

Example 5

This example describes the cloning of cDNA for the A and B subunits of ACL from Arabidopsis.

The cDNA clones pACL-A1 and pACL-B1 were identified by sequence similarity searches of the Arabidopsis EST (Expressed Sequence Tags) database. The EST cDNA pACL-A1 (clone ID TASG097, Genbank accession #Z18045) was identified because the sequence of its 5'-end was similar to the sequence of the 5'-end of the human ATP-citrate lyase. The EST cDNA pACL-B 1 (clone ID VBVYC01, Genbank accession #Z33810) was identified because the sequence of its 5'-end was similar to the sequence near the middle of the human ATP-citrate lyase. These two clones were obtained from the Arabidopsis Biological Resource Center (Ohio State University). Both strands of both clones were sequenced at the Iowa State University DNA Sequencing Facility, using an ABI automatic sequencer.

The ACL-A2 sequence was identified by a BLAST sequence search of the publicly available data generated by the Arabidopsis Genome Initiative (http://genome-www.stanford.edu/Arabidopsis/agi.html). ACL-A2 is an Arabidopsis gene that is paralogous to the ACL-A1 cDNA. That is, the ACL-A2 gene codes for the same protein as the ACL-A1 cDNA, but based on the fact that the 5'- and 3'-untranslated regions of these two sequences are different, these two sequences represent different members of the ATP-citrate lyase gene family.

The ACL-B2 sequence was identified by screening an Arabidopsis cDNA library prepared from polyA RNA isolated from developing siliques of Arabidopsis (Castle and Meinke, Oklahoma State University, Stillwater) in the vector lambda gt10 with radioactively labeled ACL-B1 cDNA as described by Sambrook et al. (1989), supra. Briefly, approximately 200,000 recombinant phage from the library were grown on petri plates and replicated to nitrocelluose membranes. Replica filters were incubated at 65° C. in hybridization solution (5×SSC, 1×Denhardt's solution, 0.2% (w/v) SDS, 10 mM EDTA, 0.1 mg/ml salmon sperm DNA, 10% (w/v) dextran sulfate, 50 mM Tris-HCI, pH 8.0) with $^{32}$P-labeled probe for 12 hr. After hybridization, filters were washed at 65° C. in 2×SSC, 0.5% (w/v) SDS, and subsequently with 0.1×SSC and 0.1% (w/v) SDS. Recombinant plaques that hybridized with the probe were plaque-purified and a cDNA insert was subcloned into the plasmid vector pBSK for sequencing purposes. The resulting sequence was termed ACL-B2, which is a full-length cDNA clone coding for the ACL-B subunit and is encoded by a separate gene from ACL-B 1. The nucleotide sequences of ACL-B 1 and ACL-B2 share about 80% identity and encode polypeptides that are over 95% identical.

ACL-A1, ACL-A2, ACL-B1 and ACL-B2 share a high degree of sequence identity with rat and human ACL. The human ACL MRNA is 4.3 kb in length and codes for a protein of 1100 residues. The ACL-A1 mRNA is 1.5 kb in length and codes for a protein of 423 residues that is 50% identical to the N-terminus of the human ACL. The ACL-A2 gene codes for a MRNA that is a paralog of the ACL-A1 mRNA; they each code for proteins that are over 98% identical even though their nucleotide sequences are only about 80% identical and their 5'- and 3'-untranslated regions are distinct. The ACL-A2 gene comprises 12 exons and 13 introns. The partial ACL-B I cDNA is 1.03 kb in length and codes for a polypeptide of 272 residues that is 50% identical to the C-terminus of the human ACL. The full-length ACL-B1 mRNA is 2.2 kb in length.

The deduced ACL-A and ACL-B polypeptides have no recognizable targeting sequence and, as with the rat and human ACL polypeptides, they are cytosolic.

Numerous sequence databases were searched for additional orthologs of the ACL-A and ACL-B polypeptides. No orthologs were identifiable in the entire genome of the yeast Saccharomyces cerevisiae, which is consistent with the absence of ACL activity in this species (Kohlhaw and Tan-Wilson, *J. Bacteriol.* 129: 1159–1161 (1977)). However, orthologs of ACL-A and ACL-B have been identified in the yeast *Schizosaccharomyces pombe.* The ACL-A ortholog is a clone of a gene that resides on chromosome 1 of *S. pombe,* and its amino acid sequence is over 60% identical to Arabidopsis ACL-A. The ACL-B ortholog from *S. pombe* is a partial cDNA clone, and its amino acid sequence shares 60% identity with that of the Arabidopsis ACL-B. Both *S. pombe* orthologs have been identified as ATP citrate lyases due to the high degree of sequence identity to the animal ACL.

The ACL-B and ACL-A mRNAs are transcribed from two different genes. Evidence for this conclusion comes from a series of experiments. First, Arabidopsis DNA was digested with Xba I, Sac I, Hin dIII, Eco RI, and Bam HI and subjected to Southern blot hybridization using as a probe the ACL-A1 cDNA and the ACL-B cDNA. Hybridization analyses of the Arabidopsis DNA probed individually with the two cDNAs revealed that each cDNA hybridized to a nonoverlapping set of restriction fragments. Second, screening of a lambda-based Arabidopsis genomic library with pACL-A and pACL-B resulted in the isolation of two nonoverlapping sets of genomic clones that hybridize with each of the two cDNAs. Restriction digests and Southern blot analyses of the 12 genomic clones that hybridize to pACL-A enabled subclassification of the clones into two groups, which is consistent with the data from the genomic Southern blot that indicates that the ACL-A mRNA is encoded by a small gene family. Based on similar analyses, the eight pACL-B hybridizing genomic clones were subclassified into three groups, which is consistent with the data from the genomic Southern blot that indicates that the ACL-B MRNA is encoded by a small gene family. Third, the sequence of a BAC clone containing one of the ACL-A genes (ACL-A1) indicates that an ACL-B gene is not within 10 kb of the ACL-A1 gene. The ACL-Al gene is located on chromosome 1 of Arabidopsis, and the gene sequence is interrupted by 11 introns.

Example 6

This example describes the production of polyclonal antibodies to the A and B subunits of ACL.

The ACL-A and ACL-B sequences were expressed in *E. coli* using the pET 30 expression vector (Novagen, Madison, Wis.). The expressed proteins were then purified by preparative SDS-PAGE and were used to immunize rabbits to obtain antisera.

These antisera were used to probe Western blots of Arabidopsis seedling extracts. Anti-ACL-A detected a single polypeptide of 45-kDa, which is very close to the molecular weight predicted from the sequence of pACL-A (which encodes for a 423 residue polypeptide). Anti-ACL-B antibodies detected a polypeptide of about 70-kDa, which is close to that predicted based upon the size of the ACL-B MRNA (2.2-kb).

Example 7

This example describes how the cDNA encoding ACH from *Saccharomyces cerevisiae* can be used to isolate the mtACH gene from a plant.

A cDNA clone encoding a plant mtACH can be identified by sequence similarity searches of the Arabidopsis EST (Expressed Sequence Tags) database (Arabidopsis Genome Initiative) to the yeast ACH cDNA. Positive clones can then be obtained from the ABRC (Ohio State Resource Center). Both strands of the positive clones can then be sequenced, for example by using an ABI automatic sequencer.

Given that recent efforts to identify a mtACH EST from this database have not yielded any positive clones (which could be due to the fact that the Arabidopsis Genome Initiative only contains about 20% of the genome), a plant mtACH gene can be cloned from Arabidopsis by complementation of the existing *Saccharomyces cerevisiae* mutants (Lee et al. (1990), supra). The mutant can be transformed with a library expressing Arabidopsis cDNAs in a plasmid that would replicate and express those genes in yeast (Minet et al., *Plant J.* 2: 417–422 (1992)). A clone can then be selected that complements the Saccharomyces mutant and restores (e.g., wild-type) growth capability. The Arabidopsis cDNA for ACH can then be copied by PCR and the DNA fragment can then be cloned in pBS for sequencing.

Alternatively, antisera to the yeast ACH can be generated and used to isolate mtACH from a plant. The amino acid sequence of the isolated mtACH can the be determined in whole or in part. The sequence can then be used to generate nucleic acid probes for screening a cDNA library or a genomic library in order to isolate the mtACH gene from plants. The mtACH gene from plants can then be sequenced.

If desired, antisera against the isolated plant mtACH can be used to screen an expression library for expression of mtACH. Antisera can be produced in rabbits using transgenically expressed protein from E. coli. For example, the Arabidopsis cDNA for ACH can be cloned into the pET24 expression vector as a translational fusion. The plasmid can then be transformed into E. coli, where it would express the protein. The protein, which accumulates as an inclusion body within the bacterium, can then be purified by centrifugation and SDS-gel electrophoresis. The protein can then be supplied to the Biotechnology Instrumentation Facility at Iowa State University for the production of polyclonal antibodies in rabbits. Pre-immune and immune sera from rabbits can then be tested for specificity and titer by immunoblotting against the original antigen recombinant protein.

Example 8

This example describes the cloning of ALDH cDNAs from Arabidopsis.

The deduced amino acid sequence of the maize mitochondrial ALDH, coded by the rf2 gene (Cui et al., Science 272: 1334–1336 (1996)) was used to search the dbEST database (National Library of Medicine, National Institutes of Health, Bethesda, Md.) using the program BLAST. This resulted in the identification of 7 Arabidopsis EST cDNA clones (Genbank Accession #R83958, Z26417, N96630, T13678, R86795, AA041030, AA395226), which were obtained from the Arabidopsis Biological Research Center (ABRC) at Ohio State University, and they were each sequenced. All seven clones were partial cDNA. Using these EST cDNAs as probes, Arabidopsis cDNA libraries were screened as described in Example 5. This resulted in the isolation of full-length cDNA clones that corresponded to four gene products, ALDH1, ALDH2, ALDH3, ALDH4. The nucleotide and deduced amino acid sequences of the Arabidopsis ALDH1 (FIGS. 10A and 10B), ALDH2 (FIGS. 11A and 11B), ALDH3 (FIGS. 12A and 12B) and ALDH4 (FIG. 13) are presented. BLAST sequence searches of the publicly available data generated by the Arabidopsis Genome Initiative, with ALDH1, ALDH2, ALDH3 and ALDH4 nucleotide sequences confirmed that these cDNAs are products of four distinct genes. These genes occur on chromosomes 3, 3, 1 and 4, respectively, of Arabidopsis. Of these sequences, ALDH1 and ALDH3 encode the most similar proteins (they share 85% sequence similarity), whereas the similarity between ALDH1 and ALDH3 is lower (66%), and the similarity between ALDH1 and ALDH4 is even lower (40%).

Example 9

This example describes the cloning of PDC cDNAs from Arabidopsis.

The nucleotide sequences of the two Arabidopsis PDC genes (PDC1, Genbank accession #U71122, and PDC2, Genbank accession #U71122) were used to search the dbEST database (National Library of Medicine, National Institutes of Health, Bethesda, Md.) using the program BLAST. This resulted in the identification of 6 Arabidopsis EST cDNA clones, which were obtained from the Arabidopsis Biological Research Center (ABRC) at Ohio State University, and they were sequenced. All six clones were partial cDNA clones, three of which (Genbank accession #F14476, T04727 and F 14475) matched the PDC1 gene sequence, and the other three (Genbank accession #N97215, Z35007 and AA597828) matched the PDC2 gene sequence. Using these EST cDNAs as probes, Arabidopsis cDNA libraries were screened as described in Example 5. This resulted in the isolation of full-length cDNA clones corresponding to the PDC1 and PDC2 genes. The nucleotide and deduced amino acid sequences of the Arabidopsis PDC1 (FIG. 8) and PDC2 (FIG. 9) are presented. The PDC1 and PDC2 cDNAs share 75% sequence identity, and they encode proteins that share 82% sequence identity or 87% sequence similarity. BLAST sequence searches of the publicly available data generated by the Arabidopsis Genome Initiative, with PDC1 and PDC2 nucleotide sequences confirmed that these cDNAs are products of two distinct genes. These genes occur on chromosomes 4 and 5, respectively, of Arabidopsis.

Example 10

This example describes the accumulation of ACL-A, ACL-B, PDH and ACS mRNAs determined by RNA blot analysis during stages of plant development.

RNA was extracted from Arabidopsis leaves, buds, flowers, and siliques as described previously (Weaver et al., Plant Physiol. 110: 1021 (1995)). Radioactive ACL-A and ACL-B RNAs were obtained by in vitro transcription from the respective pBSK clones. The RNA concentrations were determined from the absorbance at 280 and 260 nm.

Ten $\mu$g of RNA from each tissue sample were fractionated by electrophoresis in formaldehyde-containing agarose gels. After transfer of the RNA to nylon membranes, hybridizations were conducted in a buffer containing 50% formamide at 650° C. for 12–16 hr using $^{32}$P-labeled RNA probes. Hybridized membranes were rinsed twice with 2=SSC, 2% SDS for 10 min at room temperature, and then washed twice with 0.1×SSC, 0.1% SDS for 20 min at 65° C. The membranes were exposed to a phosphor screen (Molecular Dynamics, Sunnyvale, Calif.) for 4 hr, and the radioactivity in each band was quantified with a Storm 840 PhosphorImager (Molecular Dynamics).

The accumulation patterns of the ACL-A and ACL-B mRNAs were identical at the level of resolution afforded by these techniques. During silique development, ACL-A and ACL-B mRNAs accumulated to the highest levels in flower buds and in developing siliques about 1–4 days after flowering. However, both ACL-A and ACL-B levels tapered off in the siliques at around 8 days after flowering and were barely detectable in the siliques at 15 days after flowering.

The absolute level of PDH E1$_\beta$ subunit MRNA accumulation (per total RNA) was greater than that of ACS MRNA in siliques at all stages of development. PDH E1$_\beta$ subunit MRNA accumulation was very high in siliques containing seeds undergoing rapid oil accumulation (5–7 days after flowering).

Example 11

This example describes the spatial and temporal patterns of expression of pPDH, ACS and ACL determined by in situ hybridization.

Arabidopsis siliques (1 to 13 days after flowering) and flower buds were harvested and cut into 3–4 mm long pieces. Tissues were fixed, dehydrated, embedded and sectioned as previously described (Wang et al., *Amer. J. Bot.* 82: 1083 (1995); and Ke et al., *Plant Physiol.* 113: 357 (1997)).

$^{35}$S-labeled probes were transcribed from vectors containing the ACL-A, ACL-B, E1$_\beta$pPDH or ACS cDNA (cloned in pBluescript SK). The labeled probes were hybridized to the tissue sections by as described in Ke et al. (1997), supra.

After hybridization, the tissue sections were coated with Kodak NTB2 emulsion, exposed for 2 to 4 days, and developed. Photographs were taken with an Orthopha microscope (Leitz, Wetzlar, Germany) using bright-field optics.

In situ hybridizations were repeated three times, using two sets of plant materials that had been independently processed, all with similar results. Control slides containing sections of siliques were hybridized with sense RNA probes transcribed from the vectors indicated above, and virtually no signal was detected in these slides.

Using in situ hybridization to RNA, the spatial and temporal patterns of expression of pPDH, ACS, ACL-A and ACL-B were determined and were found to be heterogeneous. Accumulation of PDH mRNA was very high in torpedo-staged and walking-staged embryos, the stages in which oil accumulation is also highest. The pattern was almost identical to that of heteromeric acetyl CoA carboxylase (ACC). These results implicate pPDH as the source of the plastidic pool of acetyl CoA. In contrast to the pPDH E1$_\beta$subunit MRNA, the MRNA coding for ACS accumulated to only very low levels in embryos of Arabidopsis, with maximal accumulation occurring in heart stage embryos, after which accumulation decreases. Instead, the ACS MRNA accumulated to the highest levels in the root tips of radicles of embryos in seeds from 1–4 days after imbibition, in anther filaments (especially near the junction of the filament and anther), and in the funiculus throughout seed development. Very high expression of ACS in filaments is consistent with some role of plastidic acetyl CoA in this organ. While ACS does not appear to be important in providing acetyl CoA for fatty acid synthesis for oils, the spatial and temporal expression of pPDH is consistent with this enzyme being associated with the production of acetyl CoA for oil biogenesis in developing seeds. The spatial and temporal patterns of ACL-A and ACL-B mRNAs were identical at the level of resolution afforded by these techniques. ACL-A and ACL-B mRNAs accumulated to high levels in the inner integuments of ovules the day preceding testal (seed coat). deposition; in epidermal cells of growing organs; in tapetal cells of anthers; and in epidermis and trichomes of young leaves. The co-accumulation of ACL-A and ACL-B with the cytosolic ACC indicates that ACL generates the cytosolic pool of acetyl-CoA. The higher level of accumulation of mRNAs in the epidermis may be associated with cuticular wax formation. The co-accumulation of the ACL-A, ACL-B and ACC mRNAs in the inner integument a day preceding deposition of the testa may be associated with deposition of the flavonoid polymers phlobaphens (Stafford, "Metabolism and regulation of phenolics: gaps in our knowledge," in *Phytochemicals and Health*, D. L. Gustine and H. E. Flores, editors. *Amer. Soc. Plant Physiol.* (1995)).

Example 12

This example describes the effect of immunoprecipitation of ACL-A and ACL-B polypeptides from Arabidopsis extracts on ACL activity.

The antibodies of Example 6 can be used to determine the effect of immunoprecipitation on ACL activity in extracts of Arabidopsis. Aliquots of Arabidopsis extracts will be mixed with increasing quantities of each antiserum or with control preimmune serum. Following an incubation on ice, antigen-antibody complexes will be bound to Protein A-Agarose beads, which will be pelleted by centrifugation. The supernatant solutions will be assayed for ACL activity.

ACL enzymatic activity can be determined by adaptation of a spectrophotometric assay that was initially developed for animals (Takeda et al., *Meth. Enzymol.* 27: 153–160 (1969)) and has since been used to characterize ACL in extracts of pea (Kaethner and ap Rees, *Planta* 163: 290–294 (1985)) and *Brassica* (Ratledge et al., *Lipids* 32: 7–12 (1997)). The assay couples the rate of appearance of oxaloacetate production to the oxidation of NADH, with the enzyme malate dehydrogenase, resulting in a measurable change in absorbance at 340 nm.

Example 13

This example describes how the level of acetyl CoA in a plant can be increased by increasing the copy number of one or more genes involved in acetyl CoA production.

The level of acetyl CoA generated in a cell of a plant can be increased by increasing the accumulation of one or more of the enzymes involved in the generation of acetyl CoA. This can be achieved by introducing additional copies of the one or more genes into the genome of the organism. A copy of each acetyl CoA-producing gene is cloned into an appropriate transformation vector that carries a selectable marker gene and the vector is transformed into the organism of choice. Transformants are selected on the basis of the marker gene. Transformants are confirmed by Southern blot analysis of the DNA from putative transformants. In some cases, this single transformation event will introduce multiple copies of an acetyl CoA-producing gene. Alternatively, multiple copies of an acetyl CoA-producing gene are cloned into the transforming vector. Alternatively, an acetyl CoA-producing gene is cloned into transformation vectors that carry different selectable marker genes and multiple transformations are carried out to introduce multiple copies of an acetyl CoA-producing gene. In some cases, it is necessary to introduce a combination of acetyl CoA-producing genes. This is achieved by cloning a combination of acetyl CoA-producing genes into the same transformation vector or into different transformation vectors that carry different selectable marker genes.

Example 14

This example describes how the level of acetyl CoA in a plant can be increased by increasing the expression of one or more genes involved in acetyl CoA production.

The level of acetyl CoA generated in a cell of a plant can be increased by increasing the accumulation of one or more of the acetyl CoA-producing enzymes. This can be achieved by introducing into the genome of an organism copies of one or more acetyl CoA-producing genes or cDNAs fused to novel expression regulatory sequences that express the acetyl CoA-producing gene(s) at higher levels than normal. A copy of the acetyl CoA-producing gene or cDNA is fused to upstream (5') and/or downstream (3') transcriptional or translational regulatory sequences and the chimeric gene is cloned into an appropriate transformation vector that carries a selectable marker gene and the vector is transformed into the organism of choice. Transformants are selected on the basis of the marker gene. Transformants are confirmed by Southern blot analysis of the DNA from putative transformants. Multiple copies of each novel acetyl CoA-producing gene or combinations of novel acetyl CoA-producing genes can be introduced into the genome of an organism as described in Example 13.

Example 15

This example describes how the level of acetyl CoA in a plant can be decreased by using antisense technology.

The level of acetyl CoA generated in a cell of a plant can be decreased by decreasing the accumulation of one or more enzymes involved in acetyl CoA production. This can be achieved by introducing into the genome a transgene that expresses an antisense RNA of one or more enzymes involved in acetyl CoA production. The antisense RNA gene consists of a cDNA coding for an acetyl CoA producing enzyme, fused to upstream (5') and/or downstream (3') transcriptional or translational regulatory sequences with the cDNA being in the opposite orientation from the norm. This antisense gene is cloned into an appropriate transformation vector and transformed into a genome as described in Example 14. Multiple copies of the antisense gene can be introduced into a genome as described in Example 14. Antisense genes for a combination of acetyl CoA-generating enzymes can be introduced into a genome as described in Example 14.

Example 16

This example describes how to decrease the level of acetyl CoA in a plant using ribozymes.

The level of acetyl CoA generated in a cell of a plant can be decreased by decreasing the accumulation of one or more acetyl CoA-producing enzymes. This can be achieved by introducing into the genome a transgene that expresses a ribozyme targeted against a mRNA coding for an acetyl CoA-producing enzyme. The ribozyme-containing gene consists of the full-length or partial cDNA coding for an acetyl CoA-generating enzyme in opposite orientation from the norm into which a ribozyme sequence is inserted. This ribozyme containing cDNA is fused to upstream (5') and/or downstream (3') transcriptional or translational regulatory sequences. This ribozyme containing gene is cloned into an appropriate transformation vector and transformed into a genome as described in Example 14. Multiple copies of the ribozyme-containing gene can be introduced into a genome as described in Example 14. Ribozyme-containing genes targeted against a combination of acetyl-CoA-generating enzymes can be introduced into a genome as described in Example 14.

Example 17

This example describes how the level of acetyl CoA in a plant can be increased or decreased by using gene replacement.

The level of acetyl CoA generated in a cell of a plant can be altered by altering the activity of one or more acetyl CoA-producing enzymes. This can be achieved by a gene replacement method via homologous recombination. In this method, the endogenous acetyl CoA-producing gene is replaced by a mutagenized acetyl-CoA-producing gene. The mutagenized acetyl CoA-producing gene codes for an acetyl CoA-producing enzyme that is either more or less efficient in catalysis than the one encoded by the endogenous, replaced gene. The acetyl CoA-producing gene is mutagenized by one or more nucleotide deletions, insertions, duplications or replacements. The mutagenized gene is fused to a selectable marker gene and introduced into a cell. Homologous recombination events that may result in gene replacement are selected on the basis of the selectable marker gene. Gene replacements are confirmed by Southern blot analysis or PCR and DNA sequencing.

Example 18

This example describes how to decrease the level of acetyl CoA in a plant by using co-suppression.

The level of acetyl CoA generated in a cell of a plant can be decreased by decreasing the accumulation of one or more of the acetyl CoA-producing enzymes. This can be achieved by co-suppression. For example, the cDNA coding for an acetyl-CoA-producing enzyme is fused to upstream (5') and/or downstream (3') transcriptional or translational regulatory sequences and the chimeric gene is cloned into an appropriate transformation vector that carries a selectable marker gene and the vector is transformed into the organism of choice. Transformants are selected on the basis of the marker gene. Transformants are confirmed by Southern blot analysis of the DNA from putative transformants. Most of the transgenic organisms that will be derived from such experimentations will express the transgene. However, in a few cases, the transgene will co-suppress the expression of the endogenous acetyl-CoA producing gene. To identify these co-suppressing plants, extracts from at least 100 transgenic plants will be analyzed for the enzymatic activity of the acetyl-CoA-producing enzyme.

Example 19

This example describes how to increase acetyl-CoA levels by overexpressing an acetyl-CoA-producing enzyme (eg., ACS) in a model organism (i.e., Arabidopsis).

The full-length ACS cDNA is cloned into a plant expression vector such as pBI101, down-stream of the Cauliflower Mosaic Virus 35 S RNA promoter (CaMV, 35 S promoter). The resulting recombinant vector is transformed into *Agrobacterium tumefaciens*. The resulting strain is used to transform Arabidopsis plants by vacuum infiltration protocols. Namely, flower buds of Arabidopsis are dipped for 1–5 minutes into a culture of the *Agrobacterium tumefaciens* strain. Plants are allowed to set seed, which are collected.

Seeds are germinated on agar plates containing 50–100 pg/ml kanamycin, and resistant, transformed seedlings that grow on this medium are transferred to soil. Between 10 and 50 independently transformed seedlings are collected and allowed to flower and set seed. This T2 generation of seed is homozygous for the transgene. Confirmation of the transgenic nature of the seed is undertaken by extracting DNA from the resulting T2 generation seedlings and performing Southern blot analysis using the ACS cDNA and the CaMV, 35 S promoter as probes.

Transgenic plants are tested for expression of the ACS transgene, for increased ACS activity and for increased accumulation of acetyl-CoA.

Expression of the ACS transgene is carried out by analyzing the accumulation of the ACS mRNA and polypeptide. The ACS mRNA can be detected by Northern hybridization with the ACS cDNA, or by RNase protection assays using an ACS transgene-specific probe.

The ACS polypeptide is detected by Western blot analysis of total proteins separated by SDS-PAGE and probed with ACS-specific antibodies. ACS activity is determined by incubating an extract with labeled acetate, in the presence of CoA and ATP, and monitoring the production of labeled acetyl-CoA. The accumulation of acetyl-CoA is monitored by extracting seedlings with 10% trichloroacetic acid.

The resulting extract is subjected to High Pressure Liquid Chromatography, using a C-18 reverse phase column. The solvent for elution is $KH_2PO_4$, pH 5.5, in acetonitrile. Elution of acetyl-CoA is identified by co-elution with authentic acetyl-CoA. Acetyl-CoA concentration is determined based on absorbance at 254 nm.

Example 20

This example describes how to decrease acetyl-CoA levels by expressing an antisense RNA for an acetyl-CoA-producing enzyme (eg., ACS) in a model organism (i.e., Arabidopsis).

The full-length (or partial fragment) ACS cDNA is cloned into a plant expression vector such as pBIO101, downstream of the Cauliflower Mosaic Virus 35 S RNA promoter (CaMV, 35 S promoter), but in opposite orientation from normal. The resulting recombinant vector is transformed into *Agrobacterium tumefaciens*. The resulting strain is used to transform Arabidopsis plants by vacuum infiltration protocols. Namely, flower buds of Arabidopsis are dipped for 1 minute into a culture of the *Agrobacterium tumefaciens* strain. Plants are allowed to set seed, which are collected.

Seeds are germinated on agar plates containing 50–100 μg/ml kanamycin, and resistant, transformed seedlings that grow on this medium are transferred to soil. Between 10 and 50 independently transformed seedlings are collected and allowed to flower and set seed. This T2 generation of seed is homozygous for the transgene. Confirmation of the transgenic nature of the seed is undertaken by extracting DNA from the resulting T2 generation seedlings and performing Southern blot analysis using the ACS cDNA and the CaMV, 35 S promoter as the probe.

Transgenic plants are tested for expression of the antisense ACS transgene, for decreased accumulation of the ACS polypeptide, for decreased ACS activity, and for decreased accumulation of acetyl-CoA.

Expression of the antisense ACS transgene is carried by analyzing the accumulation of the ACS antisense RNA. RNA is extracted from transgenic seedlings and the ACS antisense RNA is detected by Northern hybridization, or by RNase protection assays using an ACS sense strand riboprobe.

The ACS polypeptide is detected by Western blot analysis of total proteins separated by SDS-PAGE and probed with ACS-specific antibodies. ACS activity is determined by incubating an extract with labeled acetate, in the presence of CoA and ATP, and monitoring the production of labeled acetyl-CoA.

The accumulation of acetyl-CoA is monitored by extracting seedlings with 10% trichloroacetic acid. The resulting extract is subjected to High Pressure Liquid Chromatography, using a C-18 reverse phase column. The solvent for elution is $KH_2PO_4$, pH 5.5, in acetonitrile. Elution of acetyl-CoA is identified by co-elution with authentic acetyl-CoA. Acetyl-CoA concentration is determined based on absorbance at 254 nm.

Example 21

This example describes the alteration of ACS levels in a plant using sense and antisense nucleic acids.

The full-length ACS cDNA was cloned into the plant expression vector designated pCB200, which was derived from the vector pBI121 (Clonetech) by replacing the kanamycin resistance (kan-r) gene with the *E. coli* BAR gene for resistance to the herbicide Liberty (Becker et al., *Plant Mol. Biol.* 20: 1195–1197 (1992)). The full-length ACS cDNA was cloned into pCB200 downstream of the CaMV 35 S promoter in normal and opposite orientation for sense and antisense expression, respectively, using standard techniques (Sambrook et al., *Molecular Cloning: a Laboratory Manual.* Cold Spring Harbor Laboratory, N.Y. (1989)). Restriction endonucleases and DNA ligase (GibcoBRL, Grand Island, N.Y.) were used with protocols suggested by the manufacturers. The resulting vectors were separately transformed into *Agrobacterium tumefaciens*. The resulting strain was used to transform *Arabidopsis thaliana* (ecotype Columbia) plants by vacuum infiltration protocols, based on the procedures described by Bechtold et al. (*Methods Molec. Biol.* 82: 259–266 (1993)). Briefly, flower buds of Arabidopsis were dipped for 1 min into a culture of the *A. tumefaciens* strain. Plants were allowed to set seed, which was then collected.

Transgenic plants were selected by sowing seeds in sterile soil. Fourteen days later, the seedlings were sprayed with a solution of 0.5% glufosinate (w/v) (active ingredient of the herbicide Liberty). Non-transgenic plants died within about 7 days, whereas transgenic seedlings survived, were grown to maturity, and seeds were collected.

Each transgenic line from an individual transformed plant was considered to be an independent transformation event. In the following generations, seeds were harvested from transgenic lines individually and were further tested for resistance to the herbicide Liberty. A transgenic line was considered to be homozygous when there was only one copy of the transgene incorporated into its genome and all of the tested progeny seedlings (more than 50) were resistant to Liberty.

Two independent transgenic lines of ACS antisense plants were generated. The first line was characterized through the T3 generation and ACS enzyme activity levels as low as 20% of wild-type activity were observed. The second line was characterized through the T2 generation and ACS enzyme activity levels as low as 11% of wild-type activity were observed.

Twenty independent transgenic lines of ACS sense plants were generated. One line was characterized through the T3 generation, whereas all other lines were characterized through the T2 generation. ACS enzyme activity levels as high as 166% to 219% of wild-type activity were observed.

Thus, these data show that the expression of ACS, which generates acetyl CoA, can be increased and decreased.

Example 22

This example describes the alteration of pPDH levels in a plant using antisense nucleic acids.

Using the methods of Example 21, full-length pPDH $E1_\alpha$ or $pPDHE1_\beta$ cDNA was cloned into the plant expression vector designated pCB200 downstream of the CaMV 35 S promoter in opposite orientation from normal for antisense RNA expression. Two independent transgenic lines of $pPDHE1_\alpha$ antisense plants and three independent transgenic lines of $pPDHE1_\beta$ antisense plants were generated and have been grown through the T1 generation. These plants will be analyzed in accordance with the methods of Example 21.

Example 23

This example describes the alteration of ALDH levels in a plant using sense and antisense nucleic acids.

Using the methods of Example 21, full-length ALDH cDNA was cloned into plant expression vectors in normal and opposite orientation for sense and antisense expression as follows:

pCGN8641, napin promoter, kan-r gene (2 sense; 1 antisense)

pCGN8643, napin promoter, kan-r gene (2 antisense; 1 sense)

pCGN8640, CaMV 35 S promoter, plant resistance gene bar (Liberty herbicide) (2 antisense; 1 sense)

pCGN8644, CaMV 35 S promoter, bar gene (2 sense; 1 antisense)

pKMB (Mylne and Botella, *Plant Molec. Biol. Reporter* 16: 257–262 (1998)), CaMV 35 S promoter, bar gene (3 sense)

pSMB (Mylne and Botella (1998), supra), CaMV 35 S promoter, bar gene (3 anti sense).

A binary vector for plant transformation, pCGN5139, was constructed from pCGN1558 (McBride and Summerfelt, *Plant Molecular Biology* 14: 269–276 (1990)). The polylinker of pCGN1558 was replaced as a Hin dII/Asp718 fragment with a polylinker containing unique restriction endonuclease sites, Asc I, Pac I, Xba I, Swa I, Bam HI and Not I. The Asp718 and Hin dIII restriction endonuclease sites are retained in pCGN5139.

A series of turbo binary vectors are constructed to allow for the rapid cloning of DNA sequences into binary vectors containing transcriptional initiation regions (promoters) and transcriptional termination regions.

The plasmid pCGN8618 was constructed by ligating oligonucleotides 5'TCGAGGATCCGCGGCCGCAAGCTTCCTGCAGG-3' [SEQ ID NO: 31] and 5'-TCGACCTGCAGGAAGCTTGCGGCCGCGGATCC-3' [SEQ ID NO: 32] into Sal I/Xho I-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and Hin dIII and blunt-ended by filling in the 5' overhangs with Klenow fragment. A plasmid containing the insert oriented so that the napin promoter was closest to the blunted Asp718I site of pCGN5139 and the napin 3' was closest to the blunted Hin dII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTTGCGGCCGCGGATCC-3' [SEQ ID NO: 33] and 5'-TCGAGGATCCGCGGCCGCAAGCTTCCTGCAGG-3' [SEQ ID NO: 34] into Sal I/Xho I-digested pCGN7770. A fragment containing the napin promoter, polylinker and napin 3' region was removed from pCGN8619 by digestion with Asp718I; the fragment was blunt-ended by filling in the 5' overhangs with Klenow fragment and then ligated into pCGN5139 that had been digested with Asp718I and Hin dIII and blunt-ended by filling in the 5' overhangs with Klenow fragment. A plasmid containing the insert oriented so that the napin promoter was closest to the blunted Asp718I site of pCGN5139 and the napin 3' was closest to the blunted Hin dIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAA GCT-TCCTGCAGGAGCT -3' [SEQ ID NO: 35] and 5'-CCTGCAGGAAGCTTGCGGCCGCGGATCC-3' [SEQ ID NO: 36] into Sal I/Sac I-digested pCGN7787. A fragment containing the d35 S promoter, polylinker and tml 3' region was removed from pCGN8620 by complete digestion with Asp7181 and partial digestion with Not I. The fragment was blunt-ended by filling in the 5' overhangs with Klenow fragment then ligated into pCGN5139 that had been digested with Asp718I and Hin dIII and blunt-ended by filling in the 5' overhangs with Klenow fragment. A plasmid containing the insert oriented so that the d35 S promoter was closest to the blunted Asp718I site of pCGN5139 and the tml 3' was closest to the blunted Hin dIII site was subjected to sequence analysis to confirm both the insert orientation and the integrity of cloning junctions. The resulting plasmid was designated pCGN8624.

pCGN8640 is a modification of pCGN8624. A 938 bp Pst I fragment isolated from transposon Tn7 which encodes bacterial spectinomycin and streptomycin resistance (Fling et al., *Nucleic Acids Research* 13(19):7095–7106 (1985)), a determinant for *E. coli* and Agrobacterium selection, was blunt ended with Pfu polymerase. The blunt-ended fragment was ligated into pCGN8624 that had been digested with Spe I and blunt-ended with Pfu polymerase. The region containing the Pst I fragment was sequenced to confirm both the insert orientation and the integrity of cloning junctions.

The spectinomycin resistance marker was introduced into pCGN8622 and pCGN8623 as follows. A 7.7 Kbp AvrII-SnaBI fragment from pCGN8640 was ligated to a 10.9 Kbp Avr II-Sna BI fragment from pCGN8623 or pCGN8622. The resulting plasmids were pCGN8641 and pCGN8643, respectively.

The plasmid pCGN8644 was constructed by ligating oligonucleotides 5'-GATCACCTGCAGGAAGCTTGCGG CCGCGGATCCAATGCA-3' [SEQ ID NO: 37] and 5'-TTGGATCCGCGGCCGCAAGCTTCCTGCAGGT-3' [SEQ ID NO: 38] into Bam HI-Pst I digested pCGN8640.

Transgenic plants are generated and analyzed according to the methods of Example 21, with the exception that transgenic plants generated with the vectors pCGN8641 and pCGN8643 were selected on the basis of kanamycin resistance. For this selection, seeds were surface-sterilized by incubating them for 7 min in 50% (v/v) regular bleach (5.25% sodium hypochlorite) and 0.02% Triton X-100 followed by rinsing them three times with sterile water. Seeds were sown in Petri plates containing MS selection medium (50 μg/ml kanamycin, 1×Murashige and Skoog's salts (Sigma Chemical Co., St. Louis, Mo.), 1% sucrose, 1×Gamborg's vitamin (Sigma), 0.5 g/l MES, pH 5.7, and 0.8% purified agar (Becton Dickinson, Cockeysville, Md.)). Approximately 10–14 days after sowing, kanamycin-resistant seedlings were transferred into sterile soil (Sunshine Mix, Sun Gro Horticulture, Bellevue, Wash.). Plants were grown at 23° C. either under continuous light or under a photoperiod of 16 hrs illumination followed by 8 hrs of darkness. Plants were watered once a week with Nutri-culture soluble fertilizer special blend 21–8–18 (Plant Marvel Laboratory, Chicago Heights, Ill.).

Each transgenic line from an individual transformed plant was considered to be an independent transformation event. In the following generations, seeds were harvested from transgenic lines individually and were further grown on MS selection medium to investigate the segregation of the kanamycin resistance trait. For each test of the segregation of kanamycin resistance, more than 30 seeds were used. A transgenic line was considered to be homozygous when there was only one copy of the transgene incorporated into its genome and all of the tested progeny seedlings (more than 50) were kanamycin resistant.

Example 24

This example describes the alteration of PDC levels in a plant using sense and antisense nucleic acids.

Using the methods of Example 21, full-length PDC cDNA was cloned into plant expression vectors in normal and opposite orientation for sense and antisense expression as follows:

pCGN8641, napin promoter, kan-r gene (1 sense; 1 antisense)

pCGN8643, napin promoter, kan-r gene (1 sense)

pCGN8640, CaMV 35 S promoter, bar gene (1 sense)

pCGN8644, CaMV 35 S promoter, bar gene (1 sense)

pKMB, CaMV 35 S promoter, bar gene (1 antisense)

pSMB, CaMV 35 S promoter, bar gene (1 antisense).

Transgenic plants are generated and analyzed according to the methods of Examples 21 and 23.

Example 25

This example describes the alteration of ACL levels in a plant using sense and antisense nucleic acids.

Using the methods of Example 21, full-length ACL-A1 or ACL-B2 cDNA was cloned into plant expression vectors in normal and opposite orientation for sense and antisense expression as follows:

pBI121 derivative plasmid, CaMV 35 S promoter, kan-r gene (1 ACL-A1 sense; 1 ACL-B2 sense; 1 ACL-A1 antisense; 1 ACL-B2 antisense)

pBl121 derivative plasmid, deleted CAC1 promoter (nucleotides −529 to +32 of the CAC1 promoter, wherein the nucleotides are numbered relative to the adenosine nucleotide of the ATG translation start codon, which is +1), kan-r gene (1 ACL-A1 sense; 1 ACL-B2 sense)

pBI121derivative plasmid, CaMV 35 S promoter, kan-r gene (1 ACL-A1 (fused to plastid target sequence) sense).

All transgenic plants were selected upon the basis of kanamycin resistance as described in Example 23.

Transgenic plants comprising sense ACL-A1 under the control of the deleted CAC1 promoter were generated and have been grown through the T2 generation. Such plants exhibit an altered phenotype of very large leaves.

Transgenic plants comprising antisense ACL-A1 under the control of the CaMV 35 S promoter were generated and have been grown through the T2 generation. Such plants exhibit two types of phenotypes. One type of phenotype comprises a much reduced plant body, shorter and thinner inflorescence stalks, smaller or non-opened flowers, reduced and occasionally early senescing petals, anthers with apparent problems of timing or dehiscence mechanisms, siliques, if present, are reduced, partially filled with seed or empty, smaller dessicated seeds within siliques, premature dehiscence within filled siliques, and very reduced leaves exhibiting anthocyanin production.

The other type of phenotype comprises smaller plants with milder versions of the characteristics described for the preceding phenotype, thinner, curled siliques with more easily differentiated external seed outlines, which often contain shriveled, dry seeds, and delayed dehiscence.

Other transgenic plants are generated and analyzed according to the methods of Examples 21 and 23.

All of the references cited herein, including patents, patent applications, and publications, are hereby incorporated in their entireties by reference.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

What is claimed is:

1. An isolated or purified nucleic acid molecule encoding the E3 subunit of an Aabidopsis plastidic pyruvate dehydrogenase (pPDH).

2. An isolated or purified nucleic acid molecule, wherein said nucleic acid molecule is (i) DNA and comprises SEQ ID NO: 27, SEQ ID NO: 29, a sequence that encodes SEQ ID NO: 28 or a sequence that encodes SEQ ID NO: 30, or (ii) RNA and comprises a sequence encoded by SEQ ID NO: 27, a sequence encoded by SEQ ID NO: 29, a sequence that encodes SEQ ID NO: 28 or a sequence that encodes SEQ ID NO: 30.

3. A vector comprising a nucleic acid molecule of claim 1.

4. A vector comprising a nucleic acid molecule of claim 2.

5. A host cell comprising a vector of claim 3.

6. A host cell comprising a vector of claim 4.

7. A ribozyme that can cleave an RNA molecule encoding the E3 subunit of an Arabidopsis pPDH.

8. A method of altering the level of an enzyme in a plant cell, a plant tissue, a plant organ, or a plant, which method comprises contacting said plant cell, plant tissue, plant organ or plant with a vector comprising a nucleic acid molecule selected from the group consisting of (i) a coding sequence for the E3 subunit of pPDH or (ii) a nucleic acid molecule comprising or encoding a ribozyme to an RNA molecule transcribed from a coding sequence of (i), wherein said vector comprising a nucleic acid molecule of (i) increases or decreases the level of said enzyme in said plant cell, plant tissue, plant organ or plant, and wherein said vector comprising a nucleic acid molecule of (ii) decreases the level of said enzyme in said plant cell, plant tissue, plant organ or plant.

9. The method of claim 8, wherein said enzyme is pPDH.

10. The method of claim 8, wherein the alteration of said enzyme results in an alteration of the level of acetyl CoA in said plant cell, plant tissue, plant organ or plant.

11. The method of claim 9, wherein the alteration of said enzyme results in an alteration of the level of acetyl CoA in said plant cell, plant tissue, plant organ or plant.

12. A plant cell, a plant tissue, a plant organ or a plant in which the level of pPDH has been altered in accordance with the method of claim 8.

13. A plant cell, a plant tissue, a plant organ or a plant in which the level of pPDH has been altered in accordance with the method of claim 9.

14. A plant cell, a plant tissue, a plant organ or a plant in which the level of acetyl CoA has been altered in accordance with the method of claim 10.

15. A plant cell, a plant tissue, a plant organ or a plant in which the level of acetyl CoA has been altered in accordance with the method of claim 11.

16. A ribozyme that can cleave an RNA molecule of claim 2.

* * * * *

UNITED STATES PATENT AND TRADEMARK OFFICE
CERTIFICATE OF CORRECTION

PATENT NO. : 6,764,851 B2
DATED : July 20, 2004
INVENTOR(S) : Nikolau et al.

It is certified that error appears in the above-identified patent and that said Letters Patent is hereby corrected as shown below:

Title page,
Item [75], Inventors, "Jerry L. Johnson," "Carolyn C. Allred," "Beth Fatland," and "Tsui-Jung Wen," should be deleted from the list of inventors.

Column 105,
Line 56, "Aabidopsis" should read -- Arabidopsis --.

Signed and Sealed this

Twenty-sixth Day of October, 2004

JON W. DUDAS
*Director of the United States Patent and Trademark Office*